US009818948B2

(12) United States Patent
Jatsch et al.

(10) Patent No.: US 9,818,948 B2
(45) Date of Patent: Nov. 14, 2017

(54) CARBAZOLE DERIVATIVES FOR ORGANIC ELECTROLUMINESCENCE DEVICES

(75) Inventors: Anja Jatsch, Frankfurt am Main (DE); Amir Hossain Parham, Frankfurt am Main (DE); Christof Pflumm, Darmstadt (DE); Philipp Stoessel, Frankfurt am Main (DE); Jonas Valentin Kroesser, Frankfurt am Main (DE); Rémi Manouk Anémian, Seoul (KR); Thomas Eberle, Landau (DE)

(73) Assignee: Merck Patent GmbH, Darmstadt (DE)

( * ) Notice: Subject to any disclaimer, the term of this patent is extended or adjusted under 35 U.S.C. 154(b) by 520 days.

(21) Appl. No.: 14/346,187

(22) PCT Filed: Aug. 23, 2012

(86) PCT No.: PCT/EP2012/003563
§ 371 (c)(1),
(2), (4) Date: Mar. 20, 2014

(87) PCT Pub. No.: WO2013/041176
PCT Pub. Date: Mar. 28, 2013

(65) Prior Publication Data
US 2014/0225046 A1    Aug. 14, 2014

(30) Foreign Application Priority Data

Sep. 21, 2011 (EP) .................... 11007693

(51) Int. Cl.
*H01L 51/54* (2006.01)
*C09K 11/06* (2006.01)
*H01L 51/00* (2006.01)
*C07D 405/14* (2006.01)
*C07F 9/6568* (2006.01)
*C07D 405/04* (2006.01)
*C07D 409/04* (2006.01)
*C07D 409/14* (2006.01)
(Continued)

(52) U.S. Cl.
CPC ........ *H01L 51/0052* (2013.01); *C07D 209/86* (2013.01); *C07D 209/88* (2013.01); *C07D 209/96* (2013.01); *C07D 405/04* (2013.01); *C07D 405/14* (2013.01); *C07D 409/04* (2013.01); *C07D 409/14* (2013.01); *C07D 487/04* (2013.01); *C07D 487/10* (2013.01); *C07D 491/04* (2013.01); *C07D 491/14* (2013.01); *C07D 495/04* (2013.01); *C07D 495/14* (2013.01); *C07F 7/0814* (2013.01); *C07F 9/65683* (2013.01); *C07F 9/65685* (2013.01); *C09B 57/00* (2013.01); *H01L 51/0071* (2013.01); *H01L 51/0072* (2013.01); *H01L 51/0073* (2013.01); *H01L 51/0074* (2013.01); *H01L 51/5016* (2013.01); *Y02E 10/549* (2013.01)

(58) Field of Classification Search
CPC C07F 7/0814; C07F 9/65685; C07F 9/65683; C07D 209/00; C07D 209/56; C07D 209/80; C07D 209/82; C07D 209/86; C07D 209/88; C07D 405/00; C07D 405/02; C07D 405/04; C07D 405/10; C07D 405/14; C07D 409/00; C07D 409/02; C07D 409/04; C07D 409/14; C07D 487/00; C07D 487/02; C07D 487/04; C07D 487/10; C07D 491/00; C07D 491/02; C07D 491/04; C07D 491/10; C07D 491/14; C07D 495/00; C07D 495/02; C07D 495/04; C07D 495/12; C07D 495/14; H01L 51/0032; H01L 51/0052; H01L 51/0071; H01L 51/0072; H01L 51/0073; H01L 51/0074; H01L 51/50; H01L 51/5012; H01L 51/5016
USPC ....... 428/690, 691, 917, 411.4, 336; 427/58, 427/66; 313/500–512; 257/40, 88–104, 257/E51.001–E51.052; 252/301.16–301.35, 519.3; 548/418, 407, 548/417, 414; 546/49
See application file for complete search history.

(56) References Cited

U.S. PATENT DOCUMENTS 9,126,970 B2 * 9/2015 Pflumm ............... C07D 209/82
2008/0024054 A1  1/2008 Itoh et al.
(Continued)

FOREIGN PATENT DOCUMENTS

CN  101659638 A  3/2010
DE  WO 2011057706 A2 *  5/2011  ........... C07D 403/10
(Continued)

OTHER PUBLICATIONS

English Translation of Japanese Office Action for application No. 2014-531119, dated Mar. 29, 2016.
(Continued)

*Primary Examiner* — Andrew K Bohaty

(57) ABSTRACT

The present invention describes carbazole derivatives formula (1), where the following applies to the symbols used: Y is on each occurrence, identically or differently, CR or N; X is selected from C(R1)2, O, S, PR1, P(=O)R1 or BR1; characterized in that at least one group R is present which stands, identically or differently on each occurrence, for a group of the following formula (2), and/or in that at least one group R1 is present which stands for a group of the following formula (3) or (4), in particular for use as triplet matrix materials in organic electroluminescent devices. The invention furthermore relates to a process for the preparation of the compounds according to the invention and to electronic devices comprising same.

15 Claims, No Drawings

(51) Int. Cl.
  *C07D 487/04* (2006.01)
  *C07D 487/10* (2006.01)
  *C07D 491/04* (2006.01)
  *C07D 491/14* (2006.01)
  *C07D 495/04* (2006.01)
  *C07D 495/14* (2006.01)
  *C07D 209/86* (2006.01)
  *C07D 209/88* (2006.01)
  *C07D 209/96* (2006.01)
  *C07F 7/08* (2006.01)
  *C09B 57/00* (2006.01)
  *H01L 51/50* (2006.01)

(56) References Cited

U.S. PATENT DOCUMENTS

| | | | |
|---|---|---|---|
| 2009/0309488 A1* | 12/2009 | Kato | C07D 487/04 313/504 |
| 2010/0012931 A1* | 1/2010 | Kato | C07D 209/86 257/40 |
| 2011/0272684 A1 | 11/2011 | Parham et al. | |
| 2012/0068170 A1 | 3/2012 | Pflumm et al. | |
| 2012/0223276 A1* | 9/2012 | Parham | C07D 403/10 252/500 |
| 2013/0126856 A1* | 5/2013 | Yokoyama | C07D 209/70 257/40 |
| 2014/0091265 A1 | 4/2014 | Stoessel et al. | |
| 2014/0138670 A1 | 5/2014 | Nakagawa et al. | |

FOREIGN PATENT DOCUMENTS

| | | | | |
|---|---|---|---|---|
| EP | 2301926 A1 | 3/2011 | | |
| JP | 2008511970 A | 4/2008 | | |
| JP | WO 2012014500 A1 * | 2/2012 | ........... | C07D 209/70 |
| JP | 2012-126673 A | 7/2012 | | |
| JP | 2014520096 A | 8/2014 | | |
| KR | 2011002156 | 1/2011 | | |
| KR | 20110002156 A | 1/2011 | | |
| KR | 10-2011-0102055 | † | 9/2011 | |
| KR | 2012-009984 | 2/2012 | | |
| KR | 2012-034140 | 4/2012 | | |
| KR | 2012-065214 | 6/2012 | | |
| WO | 2009/148015 A1 † | 12/2009 | | |
| WO | WO-2010083872 A2 | 7/2010 | | |
| WO | 2010/136109 A1 † | 12/2010 | | |
| WO | WO-2010136109 A1 | 12/2010 | | |
| WO | WO-2011057706 A2 | 5/2011 | | |
| WO | WO-2012026780 A1 | 3/2012 | | |
| WO | WO-2013011954 A1 | 1/2013 | | |

OTHER PUBLICATIONS

International Search Report for PCT/EP2012/003563 dated Nov. 8, 2012.
Caplus Database, Accession No. XP-002684355, (2011).
Caplus Database, Accession No. XP-002684349, (2012).
Caplus Database, Accession No. XP-002684350, (2012).
Caplus Database, Accession No. XP-002684351, (2012).
Caplus Database, Accession No. XP-002684352, (2012).
Caplus Database, Accession No. XP-002684353, (2012).

* cited by examiner
† cited by third party

CARBAZOLE DERIVATIVES FOR ORGANIC ELECTROLUMINESCENCE DEVICES

CROSS-REFERENCE TO RELATED APPLICATIONS

This application is a national stage application (under 35 U.S.C. §371) of PCT/EP2012/003563, filed Aug. 23, 2012, which claims benefit of European application 11007693.2, filed Sep. 21, 2011.

The present invention describes carbazole derivatives, in particular for use as triplet matrix materials in organic electroluminescent devices. The invention furthermore relates to a process for the preparation of the compounds according to the invention and to electronic devices comprising these compounds.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed are frequently organometallic complexes which exhibit phosphorescence instead of fluorescence. For quantum-mechanical reasons, an up to four-fold energy and power efficiency is possible using organometallic compounds as phosphorescent emitters. In general, there is still a need for improvement in OLEDs, in particular also in OLEDs which exhibit triplet emission (phosphorescence), for example with respect to efficiency, operating voltage and lifetime.

The properties of phosphorescent OLEDs are not determined only by the triplet emitters employed. In particular, the other materials used, such as, for example, matrix materials, are also of particular importance here. Improvements in these materials may thus also result in significant improvements in the OLED properties.

In accordance with the prior art, use is made, inter alia, of indolocarbazole derivatives (for example in accordance with WO 2007/063754 or WO 2008/056746) or indenocarbazole derivatives (for example in accordance with WO 2010/136109 or WO 2011/000455), in particular those which are substituted by electron-deficient heteroaromatic compounds, such as triazine, as matrix materials for phosphorescent emitters. Furthermore, bisdibenzofuran derivatives (for example in accordance with EP 2301926) are used, for example, as matrix materials for phosphorescent emitters. However, there is still a need for improvement on use of these matrix materials, in particular with respect to the efficiency, lifetime and operating voltage of the device.

The object of the present invention is the provision of compounds which are suitable for use in a fluorescent or in particular in a phosphorescent OLED, in particular as matrix material. In particular, the object of the present invention is to provide matrix materials which are also suitable for green—and if desired also for blue-phosphorescent OLEDs and which result in good efficiency, a long lifetime and a low operating voltage. The properties of the matrix materials in particular have a significant influence on the lifetime and efficiency of the organic electroluminescent device.

Surprisingly, it has been found that electroluminescent devices which comprise compounds of the following formula (1) have improvements compared with the prior art, in particular on use as matrix materials for phosphorescent dopants.

The present invention therefore relates to a compound of the following formula (1),

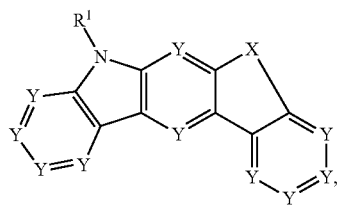

formula (1)

where the following applies to the symbols used:

Y is on each occurrence, identically or differently, CR or N;

X is selected from $C(R^1)_2$, O, S, $PR^1$, $P(=O)R^1$ or $BR^1$;

R, $R^1$ is on each occurrence, identically or differently, H, D, F, Cl, Br, I, $N(R^2)_2$, $N(Ar)_2$, $C(=O)Ar$, $P(=O)Ar_2$, $S(=O)Ar$, $S(=O)_2Ar$, $CR^2=CR^2Ar$, CN, $NO_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $C=O$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a combination of these systems; two or more substituents R here, together with the atoms to which they are bonded, or two substituents $R^1$, together with the atom to which they are bonded, may also form a mono- or polycyclic, aliphatic or aromatic ring system with one another;

Ar is on each occurrence, identically or differently, an aromatic or heteroaromatic ring system, preferably an aryl or heteroaryl group having 5 to 40 aromatic ring atoms, which may be substituted by one or more radicals $R^3$;

$R^2$ is on each occurrence, identically or differently, H, D, F, Cl, Br, I, $N(R^3)_2$, $N(Ar)_2$, $C(=O)Ar$, $P(=O)Ar_2$, $S(=O)$ Ar, $S(=O)_2Ar$, $CR^3=CR^3Ar$, CN, $NO_2$, $Si(R^3)_3$, $B(OR^3)_2$, $OSO_2R^3$, a straight-chain alkyl, alkoxy or thioalkoxy group having 1 to 40 C atoms or a branched or cyclic alkyl, alkoxy or thioalkoxy group having 3 to 40 C atoms, each of which may be substituted by one or more radicals $R^3$, where one or more non-adjacent $CH_2$ groups may be replaced by $R^3C=CR^3$, $C\equiv C$, $Si(R^3)_2$, $C=O$, $C=NR^3$, $P(=O)(R^3)$, SO, $SO_2$, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 40 aromatic ring atoms, which may be substituted by one or more radicals $R^3$, or an aralkyl or heteroaralkyl group having 5 to 40 aromatic ring atoms, which may be substituted by one or more radicals $R^3$, or a combination of these systems;

$R^3$ is on each occurrence, identically or differently, H, D or an aliphatic hydrocarbon radical having 1 to 20 C atoms or an aryl or heteroaryl group having 5 to 40 ring atoms or a combination of these groups;

with the proviso that, if one or more of the groups R, $R^1$, $R^2$, $R^3$, Ar or $Ar^1$ contain heteroaryl groups which do not conform to the formulae (2), (3) or (4), these are not electron-deficient heteroaryl groups;
characterised in that at least one group R is present which stands, identically or differently on each occurrence, for a group of the following formula (2),

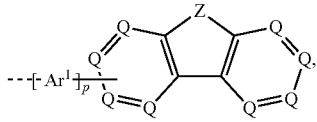

formula (2)

where the dashed bond indicates the linking of the group of the formula (2), $R^2$ has the above-mentioned meanings, and furthermore:
Q is C if the group of the formula (2) is linked to $Ar^1$ or to the remainder of the molecule via this group; or is, identically or differently on each occurrence, $CR^2$ or N in the other cases;
Z is $NR^2$ or S;
$Ar^1$ is a divalent aromatic or heteroaromatic ring system having 5 to 40 aromatic ring atoms, which may be substituted by one or more radicals $R^2$;
p is 0 or 1;
and/or in that at least one group $R^1$ is present which stands for a group of the following formula (3) or (4),

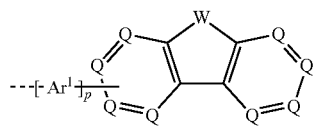

formula (3)

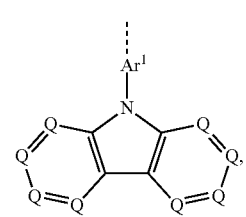

formula (4)

where the dashed bond indicates the linking of the group of the formula (3) or (4), $R^2$, $Ar^1$, Q and p have the above-mentioned meanings, and furthermore:
W is $NR^2$, O or S.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example thiophene, etc., or a condensed (fused) aryl or heteroaryl group, for example naphthalene, anthracene, phenanthrene, dibenzofuran, etc. Aromatic rings linked to one another by a single bond, such as, for example, biphenyl, are, by contrast, not referred to as an aryl or heteroaryl group, but instead as an aromatic ring system.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are connected, for example, by a short alkyl group. Furthermore, aromatic rings linked to one another by a single bond, such as, for example, biphenyl, are referred to as an aromatic ring system in the sense of this application.

An electron-deficient heteroaryl group in the sense of the present invention is defined as a 5-membered ring heteroaryl group having at least two heteroatoms, for example imidazole, oxazole, oxadiazole, etc., or as a 6-membered ring heteroaryl group having at least one heteroatom, for example pyridine, pyrimidine, pyrazine, triazine, etc. Further 6-membered ring aryl or 6-membered ring heteroaryl groups may also be condensed onto these groups, such as, for example, in benzimidazole or quinoline.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy or 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkenyl, alkynyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, furthermore preferably F or CN, particularly preferably CN.

An aromatic or heteroaromatic ring system having 5-80 aromatic ring atoms, which may also in each case be substituted by the above-mentioned radicals and which may be linked via any desired positions on the aromatic or heteroaromatic group, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or transindenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combination of these systems. These groups may each be substituted by the above-mentioned radicals.

In a preferred embodiment of the invention, the radical $R^1$ which is bonded to the nitrogen atom stands for an aromatic or heteroaromatic ring system having 5 to 60 aromatic ring atoms, preferably having 6 to 24 aromatic ring atoms, which may also be substituted by one or more radicals $R^2$, or for a group of the above-mentioned formula (3) or (4).

In a further preferred embodiment of the compounds according to the invention, X stands for $C(R^1)_2$. In this case, the radicals $R^1$ which are bonded to this carbon atom preferably stand, identically or differently on each occurrence, for a straight-chain alkyl group having 1 to 10 C atoms or a branched or cyclic alkyl group having 3 to 10 C atoms, each of which may be substituted by one or more radicals $R^2$, where one or more non-adjacent $CH_2$ groups may be replaced by $R^2C=CR^2$, $C\equiv C$, $Si(R^2)_2$, $C=O$, $O$, $S$ or $CONR^2$ and where one or more H atoms may be replaced by D, F or CN, or for an aromatic or heteroaromatic ring system having 5 to 60, preferably having 5 to 24, aromatic ring atoms, which may also be substituted by one or more radicals $R^2$. The two radicals $R^1$ which are bonded to the same carbon atom may also form an aliphatic or aromatic ring system with one another.

In a further preferred embodiment of the invention, a maximum of one group Y per ring stands for N and the remaining groups Y stand, identically or differently on each occurrence, for CR. Y particularly preferably stands, identically or differently on each occurrence, for CR.

Preferred embodiments of the compounds of the formula (1) are therefore the compounds of the following formula (5),

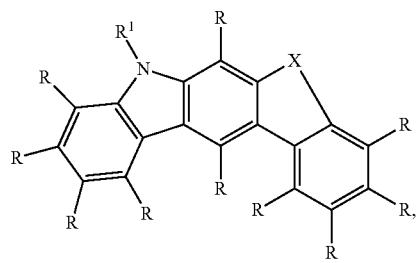

formula (5)

where the symbols used have the above-mentioned meanings, and, as described above, at least one of the groups of the formula (2) to (4) is present.

Particularly preferred embodiments of the structures of the formula (5) are the structures of the following formula (5a),

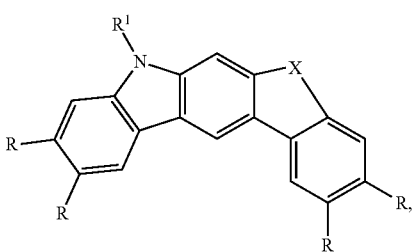

formula (5a)

where the symbols used have the above-mentioned meanings.

Particular preference is given to structures of the following formulae (6), (7) and (8),

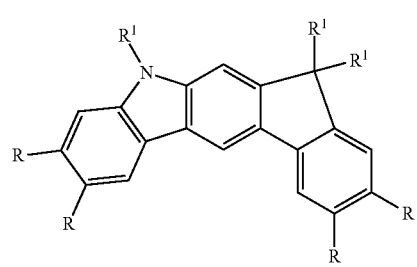

formula (6)

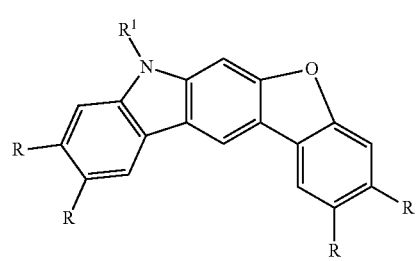

formula (7)

-continued

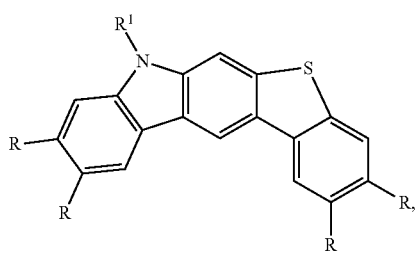
formula (8)

and very particular preference is given to the compounds of the following formulae (6a), (7a) and (8a),

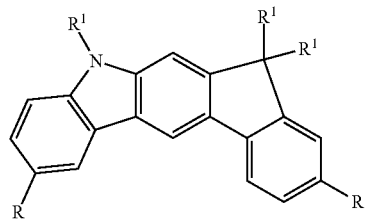
formula (6a)

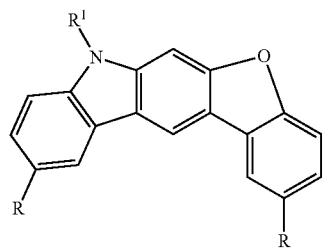
formula (7a)

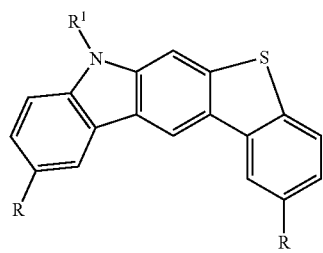
formula (8a)

where the symbols used have the above-mentioned meanings.

Especial preference is given to the compounds of the following formulae (6b), (7b) and (8b),

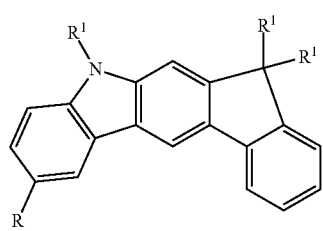
formula (6b)

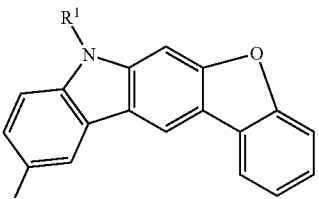
formula (7b)

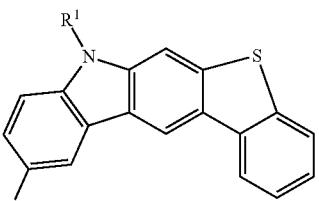
formula (8b)

where the symbols used have the above-mentioned meanings.

Two radicals $R^1$ here which are bonded to the same C atom in formula (6) or (6a) or (6b) may also form an aliphatic, aromatic or heteroaromatic ring system, for example a fluorene, together with the carbon atom to which they are bonded and thus overall form a spiro system.

Particular preference is given to indenocarbazole derivatives, i.e. the compounds of the formula (6) or (6a) or (6b).

As described above, the compound according to the invention contains at least one group R of the formula (2) and/or at least one group $R^1$ of the formula (3) or (4).

In a further preferred embodiment of the invention, the compound of the formula (1) contains one, two or three groups of one or more of the formulae (2) to (4), particularly preferably one or two groups of one or more of the formulae (2) to (4), very particularly preferably precisely one group of one of the formulae (2) to (4).

If the compound according to the invention contains a group of the formula (3) or (4), this group of the formula (3) or (4) is preferably bonded to the nitrogen atom of the compound, i.e. preferably not to the group X.

The preferred embodiments of the groups of the formulae (2) to (4) are described below.

In a preferred embodiment of the invention, a maximum of one group Q per ring in each of the groups of the formulae (2) to (4) stands for N and the remaining groups Q stand, identically or differently on each occurrence, for $CR^2$ or for C if the group $Ar^1$ or the remainder of the molecule is linked to this group. In a particularly preferred embodiment of the invention, Q stands for C if the group of the formula (2) or (3) is linked to $Ar^1$ or to the remainder of the molecule via this group, and the remaining groups Q stand, identically or differently, for $CR^2$, or in formula (4) all Q stand for $CR^2$.

Preferred embodiments of the formulae (2) to (4) are therefore the groups of the following formulae (2a) to (4a),

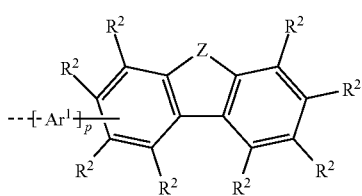
formula (2a)

formula (3a)

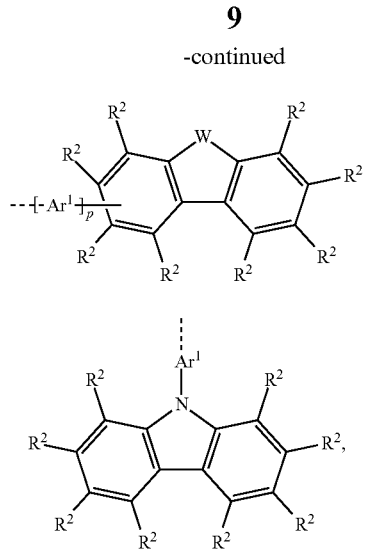

formula (4a)

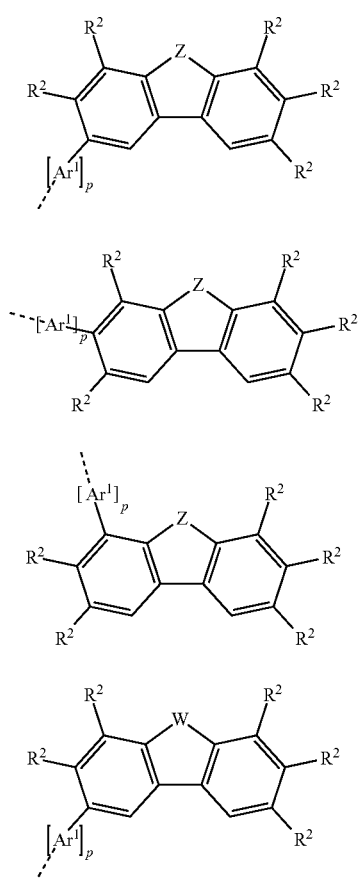

where the dashed bond indicates the linking of the group to the remainder of the molecule, and the symbols and indices used have the above-mentioned meanings, and, in formula (2a) and (3a), no group $R^2$ is bonded at the position at which the group $Ar^1$ or the remainder of the molecule is linked.

Particularly preferred embodiments of the formulae (2a) to (4a) are the structures of the formulae (2b), (2c), (2d), (3b), (3c), (3d) and (4b),

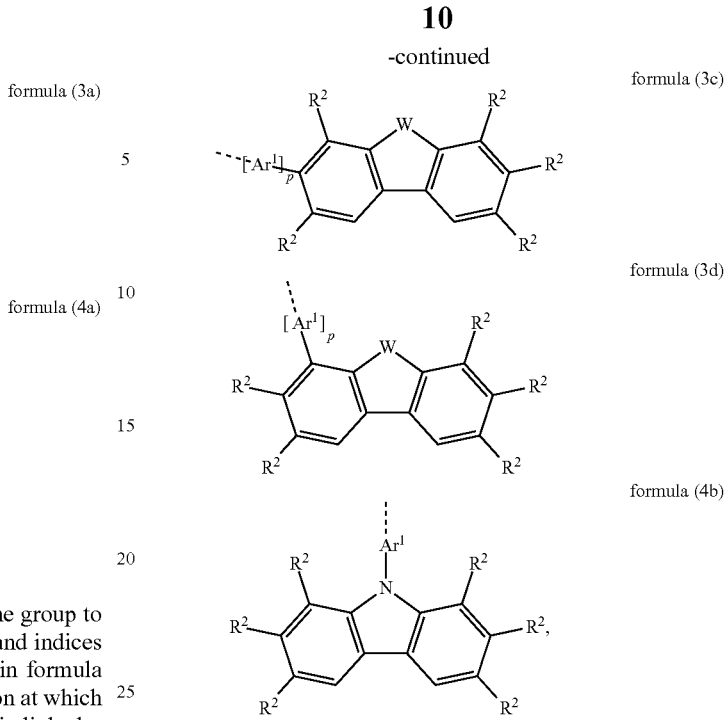

where the dashed bond indicates the linking of the group to the remainder of the molecule, and the other symbols and indices used have the above-mentioned meanings.

In the above-mentioned structures, Z and W preferably stands for $NR^2$, where $R^2$ stands for an aromatic or heteroaromatic ring system in accordance with the above-mentioned definition, which may also be substituted by the above-mentioned radicals.

Furthermore, the radicals $R^2$ which are bonded to a carbon atom in the above-mentioned structures preferably stand for H.

In a further preferred embodiment of the invention, the index p=0.

Particular preference is given to the structures of the formulae (2b), (3b) and (4b).

If a group $Ar^1$ is present, this preferably stands for a divalent aromatic or heteroaromatic ring system having 6 to 24 aromatic ring atoms, which preferably contains no condensed aryl or heteroaryl group having more than two six-membered rings condensed directly onto one another. Preferred groups $Ar^1$ are selected from the group consisting of ortho-, meta- or para-benzene, ortho-, meta- or para-biphenyl, terphenyl, in particular ortho-, meta- or para-terphenyl, quaterphenyl, in particular ortho-, meta- or para-quaterphenyl, fluorene, furan, benzofuran, dibenzofuran, dibenzothiophene, pyrrole, indole or carbazole. These groups may be substituted by one or more radicals $R^2$, but are preferably unsubstituted. If $Ar^1$ stands for fluorene, this is preferably substituted in the 9-position by two alkyl groups, each having 1 to 10 C atoms.

The above-mentioned embodiments of the invention can be combined with one another as desired. In particular, the above-mentioned general formulae (1) or the preferred embodiments can be combined as desired with the formulae (2) to (4) or the corresponding preferred embodiments and with the above-mentioned preferred embodiments of the other symbols and indices as desired. In a preferred embodiment of the invention, the above-mentioned preferences occur simultaneously. Thus, in particular, it is possible to combine each of the formulae (5), (5a), (6), (6a), (6b), (7), (7a), (7b), (8), (8a) and (8b) with each of the formulae (2a), (2b), (2c), (2d), (3a), (3b), (3c), (3d), (4a) and (4b).

If one or more radicals R which are not equal to H or D and do not stand for a group of the formula (2) or (3) are present in the compound of the general formula (1), these radicals are preferably selected from the group consisting of $N(Ar)_2$, preferably diphenylamino, a substituted or unsubstituted arylamine, a straight-chain alkyl group having 1 to 20 C atoms, preferably 1 to 10 C atoms, a branched alkyl group having 3 to 20 C atoms, preferably 1 to 10 C atoms, or an aromatic or heteroaromatic ring system having 5 to 40 aromatic ring atoms, which may be substituted by one or more radicals $R^2$. The aromatic or heteroaromatic ring system here is preferably selected from substituted or unsubstituted phenyl, naphthyl, thiophene, dibenzothiophene, dibenzofuran triphenylamine or combinations of these groups, each of which may be substituted by one or more radicals $R^2$.

In a further preferred embodiment of the invention, X in formula (1) stands for $C(R^1)_2$, where the radicals $R^1$ form a ring system with one another, so that a structure of the following formula (9) or (10) forms:

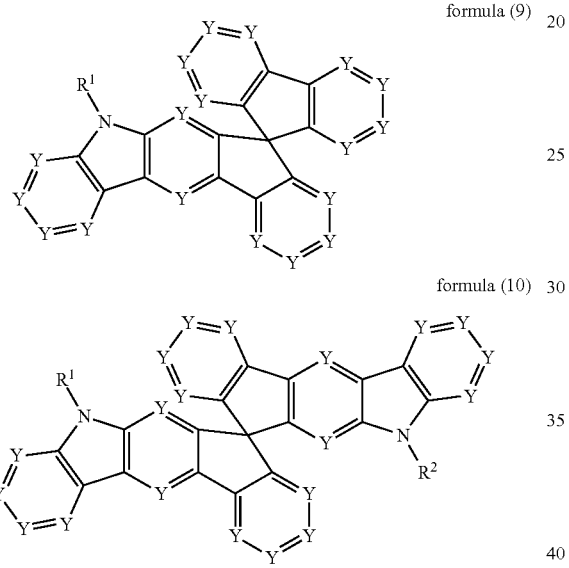

where the symbols used have the above-mentioned meanings, and Y preferably stands, identically or differently on each occurrence, for $CR^1$.

In still a further preferred embodiment of the invention, two adjacent radicals R on the basic structure of the formula (1) form an aromatic ring system, so that a structure of the following formula (11) or (12) forms:

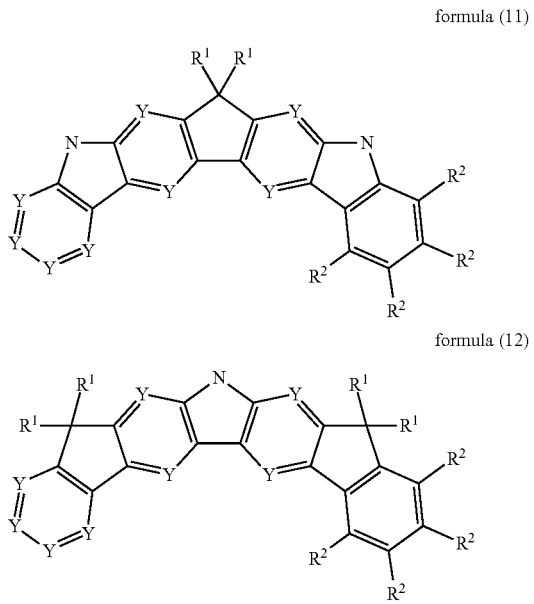

where the symbols used have the above-mentioned meanings, and Y preferably stands, identically or differently on each occurrence, for $CR^1$.

The same preferences as described above apply to the compounds of the formulae (9) to (12).

Examples of compounds according to the invention are the structures shown below.

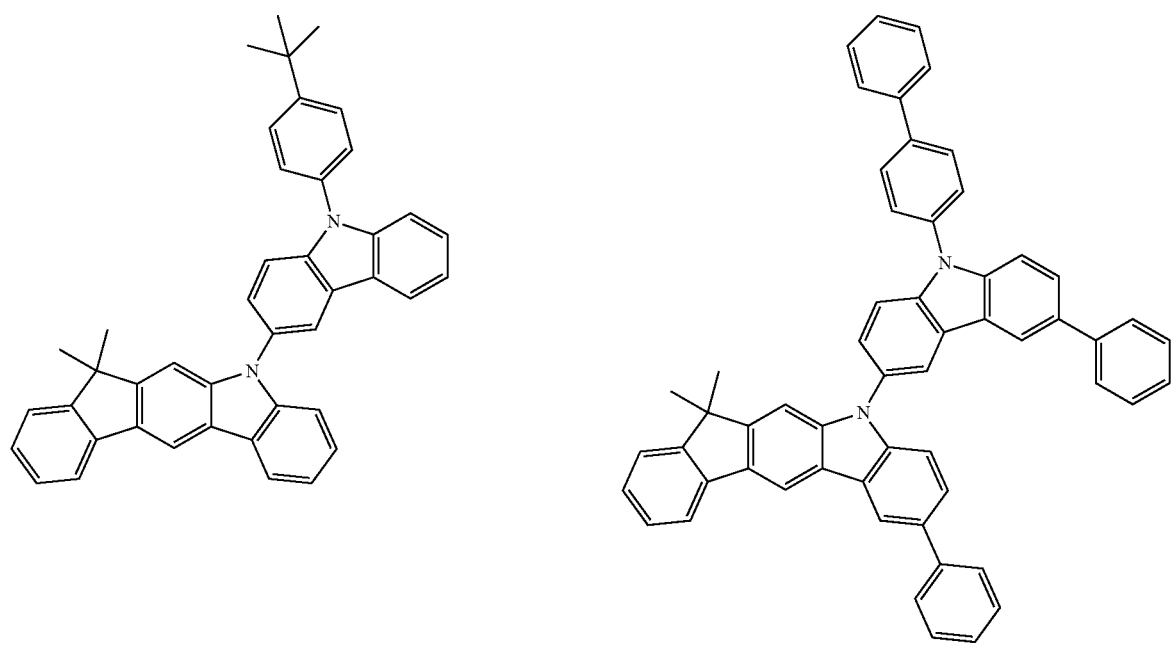

-continued
(3)
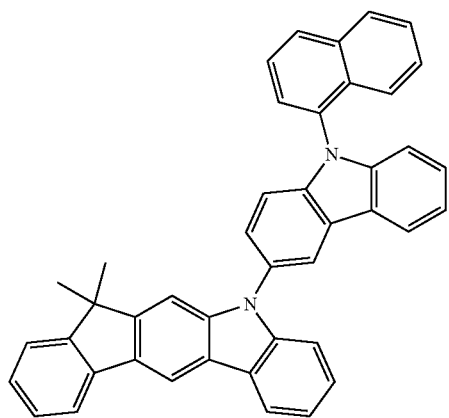
(4)
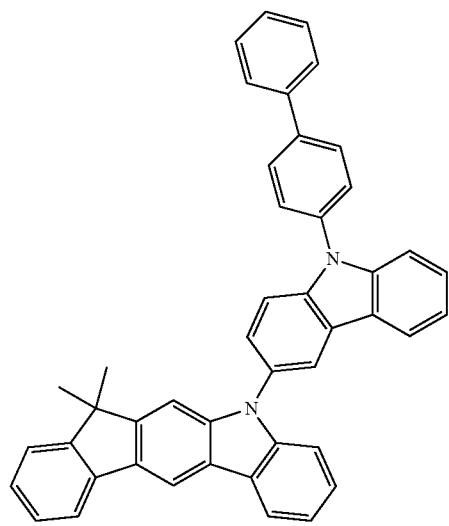
(5)
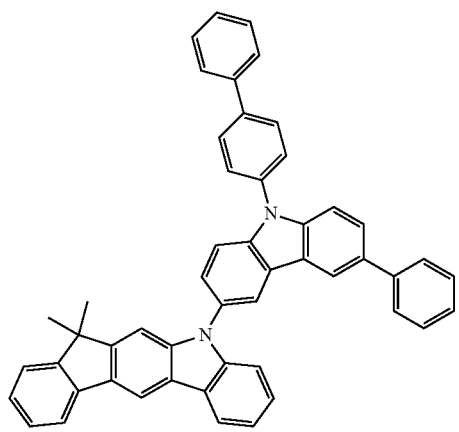
(6)
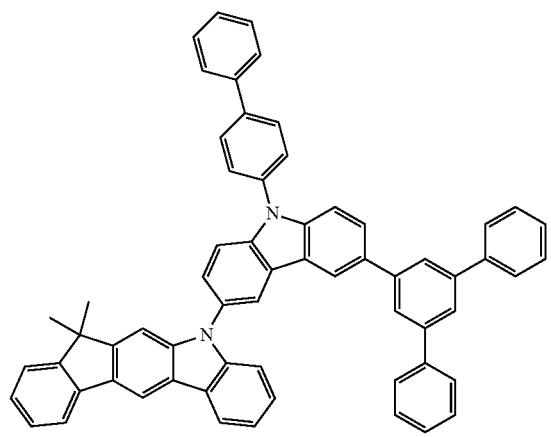
(7)
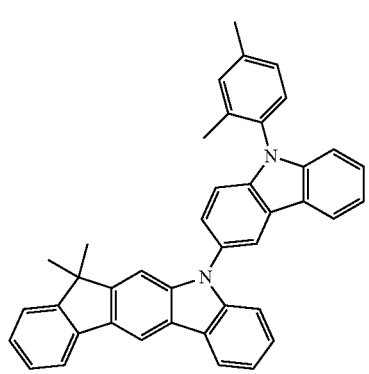
(8)
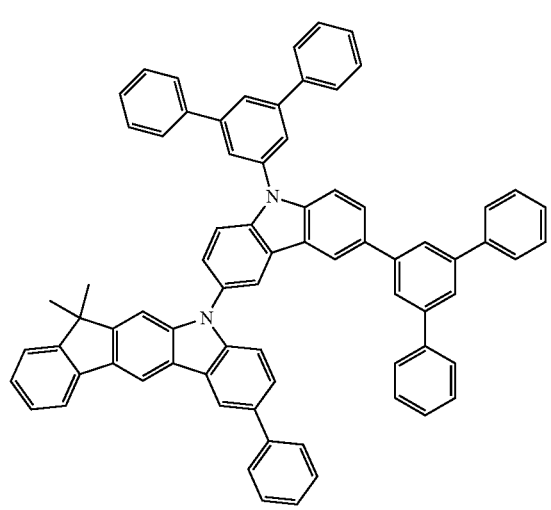

-continued
(9)
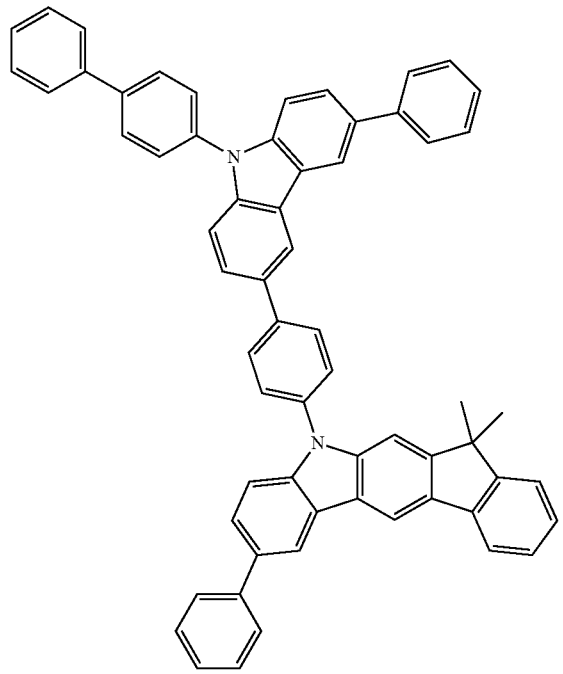
(10)
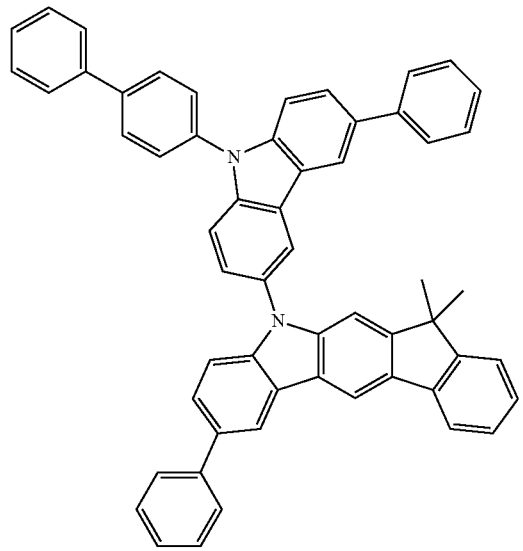
(11)
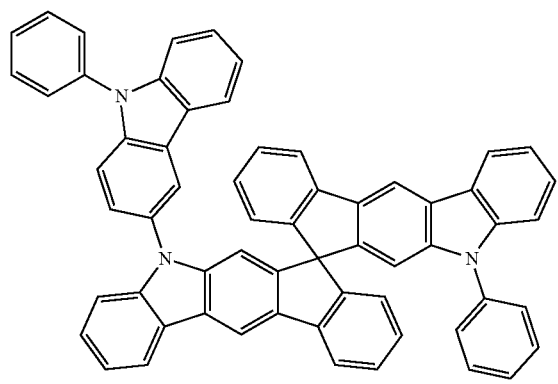
(12)
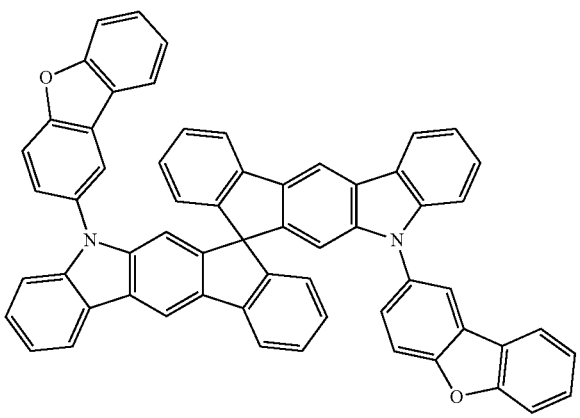
(13)
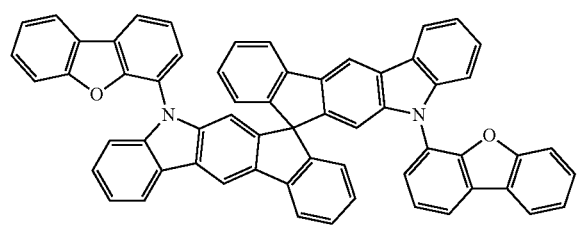
(14)
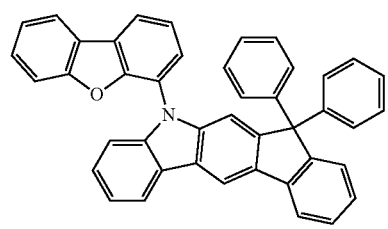

-continued
(15)
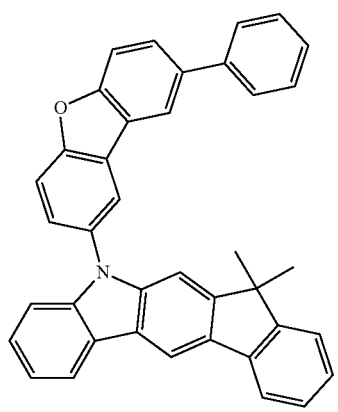
(16)
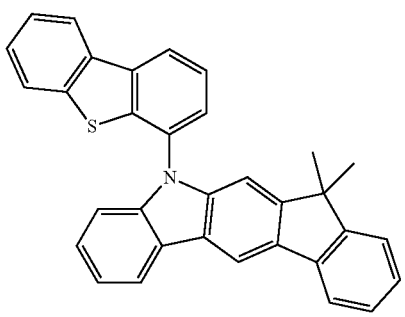
(17)
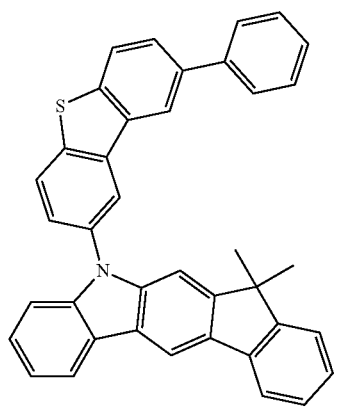
(18)
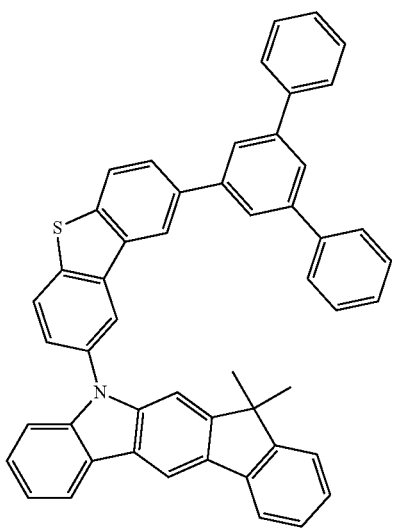
(19)
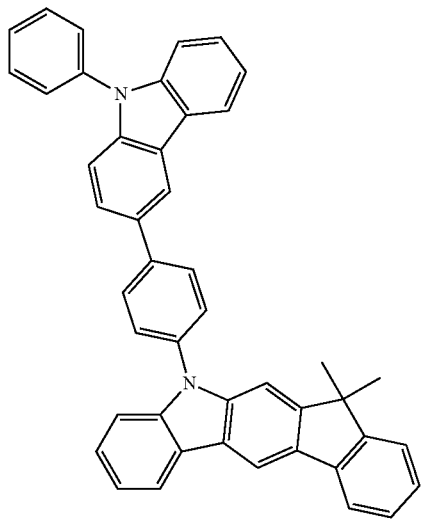
(20)
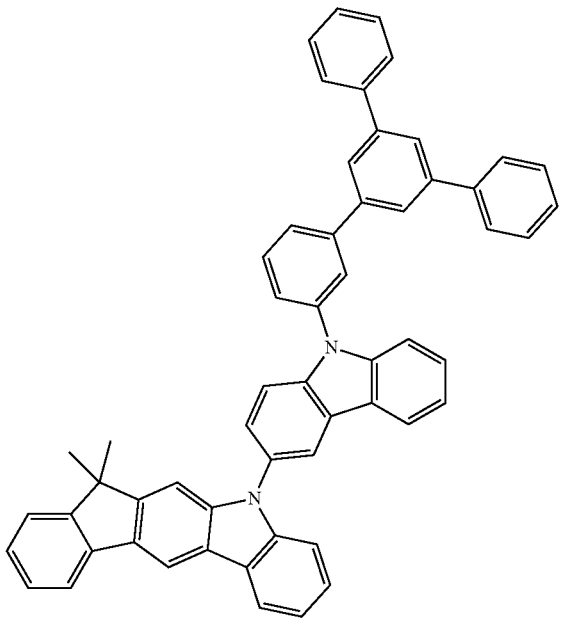

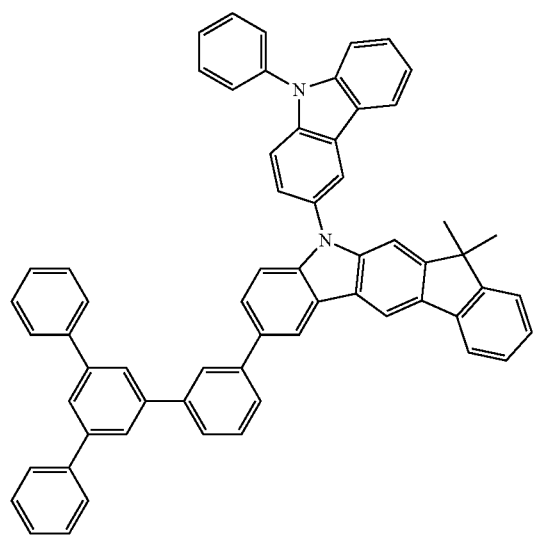
(21)
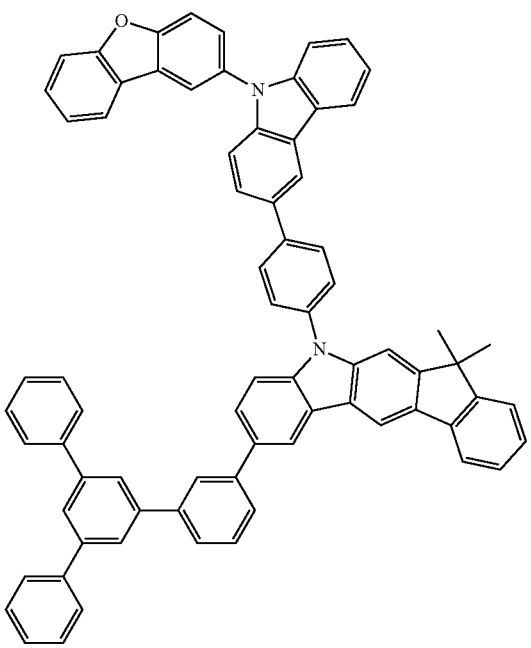
(22)
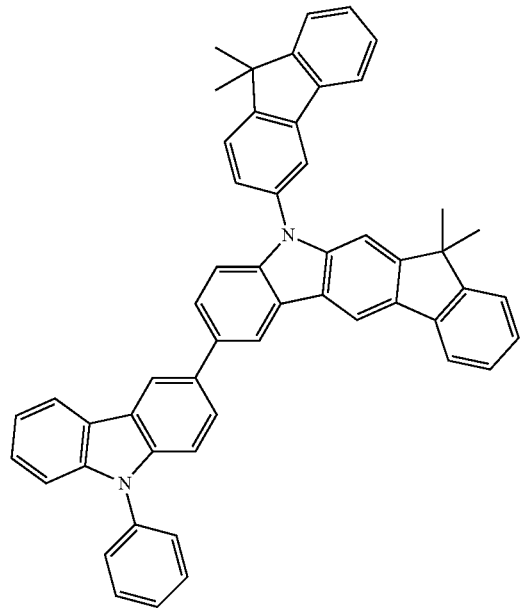
(23)
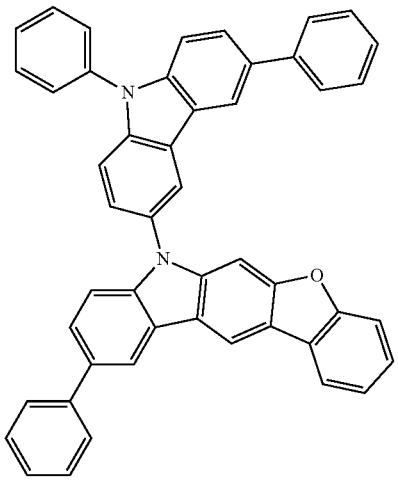
(24)

-continued
(25)
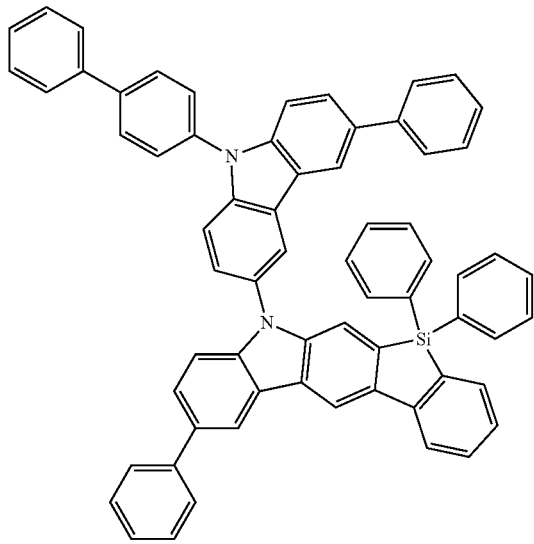
(26)
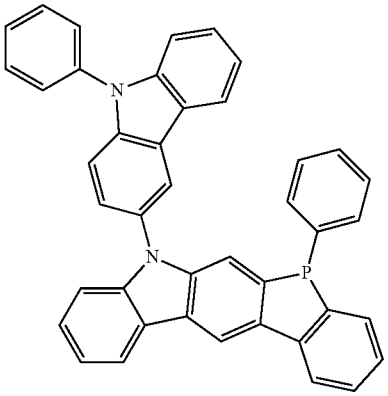
(27)
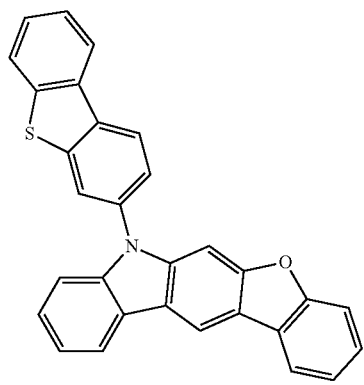
(28)
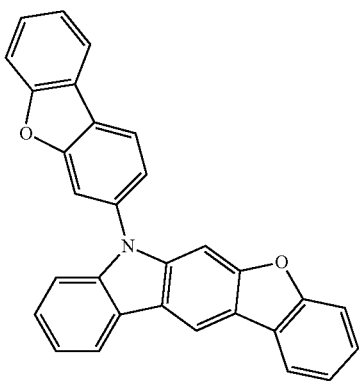
(29)
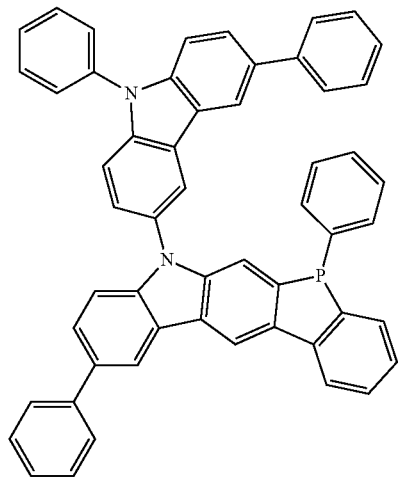
(30)
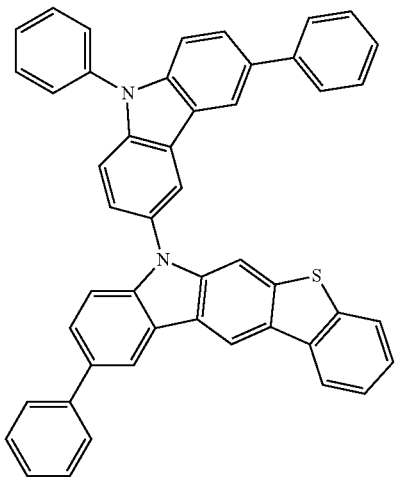

-continued
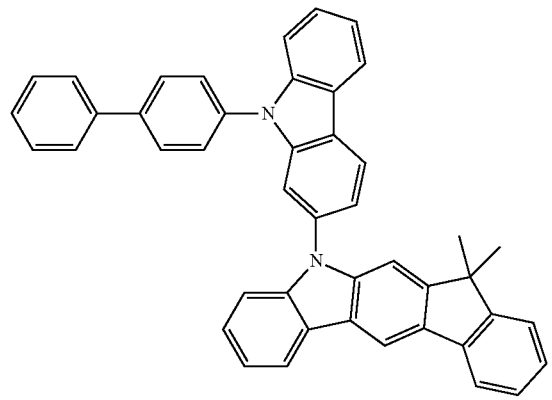
(31)
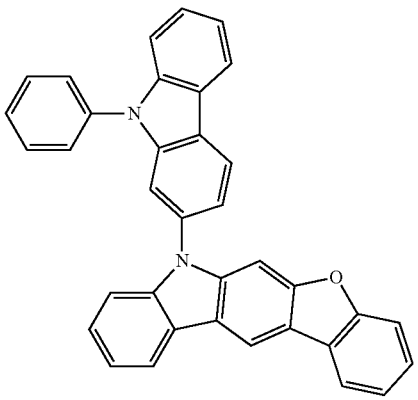
(32)
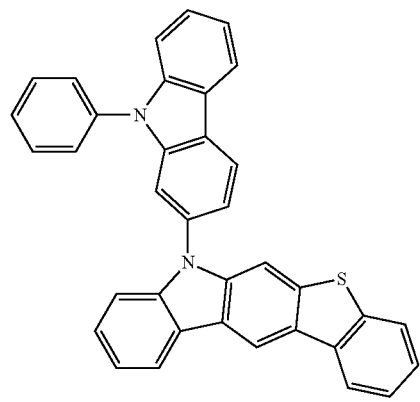
(33)
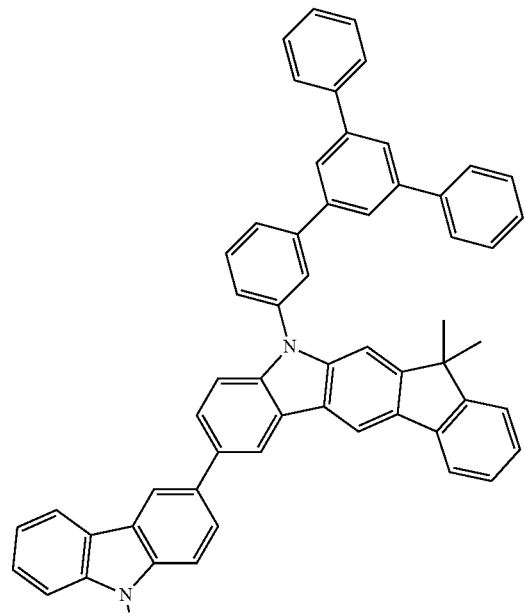
(34)

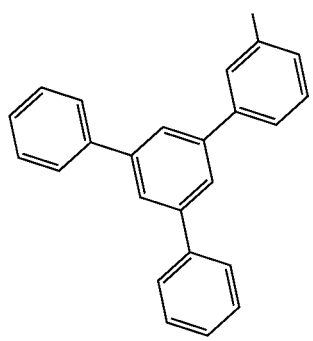
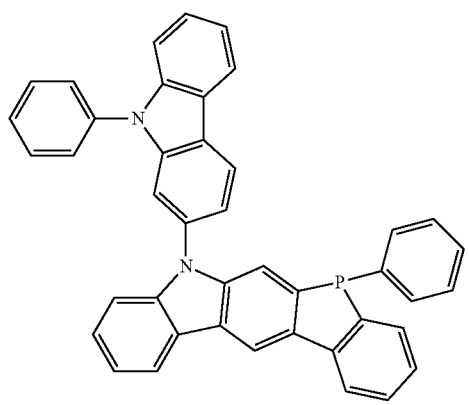
(35)
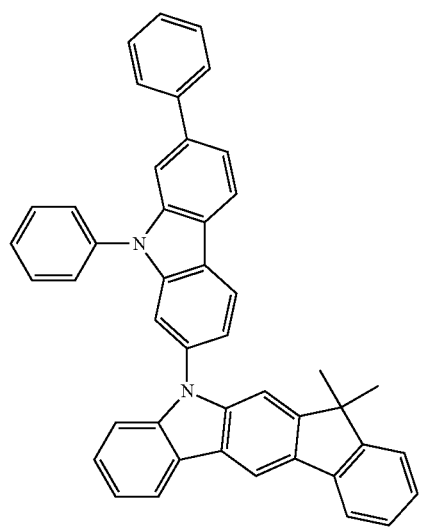
(36)
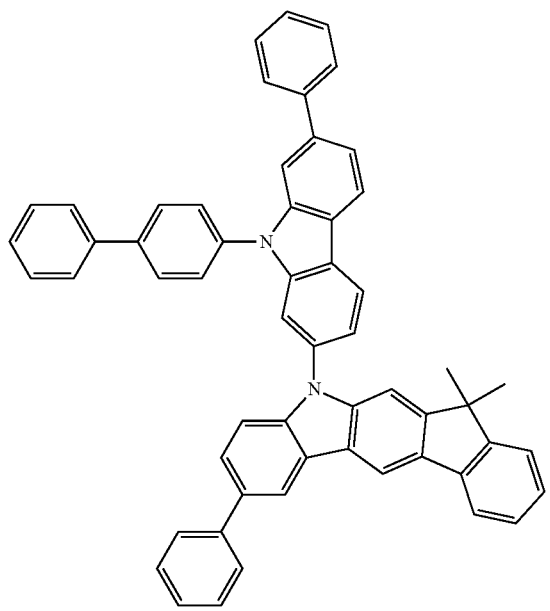
(37)
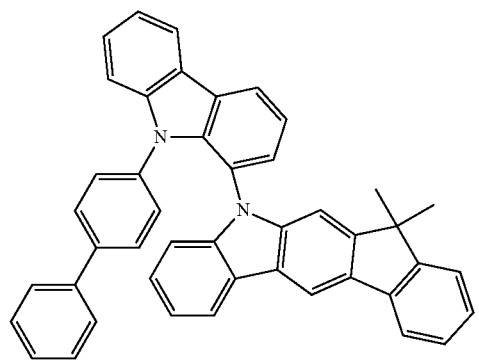
(38)

-continued
(39)
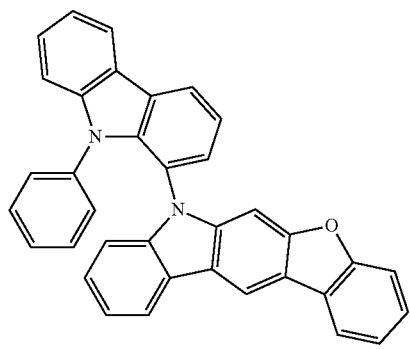
(40)
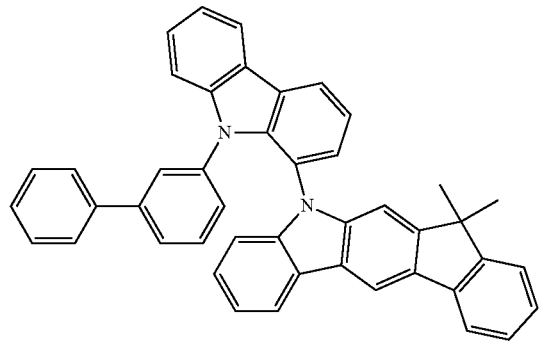
(41)
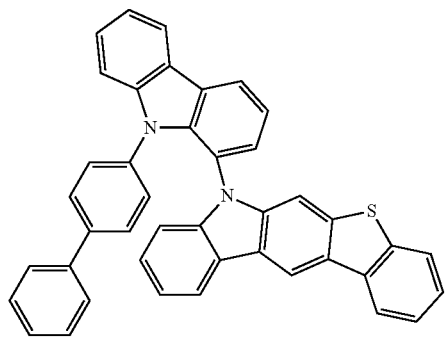
(42)
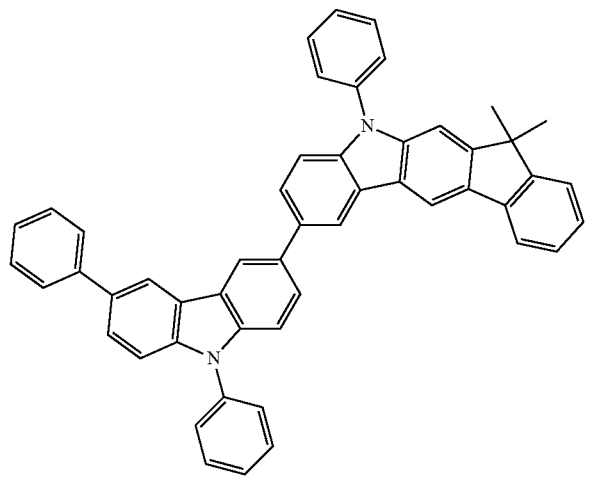
(43)
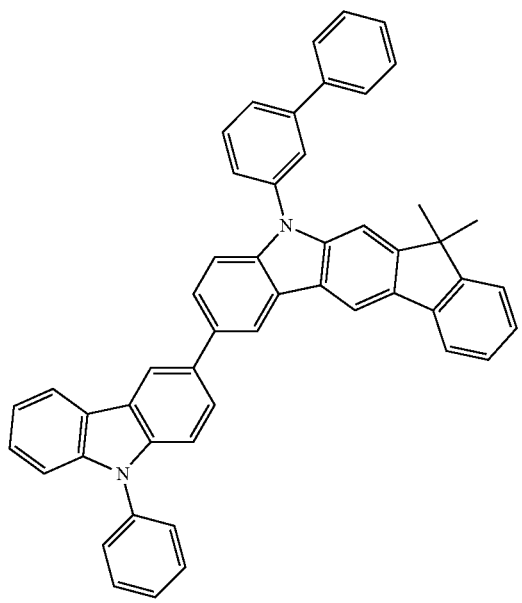
(44)
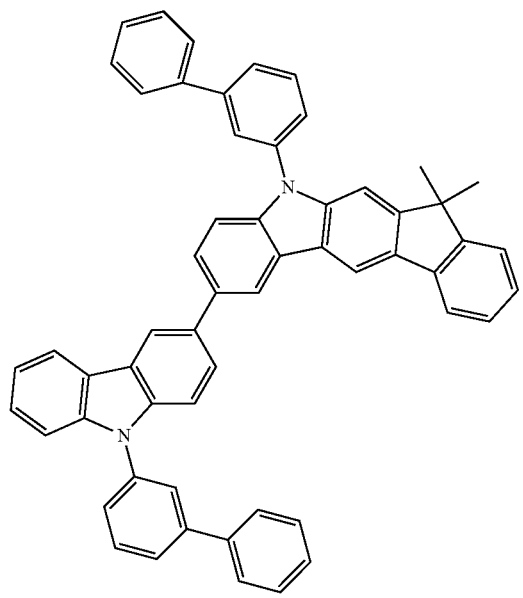

(45)
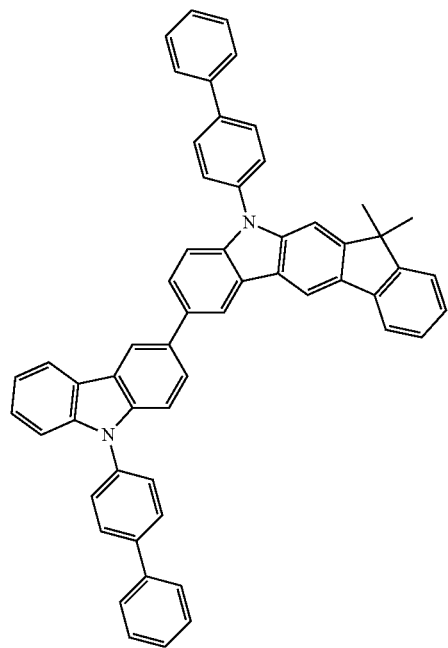
(46)
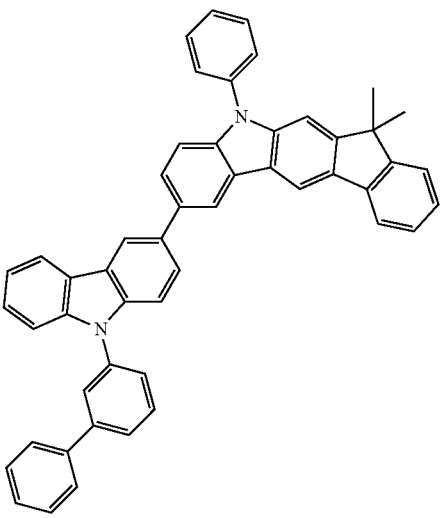
(47)
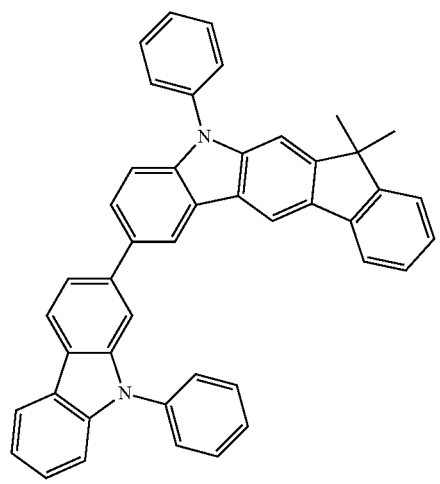
(48)
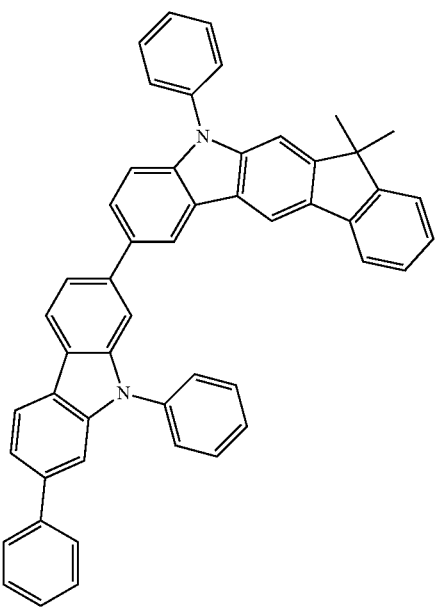

-continued
(49)
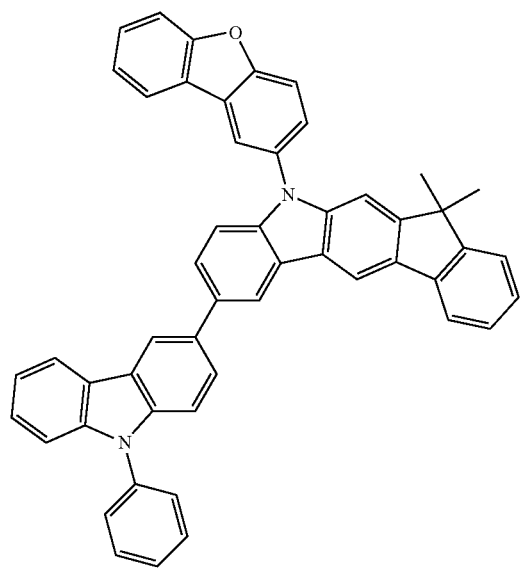
(50)
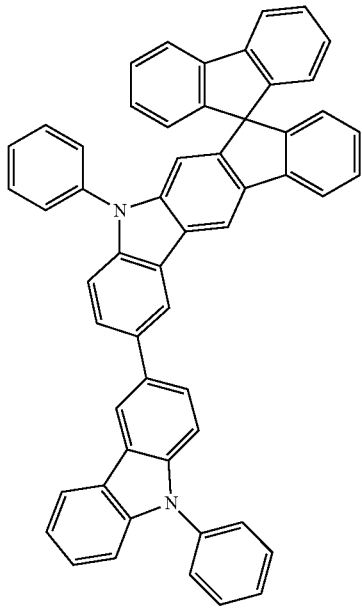
(51)
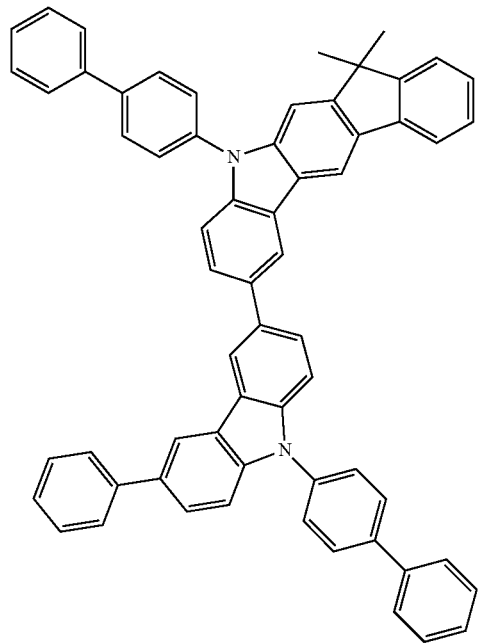
(52)
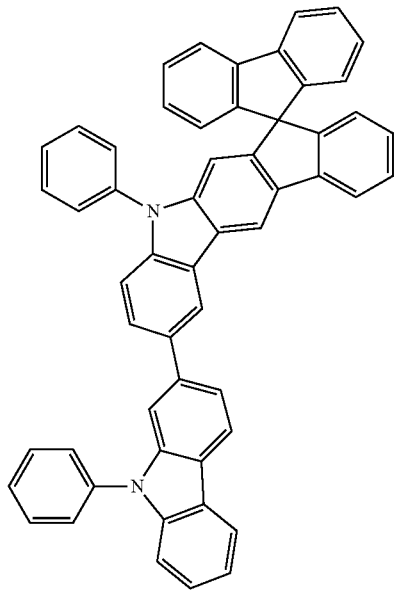

-continued
(53)
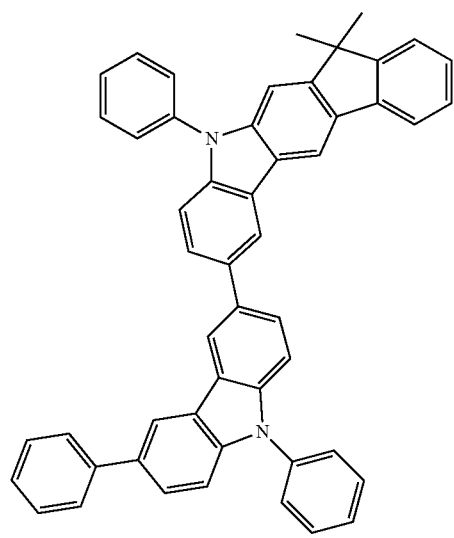
(54)
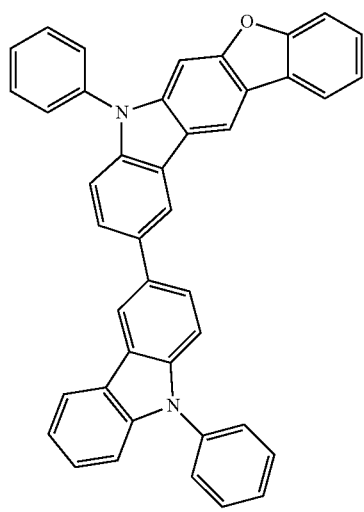
(55)
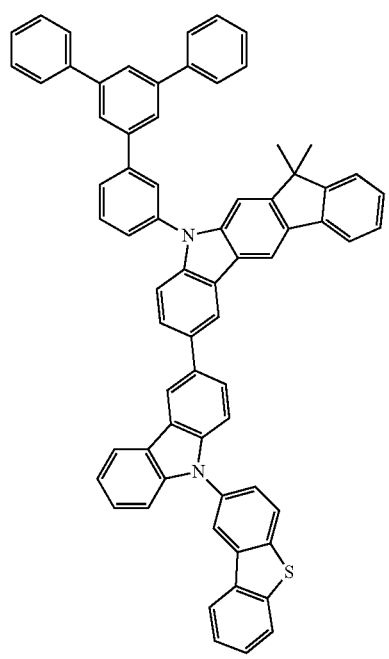
(56)
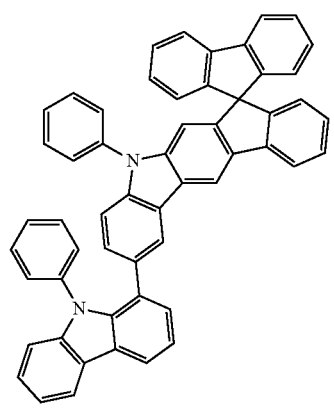

-continued
(57)
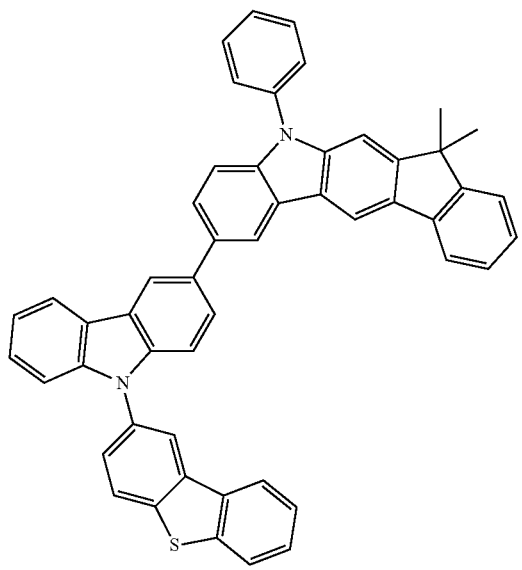
(58)
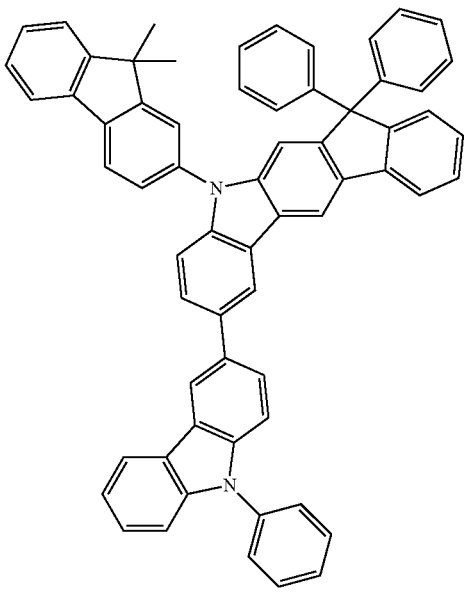
(59)
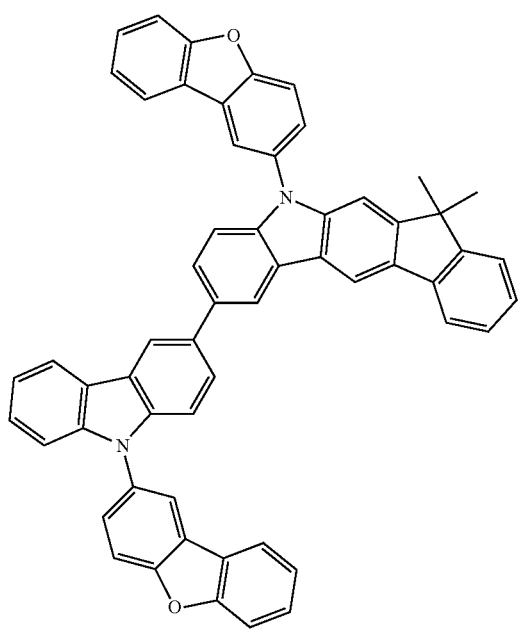
(60)
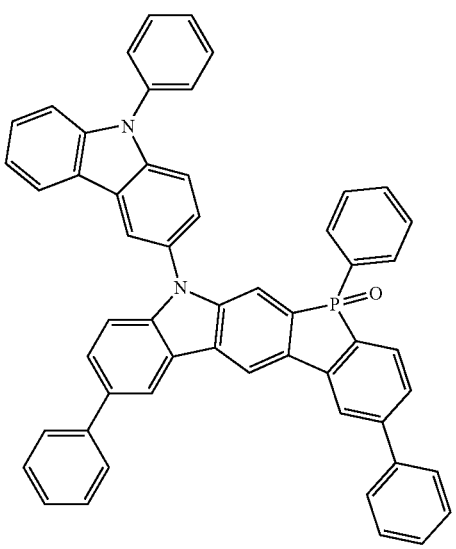

-continued
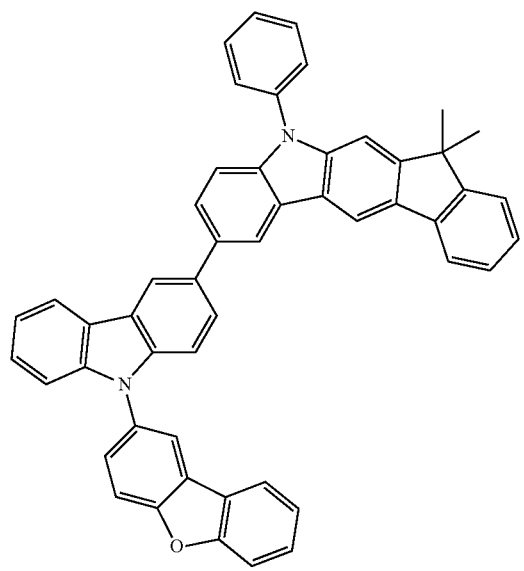
(61)
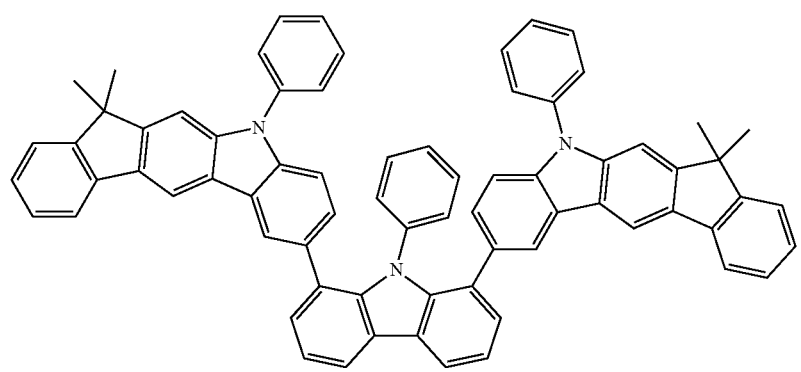
(62)
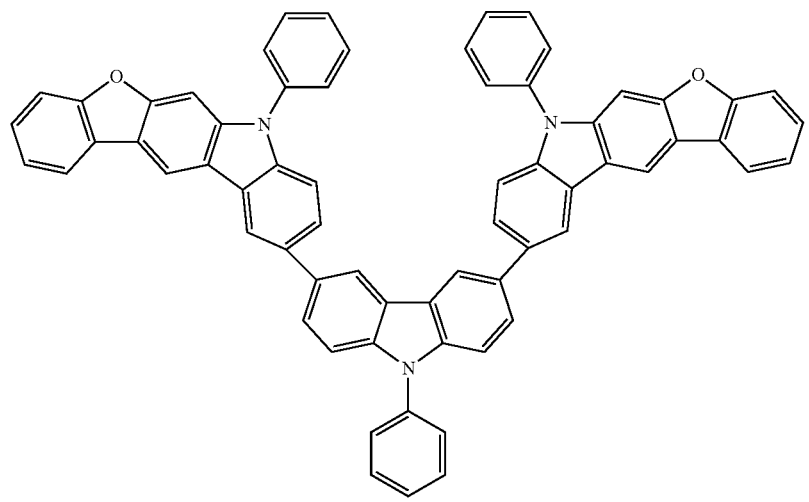
(63)

(64)
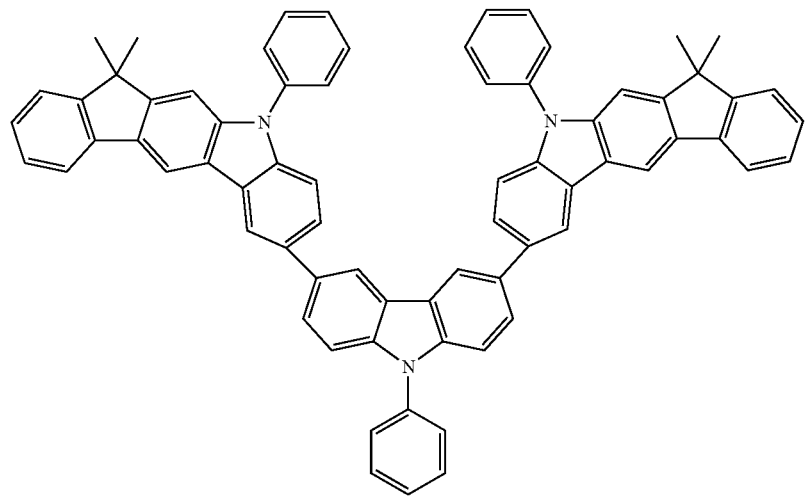
(65)
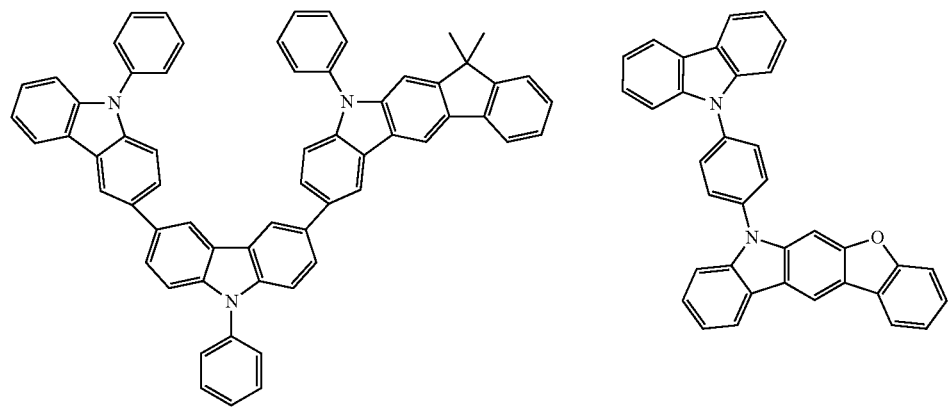
(66)
(67)
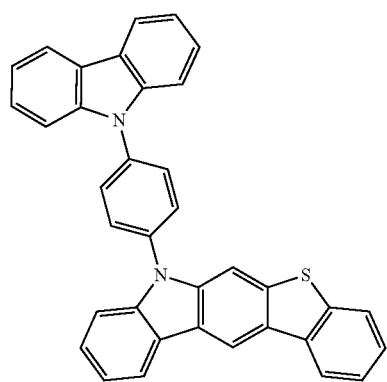
(68)
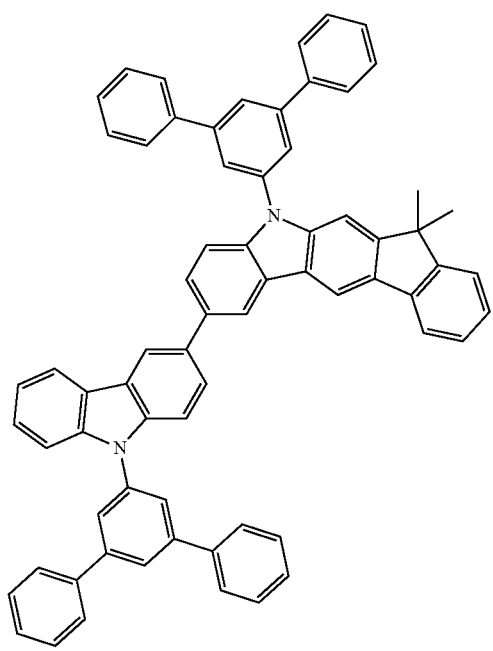

-continued
(69)
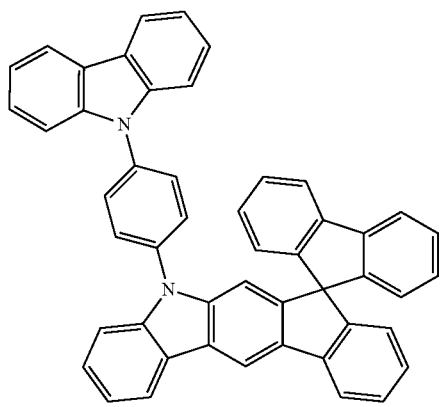
(70)
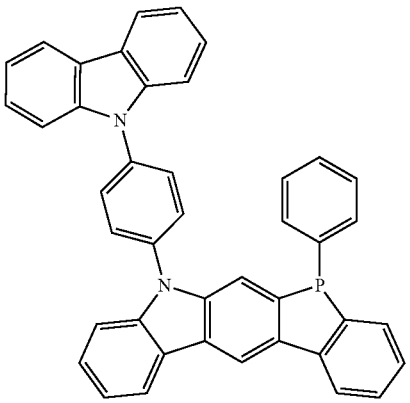
(71)
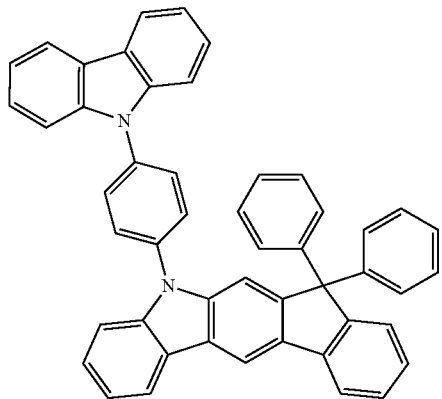
(72)
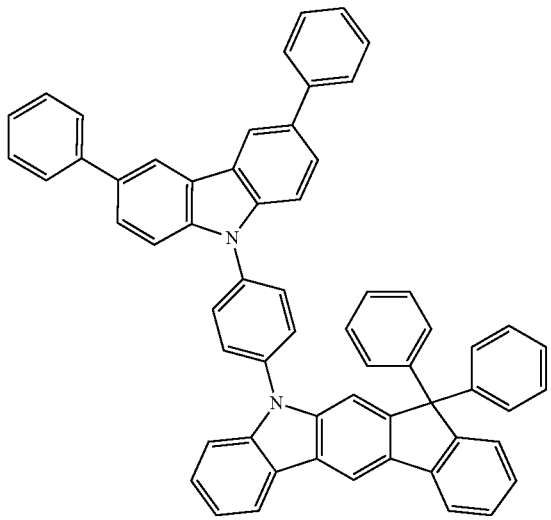
(73)
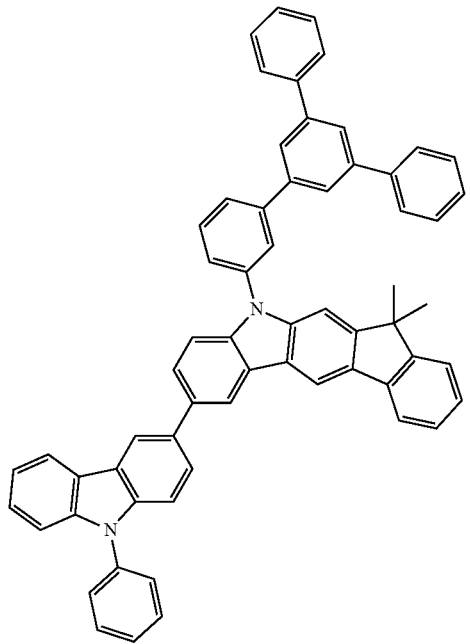
(74)
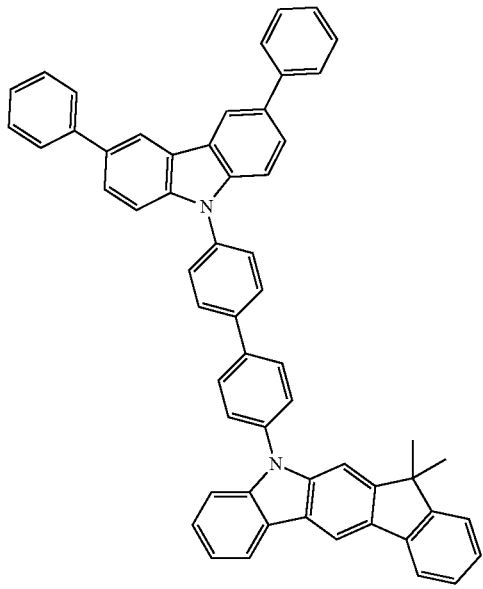

(75)
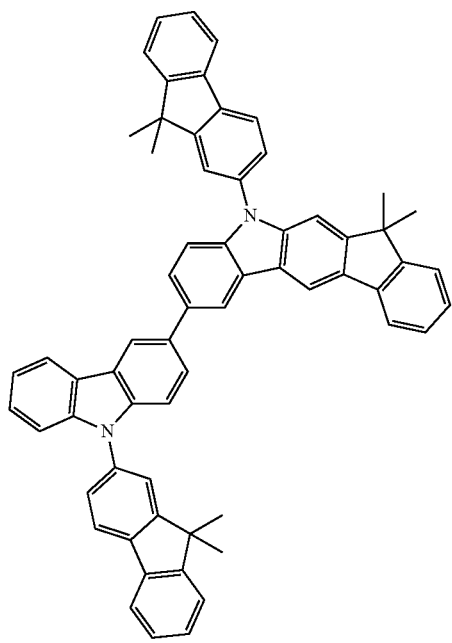
(76)
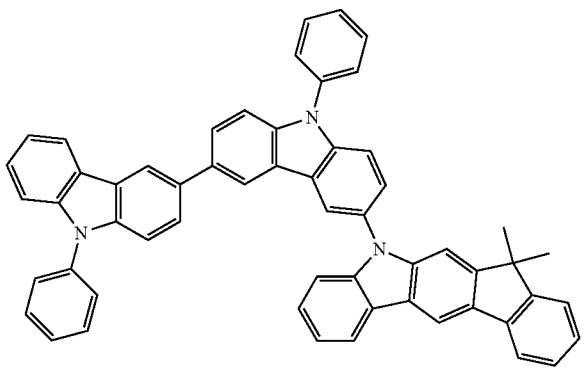
(77)
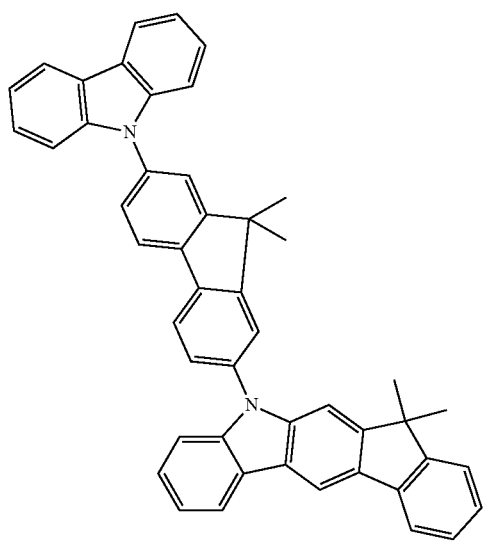
(78)
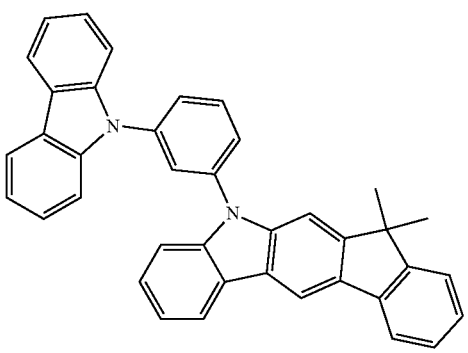

-continued
(79)
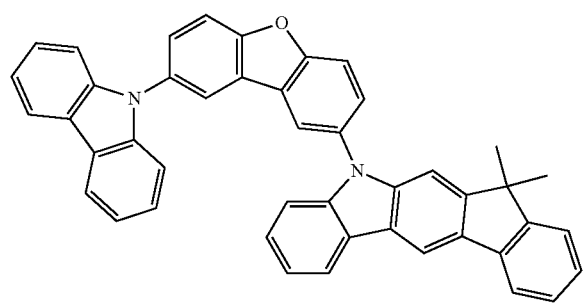
(80)
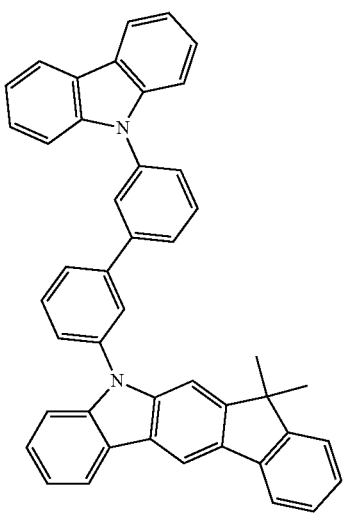
(81)
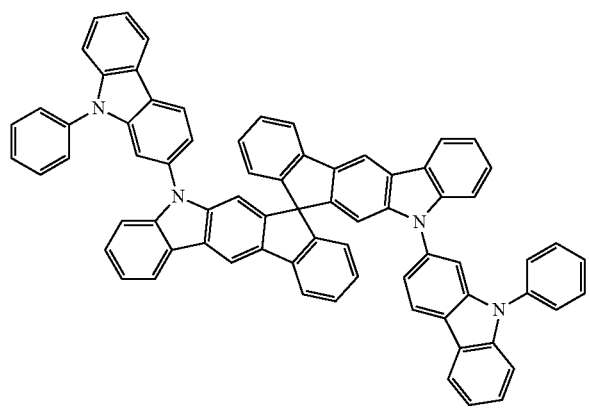
(82)
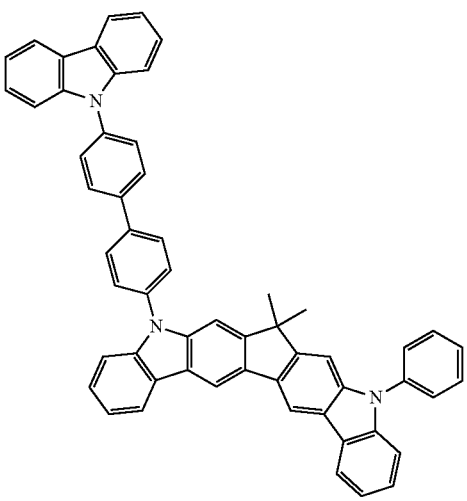
(83)
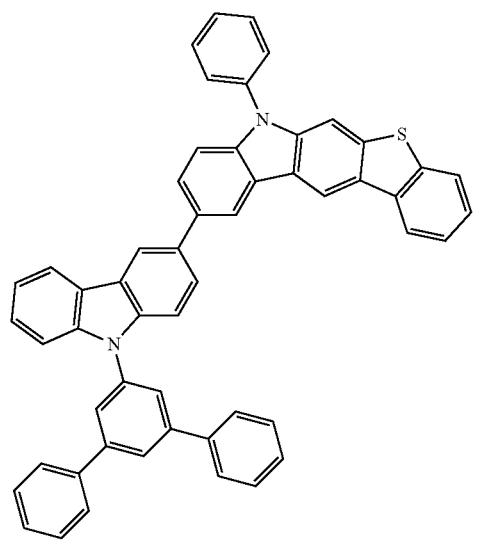
(84)
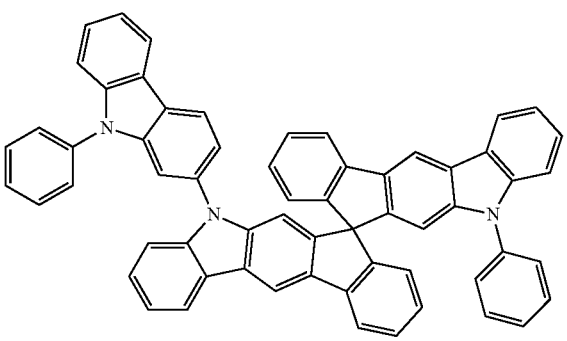

(85)
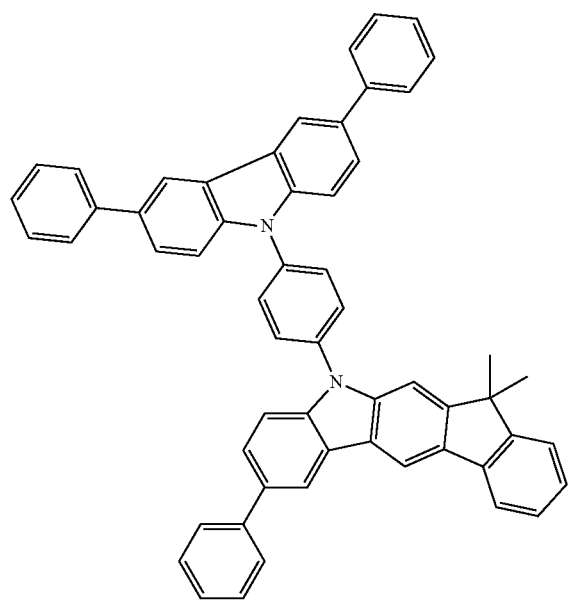
(86)
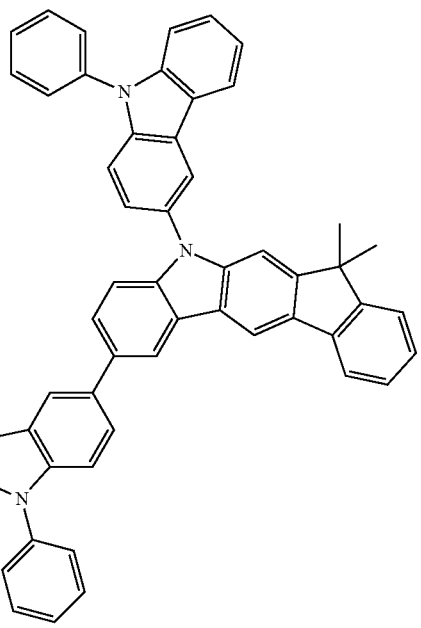
(87)
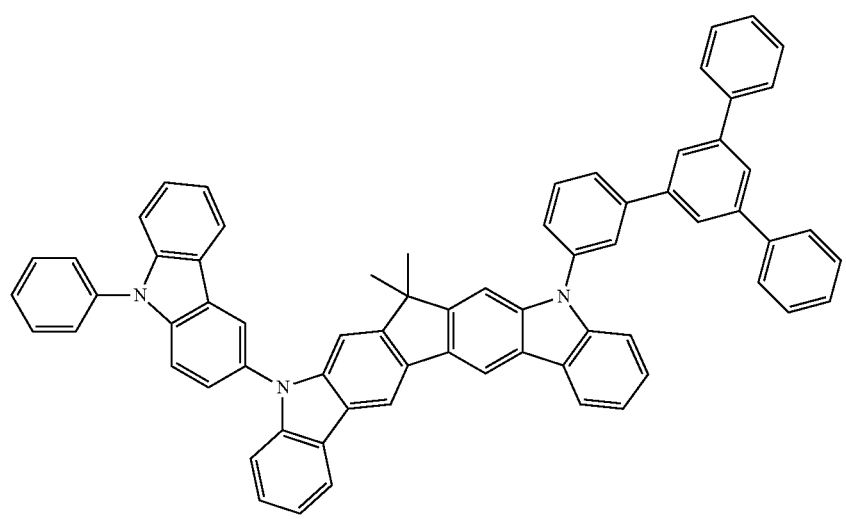
(88)
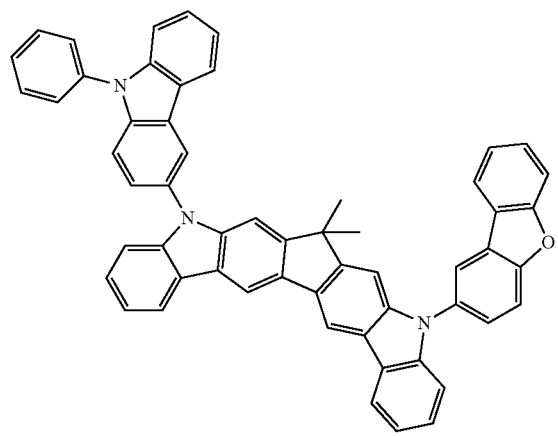
(89)
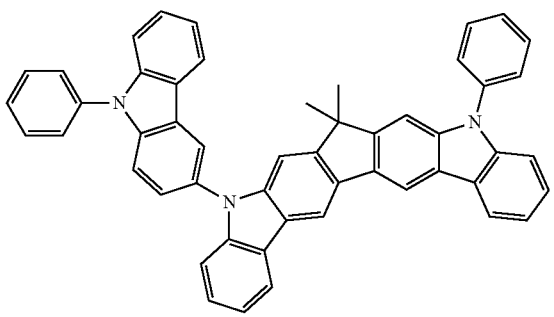

(90)
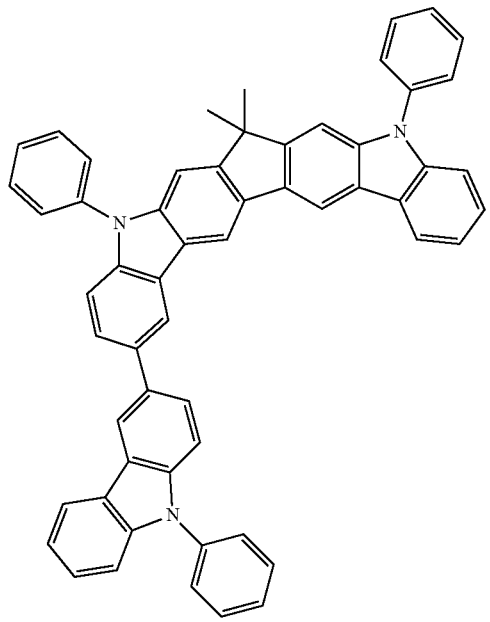
(91)
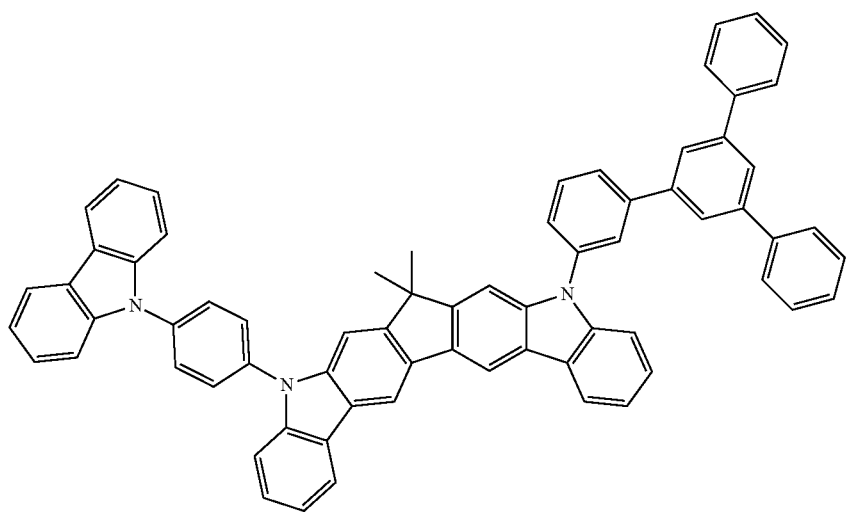
(92)
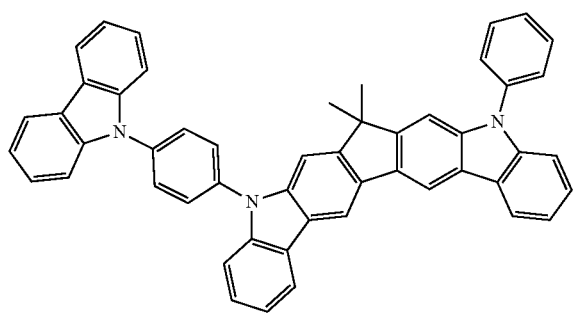
(93)
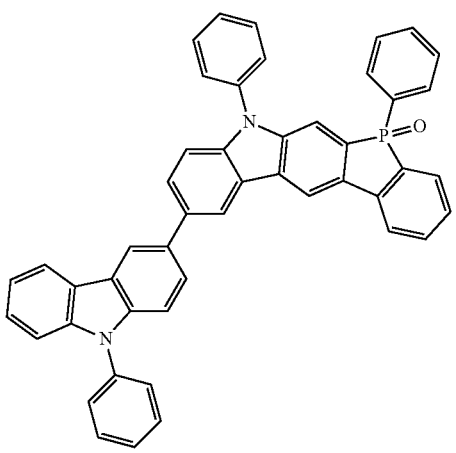

-continued
(94)
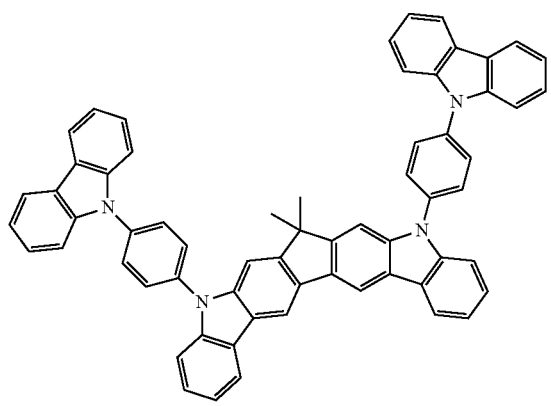
(95)
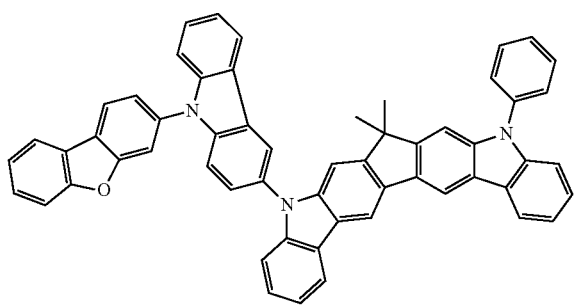
(96)
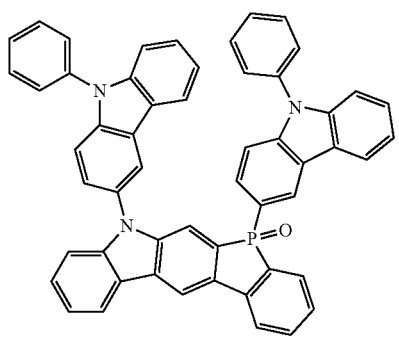
(97)
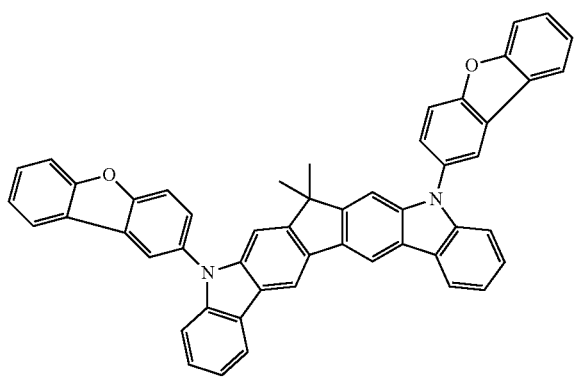
(98)
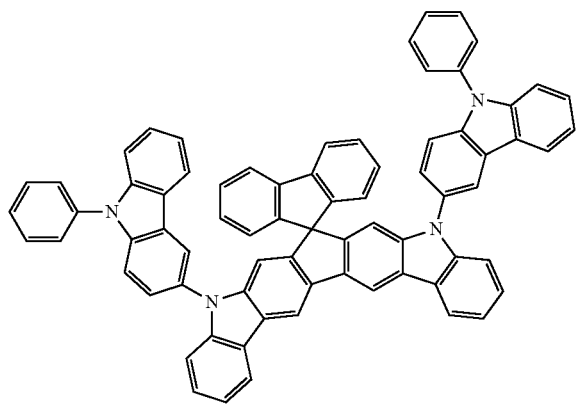
(99)
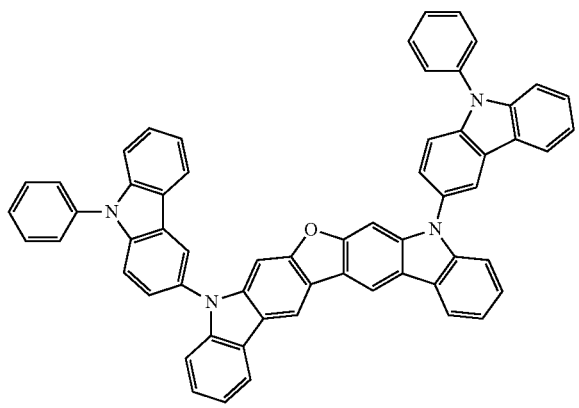

-continued
(98)
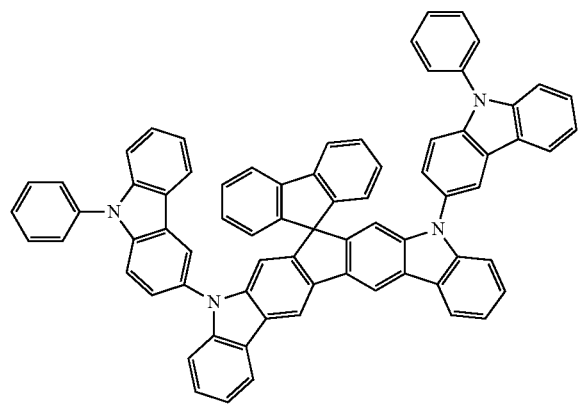
(99)
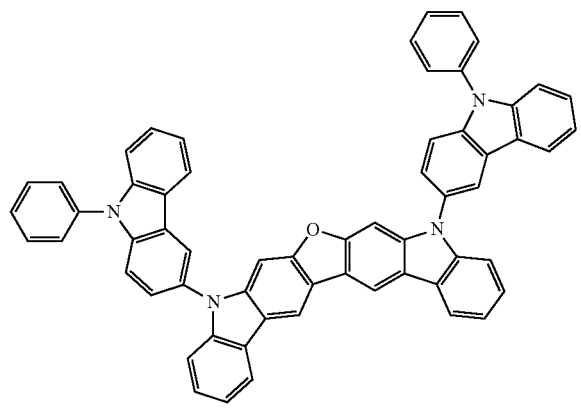
(100)
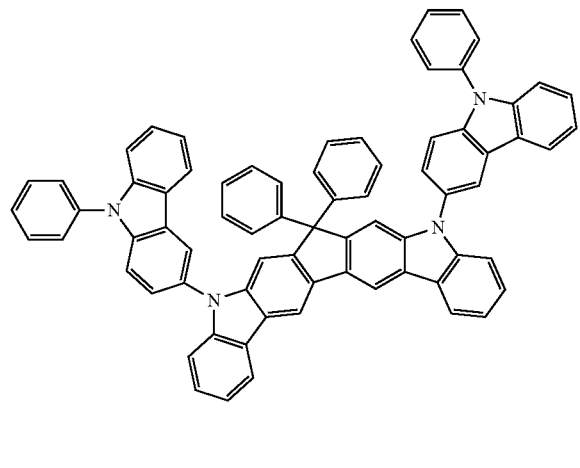
(101)
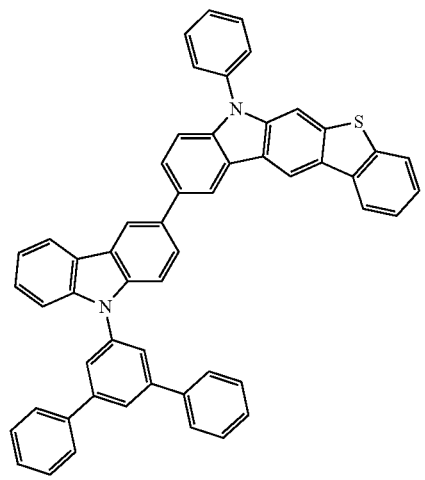
(102)
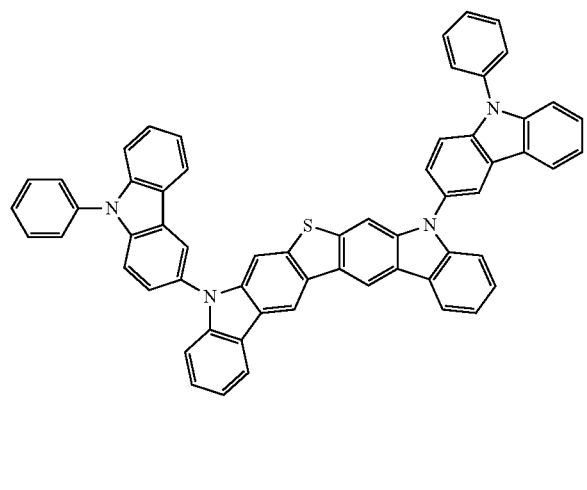
(103)
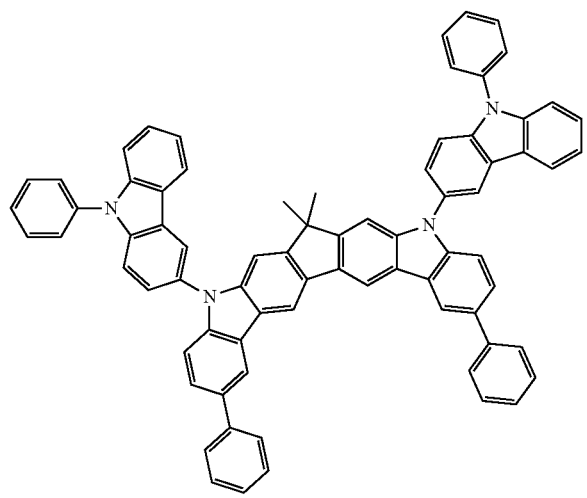

-continued
(104)
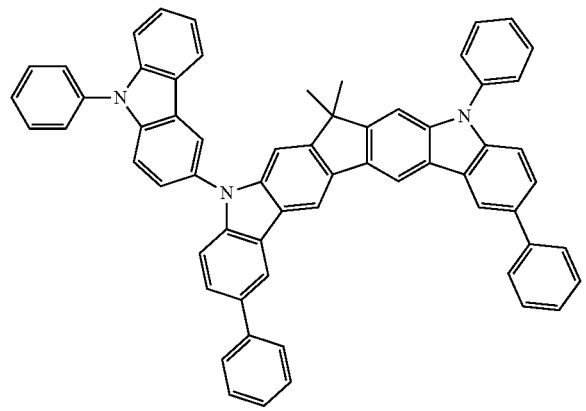
(105)
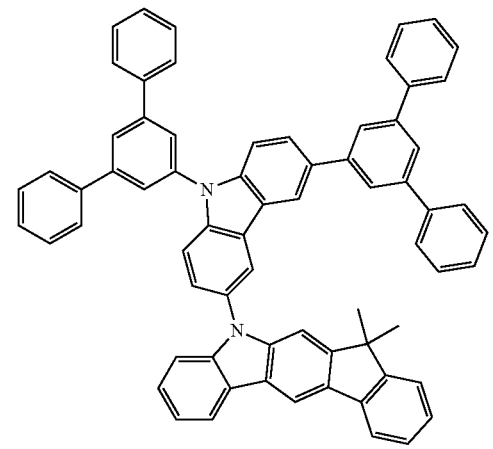
(106)
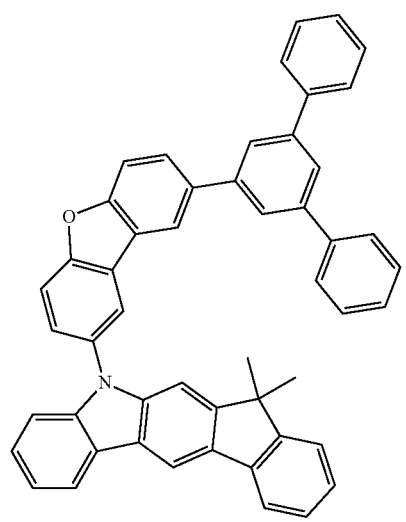
(107)
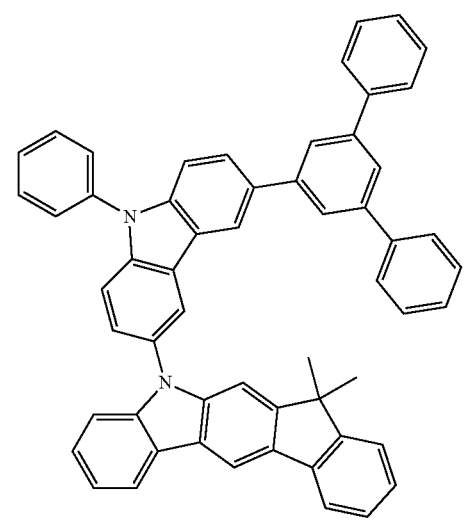
(108)
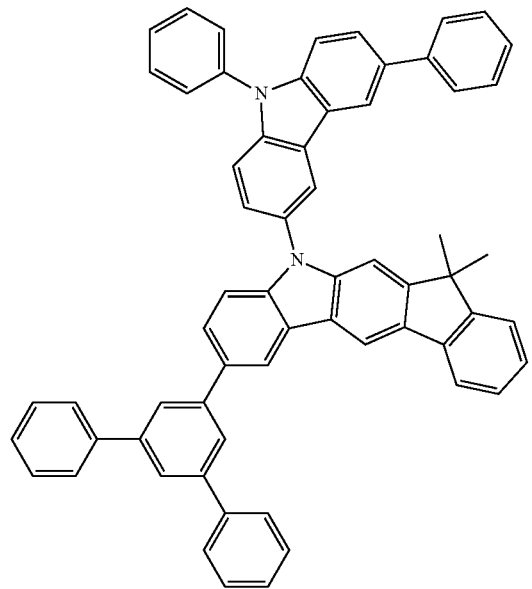
(109)
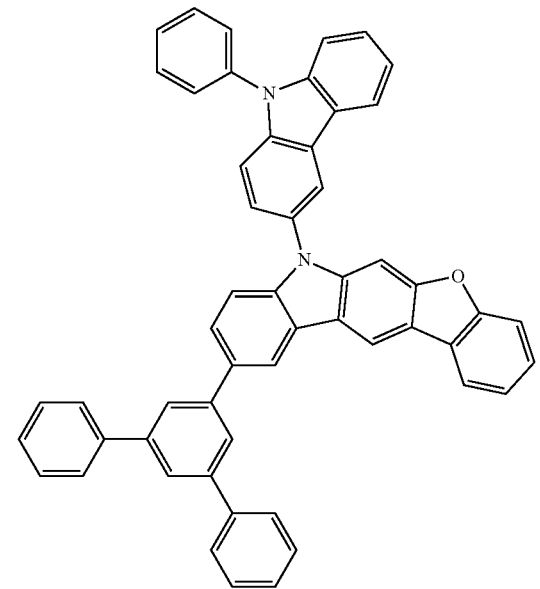

-continued

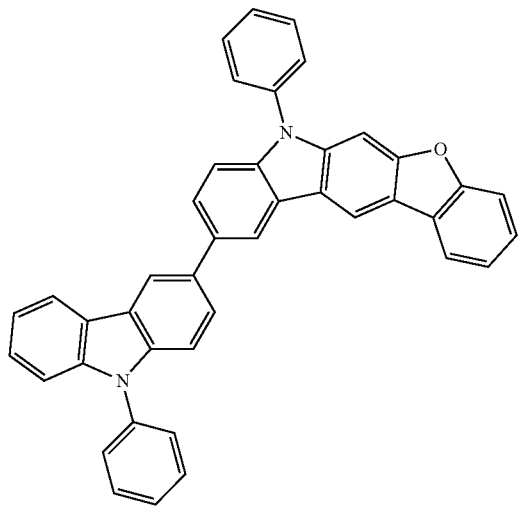
(110)

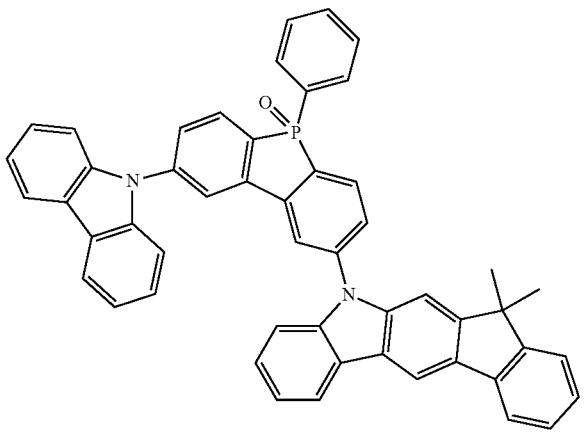
(111)

The compounds according to the invention can be prepared by synthesis steps known to the person skilled in the art, such as, for example, bromination, Suzuki coupling, Ullmann coupling, Hartwig-Buchwald coupling, etc. A unit of one of the formulae (2) to (4) is preferably introduced onto the indenocarbazole basic structure or the corresponding derivative with O or S in the bridge by a Suzuki coupling, an Ullmann coupling or a Hartwig-Buchwald coupling.

The invention therefore furthermore relates to a process for the preparation of a compound according to the invention, characterised in that the group of the formula (2), (3) or (4) is introduced by a Suzuki coupling, an Ullmann coupling or by a Hartwig-Buchwald coupling.

The present invention furthermore relates to mixtures comprising at least one compound according to the invention and at least one further compound. The further compound can be, for example, a fluorescent or phosphorescent dopant if the compound according to the invention is used as matrix material, in particular a phosphorescent dopant. Suitable dopants are mentioned below in connection with the organic electroluminescent devices and are also preferred for the mixtures according to the invention.

For processing from solution or from the liquid phase, for example by spin coating or by printing processes, solutions or formulations of the compounds or mixtures according to the invention are necessary. It may be preferred to use mixtures of two or more solvents. Suitable and preferred solvents are, for example, toluene, anisole, o-, m- or p-xylene, methyl benzoate, dimethyl anisole, mesitylene, tetralin, veratrol, THF, methyl-THF, THP, chlorobenzene, dioxane or mixtures of these solvents.

The present invention therefore furthermore relates to a formulation, in particular a solution, a suspension or a miniemulsion, comprising at least one compound or mixture according to the invention and one or more solvents, in particular organic solvents. The way in which solutions of this type can be prepared is known to the person skilled in the art and is described, for example, in WO 2002/072714, WO 2003/019694 and the literature cited therein.

The compounds and mixtures according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds or mixtures according to the invention in an electronic device, in particular in an organic electroluminescent device.

The present invention again furthermore relates to an electronic device comprising at least one of the compounds or mixtures according to the invention mentioned above. The preferences stated above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitised solar cells, organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), preferably organic electroluminescent devices (OLEDs, PLEDs), in particular phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). These can be fluorescent or phosphorescent emission layers or hybrid systems, in which fluorescent and phosphorescent emission layers are combined with one another.

The compound according to the invention in accordance with the embodiments indicated above can be employed in various layers, depending on the precise structure. Preference is given to an organic electroluminescent device comprising a compound of the formula (1) or in accordance with the preferred embodiments as matrix material for fluorescent or phosphorescent emitters, in particular for phosphorescent emitters, and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1) or in accordance with the preferred embodiments is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) or in accordance with the preferred embodiments is employed as matrix material for an emitting compound in an emitting layer, it is preferably employed in combination with one or more phosphorescent materials (triplet emitters). Phosphorescence in the sense of this invention is the luminescence from an excited state having spin multiplicity >1, in particular from an excited triplet state. For the purposes of this application, all luminescent transition-metal complexes and luminescent lanthanide complexes, in particular all iridium, platinum and copper complexes, are to be regarded as phosphorescent compounds.

The mixture comprising the compound of the formula (1) or in accordance with the preferred embodiments and the emitting compound comprises between 99 and 1% by vol., preferably between 98 and 10% by vol., particularly preferably between 97 and 60% by vol., in particular between 95 and 80% by vol., of the compound of the formula (1) or in accordance with the preferred embodiments, based on the entire mixture comprising emitter and matrix material. Correspondingly, the mixture comprises between 1 and 99% by vol., preferably between 2 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1) or in accordance with the preferred embodiments as matrix material for a phosphorescent emitter in combination with a further matrix material. Particularly suitable matrix materials which can be employed in combination with the compounds of the formula (1) or in accordance with the preferred embodiments are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, indenocarbazole derivatives, for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with WO 2010/054729, diazaphosphole derivatives, for example in accordance with WO 2010/054730, bridged carbazole derivatives, for example in accordance with US 2009/0136779, WO 2010/050778, WO 2011/042107, WO 2011/088877 or in accordance with the unpublished application EP 11003232.3, triphenylene derivatives, for example in accordance with WO 2012/048781, or lactams, for example in accordance with WO 2011/116865 or WO 2011/137951. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum. For the purposes of the present invention, all luminescent compounds which contain the above-mentioned metals are regarded as phosphorescent compounds.

Examples of the emitters described above are revealed by the applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339 or WO 2012/007086. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

It is furthermore possible to employ the compounds according to the invention in a hole-transport layer or in a hole-injection layer or in an exciton- or electron-blocking layer.

In the further layers of the organic electroluminescent device according to the invention, it is possible to use all materials as usually employed in accordance with the prior art. The person skilled in the art can therefore, without inventive step, all materials known for organic electroluminescent devices in combination with the compounds of the formula (1) according to the invention or in accordance with the preferred embodiments.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower or higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, ink-jet printing, LITI (light induced thermal imaging, thermal transfer printing), screen printing, flexographic printing, offset printing or nozzle printing. Soluble compounds, which are obtained, for example, by suitable substitution, are necessary for this purpose. These processes are also particularly suitable for oligomers, dendrimers and polymers.

Also possible are hybrid processes, in which, for example, one or more layers are applied from solution and one or more further layers are applied by vapour deposition. Thus, it is possible, for example, to apply the emitting layer from solution and to apply the electron-transport layer by vapour deposition.

These processes are generally known to the person skilled in the art and can be applied by him without inventive step to organic electroluminescent devices comprising the compounds according to the invention.

The compounds according to the invention have one or more of the following surprising advantages over the prior art on use in organic electroluminescent devices:
1. The power efficiency of corresponding devices becomes higher compared with systems in accordance with the prior art.
2. The stability of corresponding devices becomes higher compared with systems in accordance with the prior art, which is evident, in particular, from a significantly longer lifetime.
3. The organic electroluminescent devices according to the invention have a reduced operating voltage.
4. If the compounds according to the invention are used as matrix material for phosphorescent emitters, it is possible to achieve very good results with only a low emitter concentration in the region of less than 10% by vol.
5. The compounds according to the invention have very good thermal stability.

The invention is now illustrated in greater detail by the following examples, without wishing to restrict it thereby.

EXAMPLES

The following syntheses are carried out, unless indicated otherwise, under a protective-gas atmosphere in dried solvents. The solvents and reagents can be purchased, for example, from Sigma-ALDRICH or ABCR. In each case, the corresponding CAS numbers are also indicated for the compounds known from the literature.

Part A: Synthesis of the Precursors

Scheme 1:

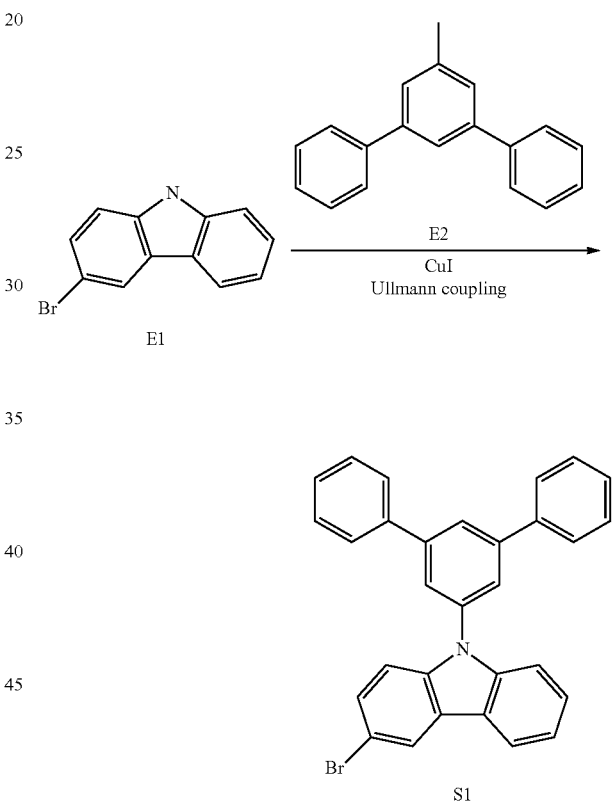

S1: 3-Bromo-9-[1,1';3',1"]terphenyl-5'-yl-9H-carbazole 10 g (41 mmol) of 3-bromo-9H-carbazole (CAS 86-74-8) and 16 g (45 mmol, 1.1 eq) of 5'-iodo-[1,1';3',1"]terphenyl are dissolved in 500 ml of p-xylene together with 51 g (270 mmol, 6.6 eq) of elemental copper, 115 g (540 mmol, 13 eq) of potassium carbonate and 0.52 g (4.5 mmol, 0.11 eq) of 18-crown-6 and heated under reflux. When the reaction is complete, the mixture is extracted three times with water, the organic phase is dried over sodium sulfate, the solvent is removed in vacuo, and the solid obtained is purified by means of column chromatography (ethyl acetate/heptane), giving 17 g (36 mmol, 53%) of the product.

The following synthones are prepared analogously:
| Ex. | E1 | E2 | Product | Yield [%] |
|---|---|---|---|---|
| S2 | (carbazole, Br) CAS 86-74-8 | (3-phenyltoluene) CAS 20442-79-9 | (N-biphenyl-carbazole-Br) | 48 |
| S3 | (carbazole, Br) CAS 86-74-8 | (9,9-dimethyl-2-bromofluorene) CAS 28320-31-2 | (fluorenyl-carbazole-Br) | 63 |
| S4 | (1-bromocarbazole) CAS 16807-11-7 | (toluene) CAS 591-50-4 | (N-phenyl-1-bromocarbazole) | 54 |
Scheme 2:
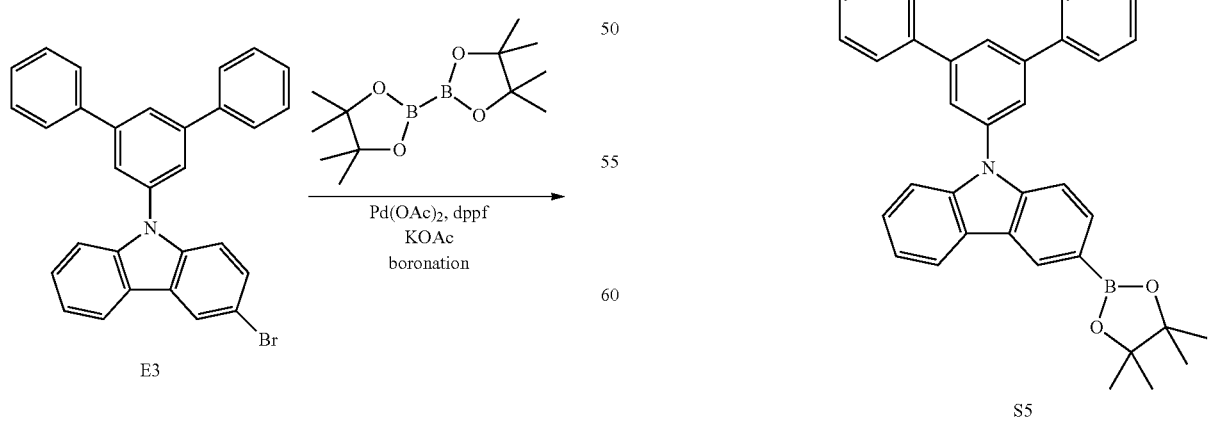

S5: 9-[1,1';3',1"]-Terphenyl-5'-yl-3-(4,4,5,5-tetramethyl-1,3,2-dioxaborolan-2-yl)-9H-carbazole 20 g (42 mmol) of 3-bromo-9-[1,1';3',1"]terphenyl-5'-yl-9H-carbazole S1, 13 g (50 mmol, 1.2 eq.) of bis(pinacolato)diborane (CAS 73183-34-4) and 12 g (130 mmol, 3 eq.) of potassium acetate are initially introduced in 300 ml of 1,4-dioxane and degassed with nitrogen for 30 minutes. 470 mg (0.84 mmol, 0.02 eq) of 1,1'-bis(diphenylphosphino)ferrocene and 190 mg (0.84 mmol, 0.02 eq) of palladium(II) acetate are subsequently added and heated to an internal temperature of 100° C. When the reaction is complete, ethyl acetate is added to the batch, and the mixture is extracted three times with water. The organic phase is evaporated, and the boronic ester is precipitated from heptane. Recrystallisation from acetonitrile gives 20 g (38 mmol, 91%) of the product.

The following synthones are prepared analogously:

Part B: Synthesis of the Compounds According to the Invention

Scheme 3:

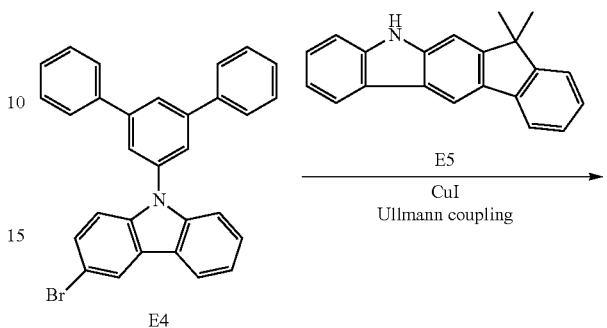

| Ex. | Starting material E3 | Product | Yield [%] |
|---|---|---|---|
| S6 | CAS 1153-85-1 | | 97 |
| S7 | CAS 57103-20-5 | | 89 |

2.4 equivalents of the diborane

-continued

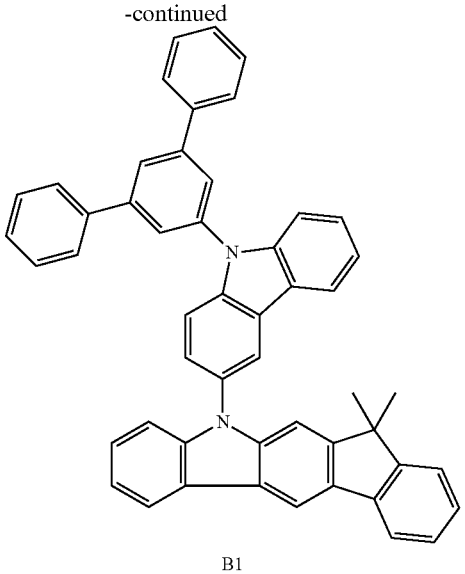

B1

B1: 12,12-Dimethyl-10-(9-[1,1';3',1"]terphenyl-5'-yl-9H-carbazol-3-yl)-10,12-dihydro-10-azaindeno[2,1-b]fluorene 7.6 g (33 mmol) of 12,12-dimethyl-10,12-dihydro-10-azaindeno[2,1-b]fluorene (WO 2010/136109), 17 g (36 mmol, 1.1 eq) of 3-bromo-9-[1,1';3',1"]-terphenyl-5'-yl-9H-carbazole S1 and 12.1 g (12 mmol, 0.36 eq) of copper(I) iodide are suspended in 1 l of 1,4-dioxane with 150 g (706 mmol, 4 eq) of potassium phosphate. The reaction mixture is subsequently degassed for 30 minutes, and 17.6 ml (147 mmol, 0.83 eq) of trans-cyclohexylamine are added under a protective gas. The batch is heated under reflux for 12 h, and, when the reaction is complete, dichloromethane is added. The precipitated solid is filtered off with suction, dissolved in toluene and filtered through silica gel. After removal of the solvent in vacuo, the residue is recrystallised a number of times from toluene/heptane and finally sublimed, giving 17.6 g (33.5 mmol, 57%) of a colourless solid having an HPLC purity >99.9%.

The following compounds are prepared analogously to B1:

| Ex. | E5 | E4 |
|---|---|---|
| B2 | 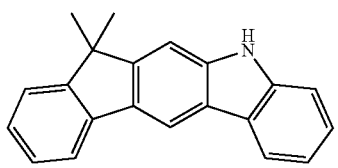<br>WO 2010/136109 | 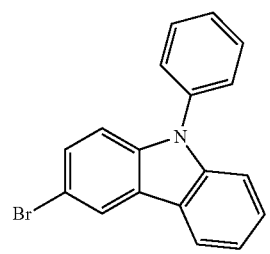<br>CAS 1153-85-1 |
| B3 | 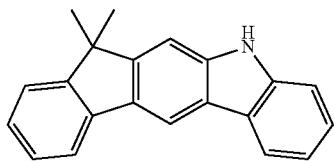<br>WO 2010/136109 | 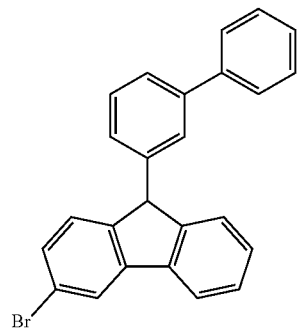<br>S2 |

-continued
B4 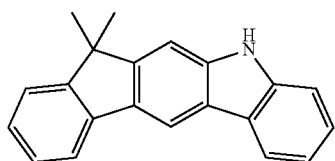
WO 2010/136109
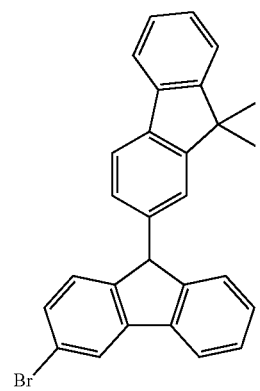 [SMILES: CC1(C)c2ccccc2-c2ccc(C3c4ccccc4-c4cc(Br)ccc43)cc21]
S3
B5 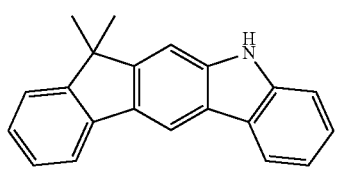 [SMILES: CC1(C)c2ccccc2-c2cc3c(cc21)[nH]c1ccccc13]
WO 2010/136109
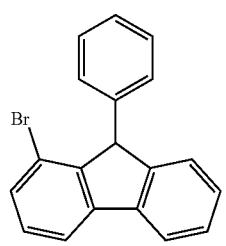 [SMILES: Brc1cccc2c1C(c1ccccc1)c1ccccc1-2]
S4
B6 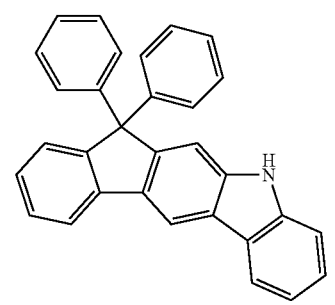 [SMILES: c1ccc(C2(c3ccccc3)c3ccccc3-c3cc4c(cc32)[nH]c2ccccc24)cc1]
WO 2010/136109
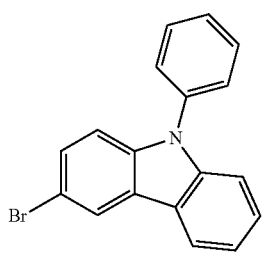 [SMILES: Brc1ccc2c(c1)c1ccccc1n2-c1ccccc1]
CAS 1153-85-1
B7 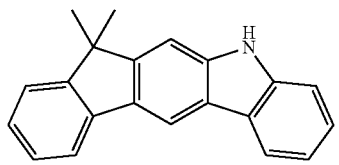 [SMILES: CC1(C)c2ccccc2-c2cc3c(cc21)[nH]c1ccccc13]
WO 2010/136109
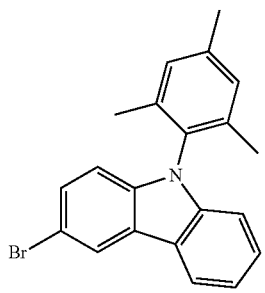 [SMILES: Cc1cc(C)c(-n2c3ccccc3c3cc(Br)ccc32)c(C)c1]
CAS 1141017-78-8

| | | |
|---|---|---|
| B8 | 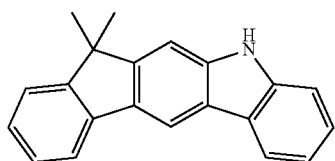<br>WO 2010/136109 | 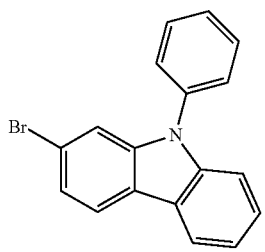<br>CAS 94994-62-4 |
| B9 | 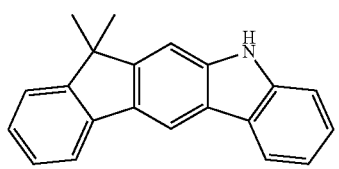<br>WO 2010/136109 | 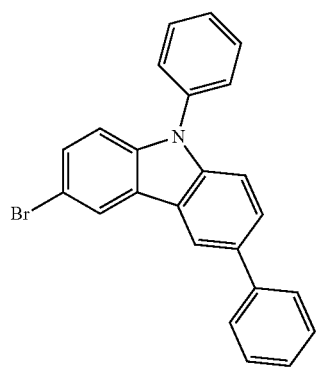<br>CAS 1160294-85-8 |
| B10 | 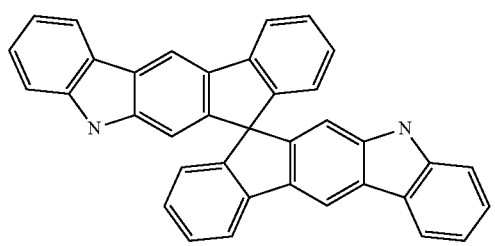<br>WO 2010/136109 | 2.2 equivalents<br>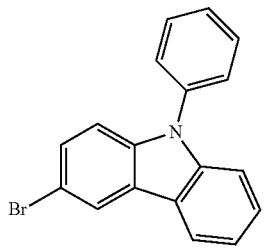<br>CAS 1153-85-1 |
| B11 | 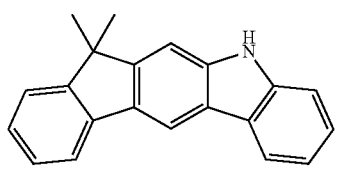<br>WO 2010/136109 | 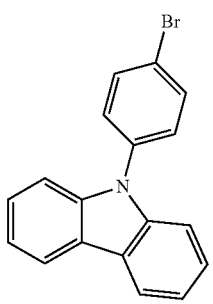<br>CAS 57102-42-8 |

-continued
B12 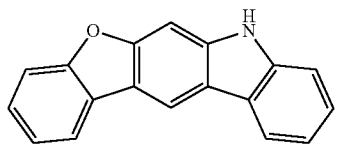 [SMILES: c1ccc2c(c1)[nH]c1cc3oc4ccccc4c3cc12]
CAS 1246308-83-7
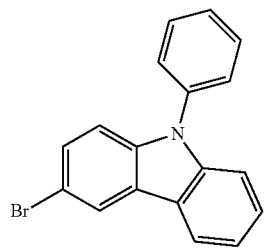 [SMILES: Brc1ccc2c(c1)c1ccccc1n2-c1ccccc1]
CAS 1153-85-1
B13 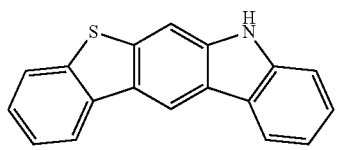
CAS 1255309-04-6
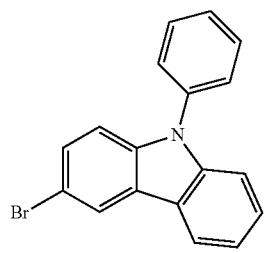
CAS 1153-85-1
B14 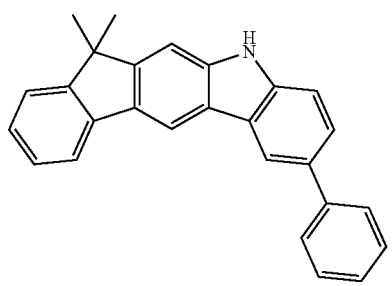 [SMILES: CC1(C)c2ccccc2-c2cc3c(cc21)[nH]c1ccc(-c2ccccc2)cc13]
WO 2010/136109
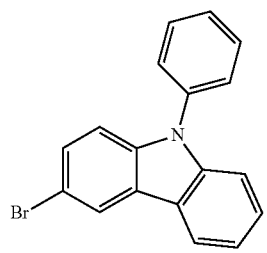 [SMILES: Brc1ccc2c(c1)c1ccccc1n2-c1ccccc1]
CAS 1153-85-1
B15 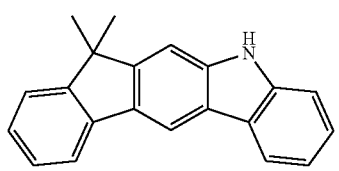 [SMILES: CC1(C)c2ccccc2-c2cc3c(cc21)[nH]c1ccccc13]
WO 2010/136109
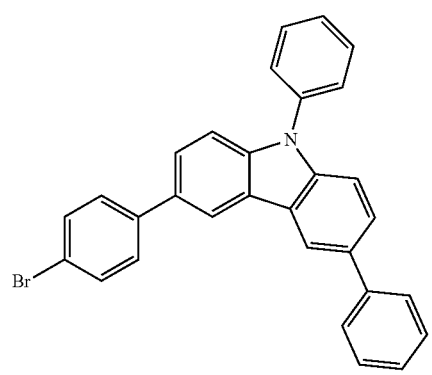 [SMILES: Brc1ccc(-c2ccc3c(c2)c2cc(-c4ccccc4)ccc2n3-c2ccccc2)cc1]
CAS 1186644-47-2
B16 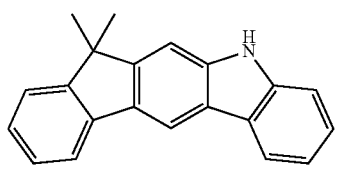 [SMILES: CC1(C)c2ccccc2-c2cc3c(cc21)[nH]c1ccccc13]
WO 2010/136109
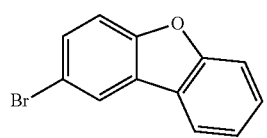 [SMILES: Brc1ccc2oc3ccccc3c2c1]
CAS 86-76-0

-continued
B17
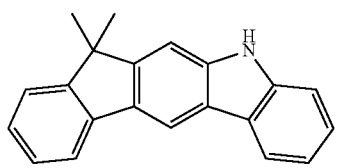 [SMILES: CC1(C)c2ccccc2-c2cc3c(cc21)[nH]c1ccccc13]
WO 2010/136109
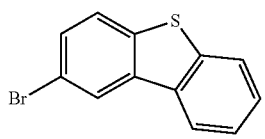 [SMILES: Brc1ccc2sc3ccccc3c2c1]
CAS 22439-61-8
B18
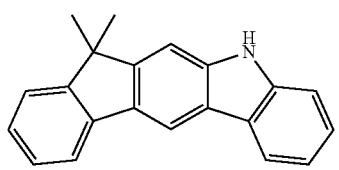 [SMILES: CC1(C)c2ccccc2-c2cc3c(cc21)[nH]c1ccccc13]
WO 2010/136109
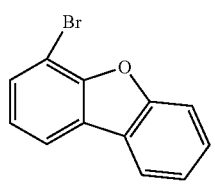 [SMILES: Brc1cccc2c1oc1ccccc12]
CAS 89827-45-2
B19
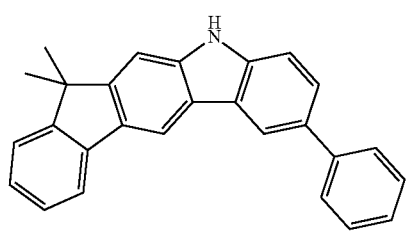 [SMILES: CC1(C)c2ccccc2-c2cc3c(cc21)[nH]c1ccc(-c2ccccc2)cc13]
WO 2010/136109
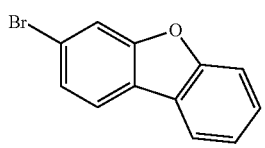 [SMILES: Brc1ccc2c(c1)oc1ccccc12]
CAS 26608-06-0
B20
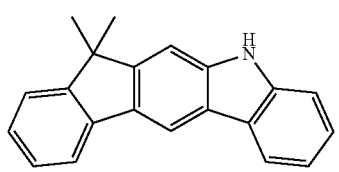 [SMILES: CC1(C)c2ccccc2-c2cc3c(cc21)[nH]c1ccccc13]
WO 2010/136109
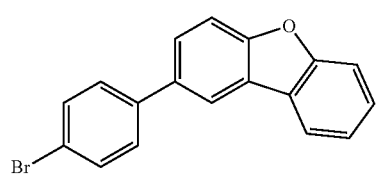 [SMILES: Brc1ccc(-c2ccc3oc4ccccc4c3c2)cc1]
CAS 955959-86-1
B21
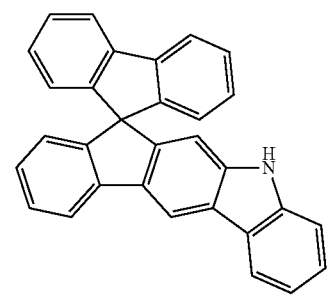 [SMILES: c1ccc2c(c1)-c1ccccc1C21c2ccccc2-c2cc3c(cc21)[nH]c1ccccc13]
WO 2010/136109
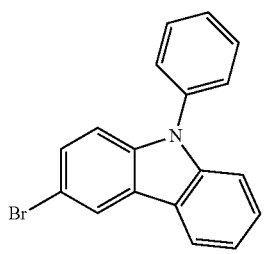 [SMILES: Brc1ccc2c(c1)c1ccccc1n2-c1ccccc1]
CAS 1153-85-1
B22
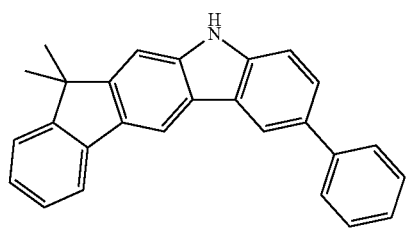 [SMILES: CC1(C)c2ccccc2-c2cc3c(cc21)[nH]c1ccc(-c2ccccc2)cc13]
WO 2010/136109
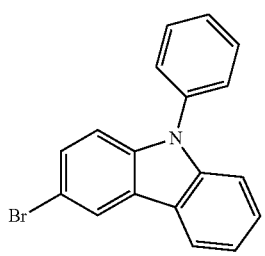 [SMILES: Brc1ccc2c(c1)c1ccccc1n2-c1ccccc1]
CAS 1153-85-1

| | |
|---|---|
| B23 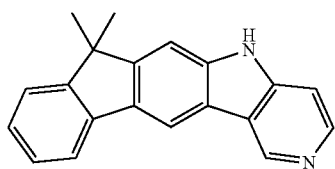 [SMILES: CC1(C)c2ccccc2-c2cc3c(cc21)[nH]c1ccncc13] WO 2010/136109 | 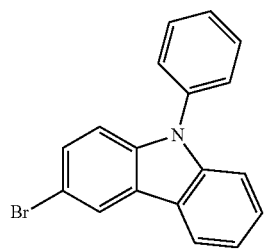 [SMILES: Brc1ccc2c(c1)c1ccccc1n2-c1ccccc1] CAS 1153-85-1 |
| B24 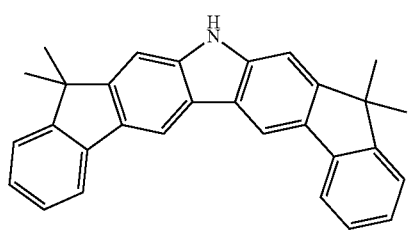 [SMILES: CC1(C)c2ccccc2-c2cc3c(cc21)[nH]c1cc2c(cc13)-c1ccccc1C2(C)C] WO 2010/136109 | 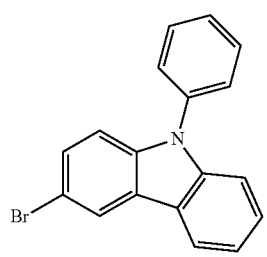 [SMILES: Brc1ccc2c(c1)c1ccccc1n2-c1ccccc1] CAS 1153-85-1 |
| B25 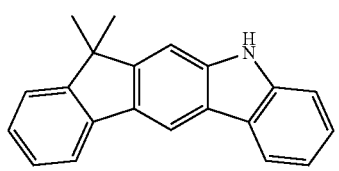 [SMILES: CC1(C)c2ccccc2-c2cc3c(cc21)[nH]c1ccccc13] WO 2010/136109 | 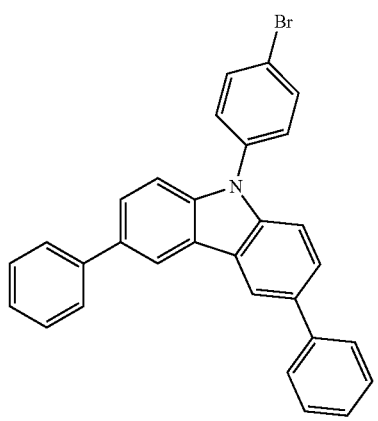 [SMILES: Brc1ccc(-n2c3ccc(-c4ccccc4)cc3c3cc(-c4ccccc4)ccc32)cc1] CAS 607739-92-4 |
| B26 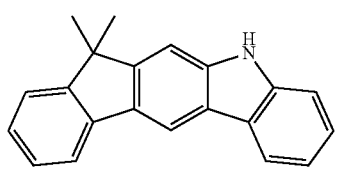 [SMILES: CC1(C)c2ccccc2-c2cc3c(cc21)[nH]c1ccccc13] WO 2010/136109 | 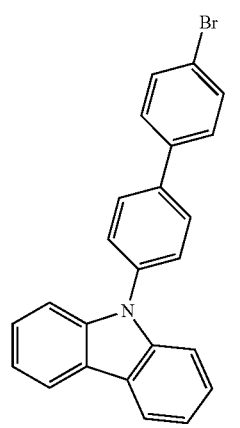 [SMILES: Brc1ccc(-c2ccc(-n3c4ccccc4c4ccccc43)cc2)cc1] CAS 212385-73-4 |

-continued
| | | |
|---|---|---|
| B27 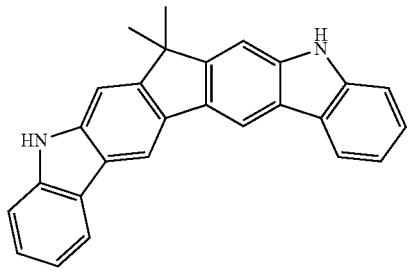 WO 2010/136109 | 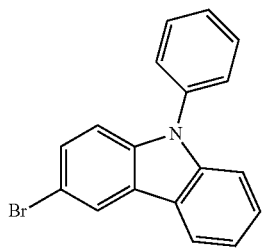 CAS 1153-85-1 | 2.2 equivalents |
| Ex. | Product | Yield [%] |
|---|---|---|
| B2 | 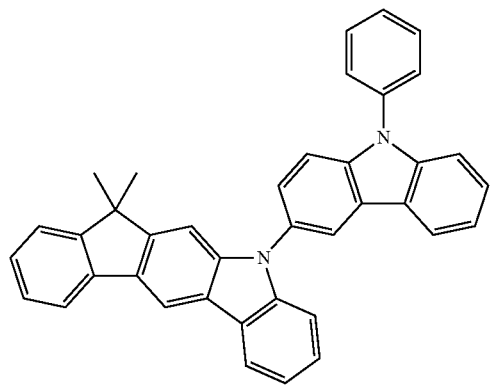 [SMILES: CC1(C)c2ccccc2-c2cc3c4ccccc4n(-c4ccc5c(c4)c4ccccc4n5-c4ccccc4)c3cc21] | 54 |
| B3 | 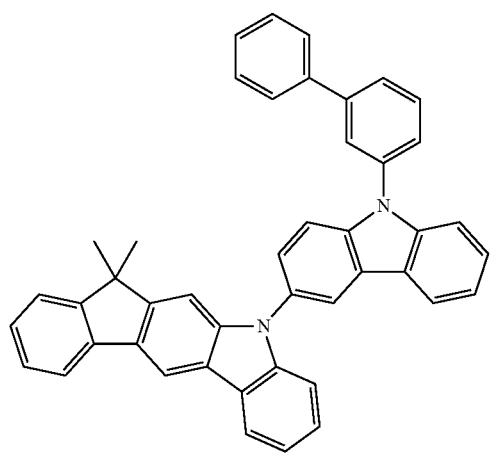 [SMILES: CC1(C)c2ccccc2-c2cc3c4ccccc4n(-c4ccc5c(c4)c4ccccc4n5-c4cccc(-c5ccccc5)c4)c3cc21] | 74 |

| | |
|---|---|
| B4 | 65 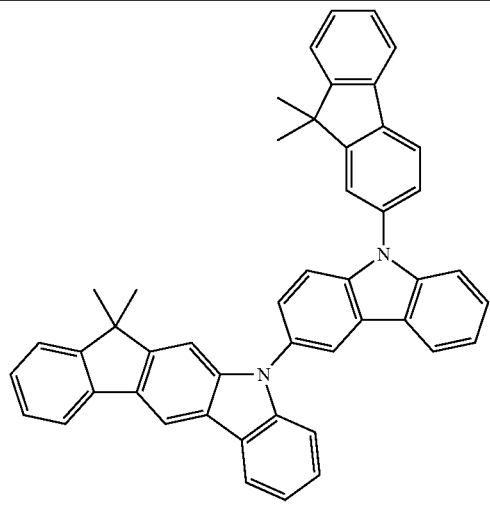 |
| B5 | 53 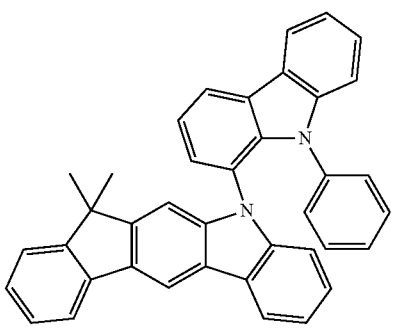 [SMILES: CC1(C)c2ccccc2-c2cc3c4ccccc4n(-c4cccc5c6ccccc6n(-c6ccccc6)c45)c3cc21] |
| B6 | 59 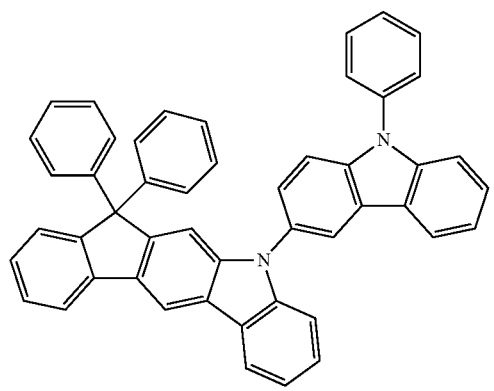 [SMILES: c1ccc(-n2c3ccccc3c3cc(-n4c5ccccc5c5cc6c(cc54)C(c4ccccc4)(c4ccccc4)c4ccccc4-6)ccc32)cc1] |
| B7 | 49 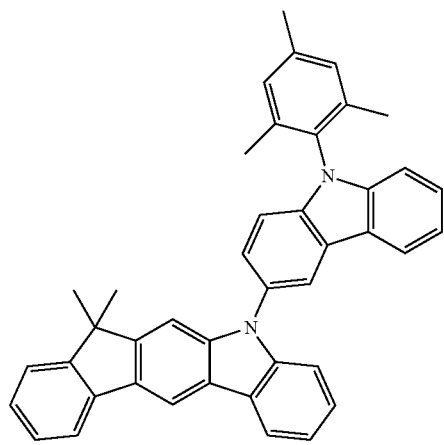 [SMILES: Cc1cc(C)c(-n2c3ccccc3c3cc(-n4c5ccccc5c5cc6c(cc54)C(C)(C)c4ccccc4-6)ccc32)c(C)c1] |

| | | |
|---|---|---|
| B8 | 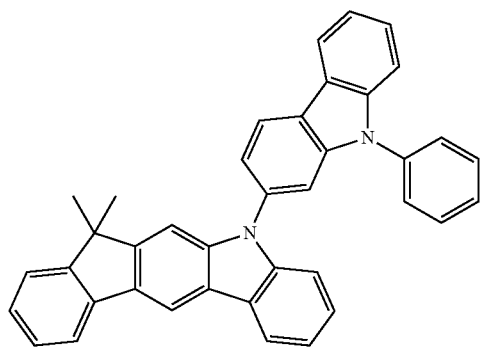 [SMILES: CC1(C)c2ccccc2-c2cc3c4ccccc4n(-c4ccc5c6ccccc6n(-c6ccccc6)c5c4)c3cc21] | 53 |
| B9 | 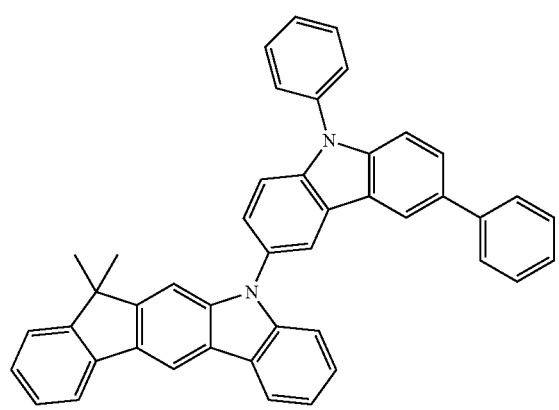 [SMILES: CC1(C)c2ccccc2-c2cc3c4ccccc4n(-c4ccc5c(c4)c4cc(-c6ccccc6)ccc4n5-c4ccccc4)c3cc21] | 45 |
| B10 | 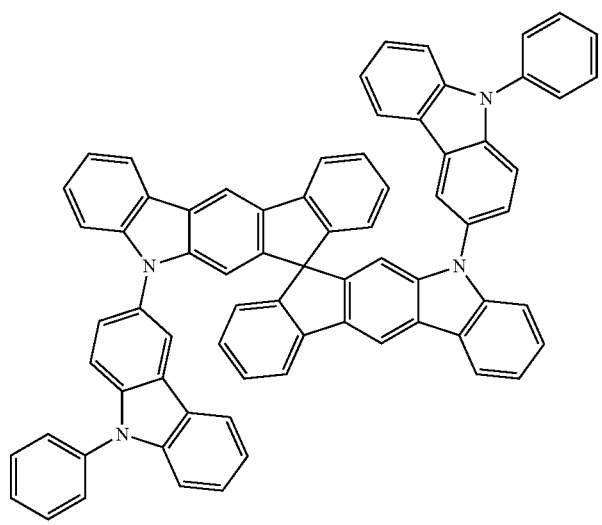 [SMILES: c1ccc(-n2c3ccccc3c3cc(-n4c5ccccc5c5cc6c(cc54)C4(c5ccccc5-6)c5ccccc5-c5cc6c7ccccc7n(-c7ccc8c(c7)c7ccccc7n8-c7ccccc7)c6cc54)ccc32)cc1] | 64 |

-continued
B11      61
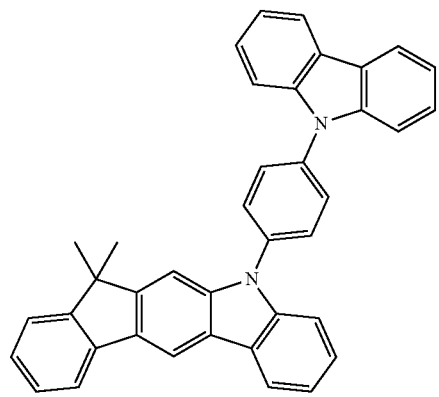 [SMILES: CC1(C)c2ccccc2-c2cc3c4ccccc4n(-c4ccc(-n5c6ccccc6c6ccccc65)cc4)c3cc21]
B12      57
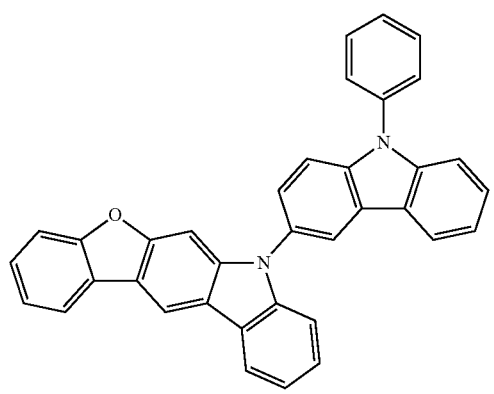
B13      48
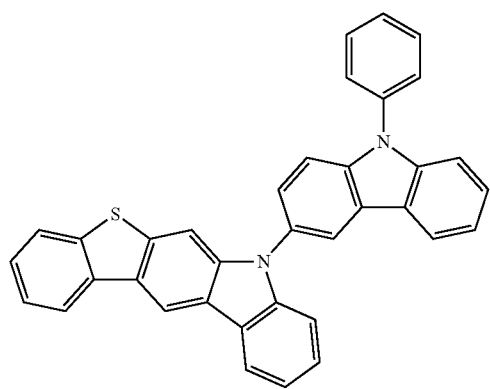 [SMILES: c1ccc(-n2c3ccccc3c3cc(-n4c5ccccc5c5cc6c(cc54)oc4ccccc46)ccc32)cc1]

| | | |
|---|---|---|
| B14 | 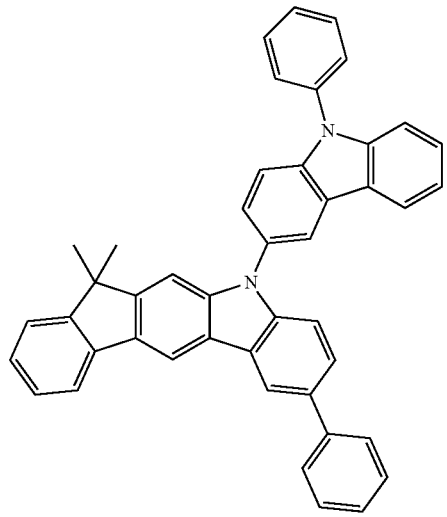 [SMILES: CC1(C)c2ccccc2-c2cc3c4cc(-c5ccccc5)ccc4n(-c4ccc5c(c4)c4ccccc4n5-c4ccccc4)c3cc21] | 78 |
| B15 | 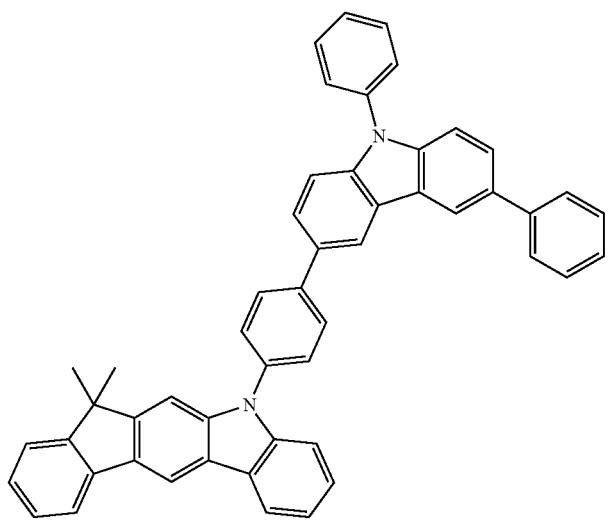 [SMILES: CC1(C)c2ccccc2-c2cc3c4ccccc4n(-c4ccc(-c5ccc6c(c5)c5cc(-c7ccccc7)ccc5n6-c5ccccc5)cc4)c3cc21] | 58 |
| B16 | 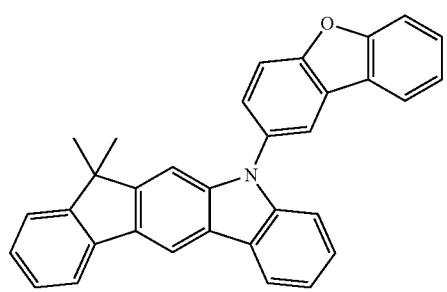 | 54 |
| B17 | 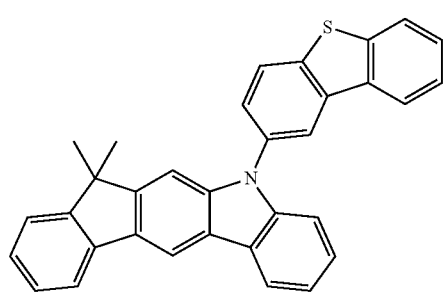 [SMILES: CC1(C)c2ccccc2-c2cc3c4ccccc4n(-c4ccc5oc6ccccc6c5c4)c3cc21] | 45 |

B18 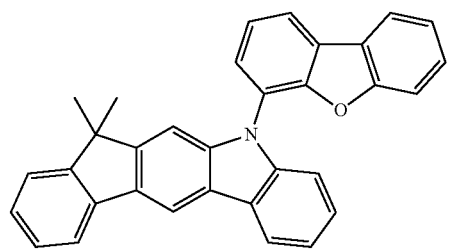 [SMILES: CC1(C)c2ccccc2-c2cc3c4ccccc4n(-c4cccc5c4oc4ccccc45)c3cc21] 57
B19 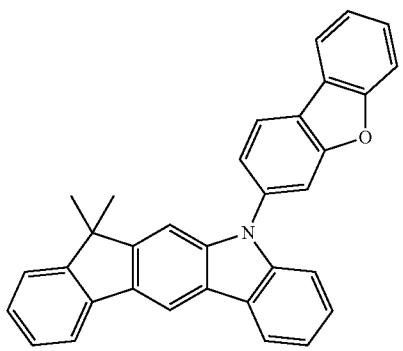 [SMILES: CC1(C)c2ccccc2-c2cc3c4ccccc4n(-c4ccc5c(c4)oc4ccccc45)c3cc21] 51
B20 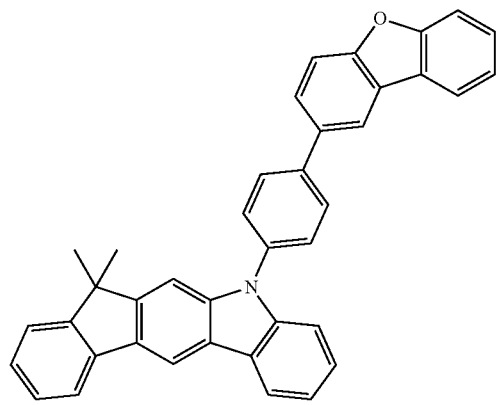 [SMILES: CC1(C)c2ccccc2-c2cc3c4ccccc4n(-c4ccc(-c5ccc6oc7ccccc7c6c5)cc4)c3cc21] 54
B21 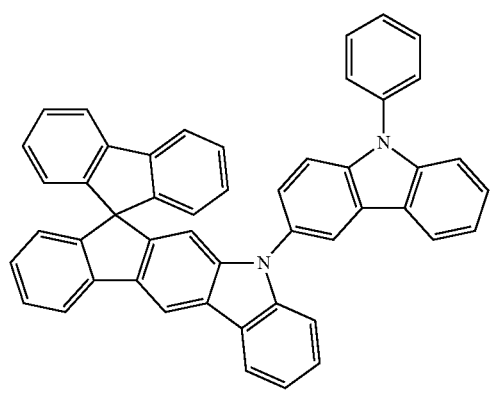 [SMILES: c1ccc(-n2c3ccccc3c3cc(-n4c5ccccc5c5cc6c(cc54)C4(c5ccccc5-c5ccccc54)c4ccccc4-6)ccc32)cc1] 62

B22 43
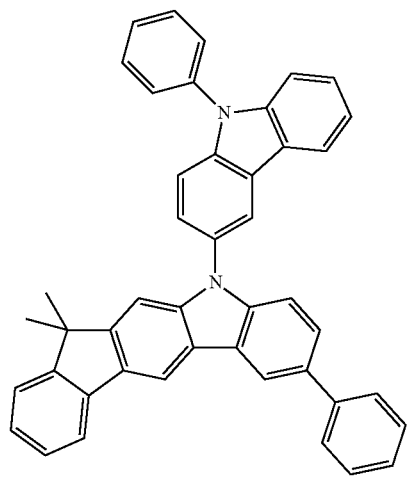 [SMILES: CC1(C)c2ccccc2-c2cc3c4cc(-c5ccccc5)ccc4n(-c4ccc5c(c4)c4ccccc4n5-c4ccccc4)c3cc21]
B23 54
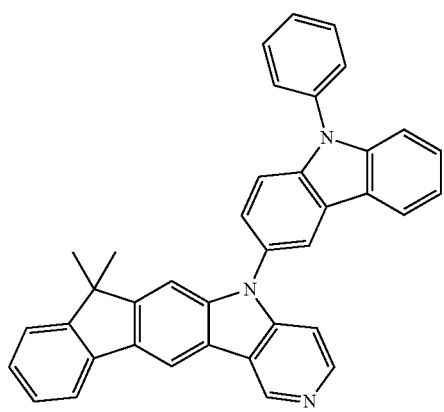 [SMILES: CC1(C)c2ccccc2-c2cc3c4cnccc4n(-c4ccc5c(c4)c4ccccc4n5-c4ccccc4)c3cc21]
B24 56
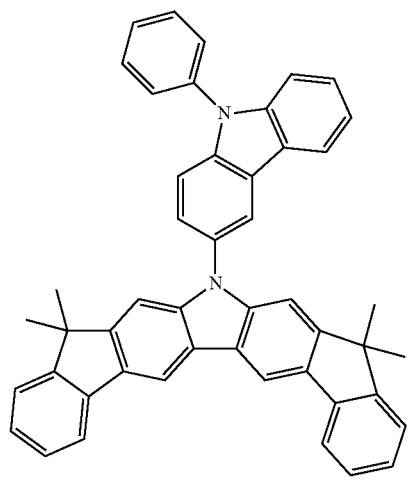 [SMILES: CC1(C)c2ccccc2-c2cc3c4cc5c(cc4n(-c4ccc6c(c4)c4ccccc4n6-c4ccccc4)c3cc21)C(C)(C)c1ccccc1-5]

-continued
B25 54
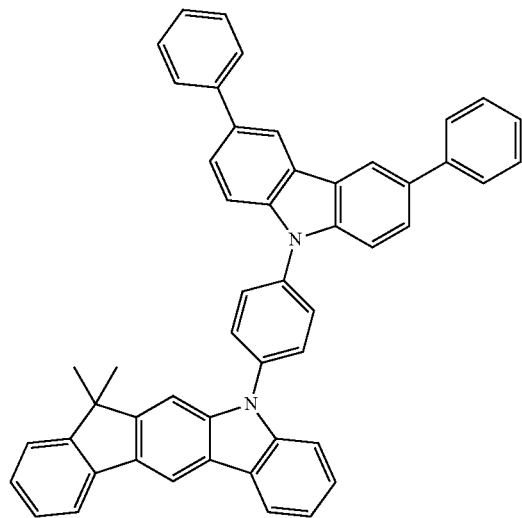 [SMILES: CC1(C)c2ccccc2-c2cc3c4ccccc4n(-c4ccc(-n5c6ccc(-c7ccccc7)cc6c6cc(-c7ccccc7)ccc65)cc4)c3cc21]
B26 53
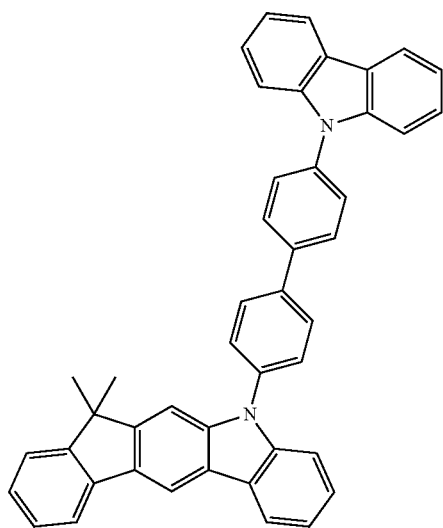 [SMILES: CC1(C)c2ccccc2-c2cc3c4ccccc4n(-c4ccc(-c5ccc(-n6c7ccccc7c7ccccc76)cc5)cc4)c3cc21]
B27 45
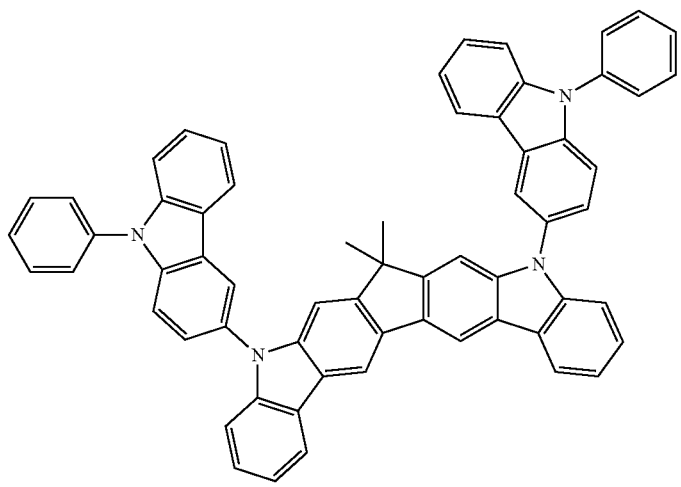 [SMILES: CC1(C)c2cc3c(cc2-c2cc4c5ccccc5n(-c5ccc6c(c5)c5ccccc5n6-c5ccccc5)c4cc21)c1ccccc1n3-c1ccc2c(c1)c1ccccc1n2-c1ccccc1]

Scheme 4:

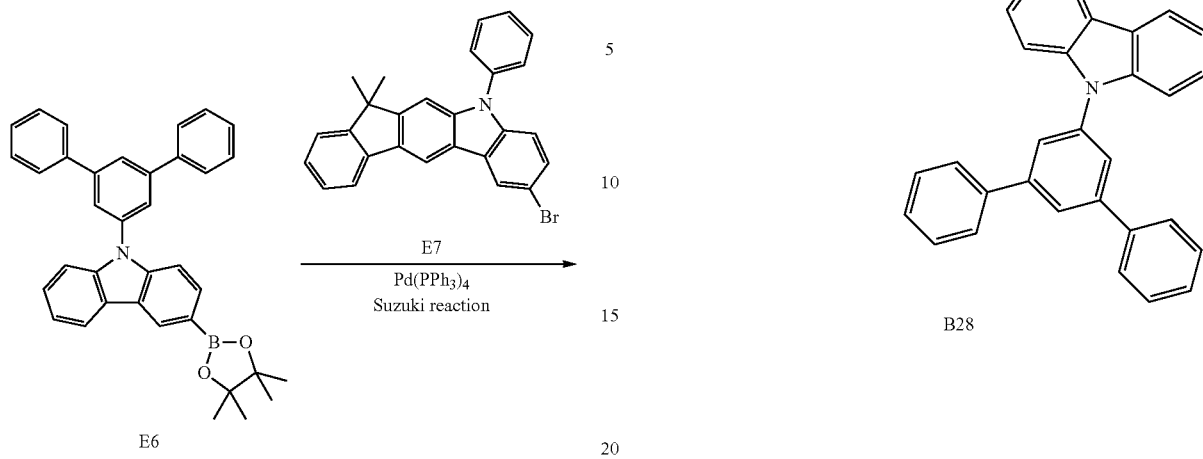

E6

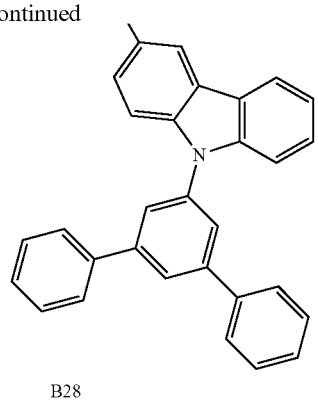

B28

B28: 12,12-Dimethyl-10-phenyl-7-(9-[1,1';3',1"]terphenyl-5'-yl-9H-carbazol-3-yl)-10,12-dihydro-10-azaindeno[2,1-b]fluorene 20 g (38 mmol) of 9-[1,1';3',1"]-terphenyl-5'-yl-3-(4,4,5,5-tetramethyl-1,3,2-dioxaborolan-2-yl)-9H-carbazole S5 and 17 g (38 mmol, 1 eq) of 7-bromo-12,12-dimethyl-10-phenyl-10,12-dihydro-10-azaindeno[2,1-b]fluorene (WO 2010/136109) are initially introduced in 250 ml of acetone, and 62 ml (84 mmol, 2.2 eq) of tetraethylammonium hydroxide (20% solution in water) are added. The reaction mixture is degassed with nitrogen for 30 minutes, and 0.88 g (0.76 mmol, 0.02 eq) of tetrakis(triphenylphosphine)palladium(0) are subsequently added, and the mixture is stirred overnight at 50° C. The precipitated solid is filtered off with suction and purified by means of hot extraction, repeated recrystallisation from heptane/toluene and final sublimation, giving 14 g (19 mmol, 51%) of the product having an HPLC purity >99.9%.

The following compounds are prepared analogously:

| Ex. | E6 | E7 |
|---|---|---|
| B29 | | |

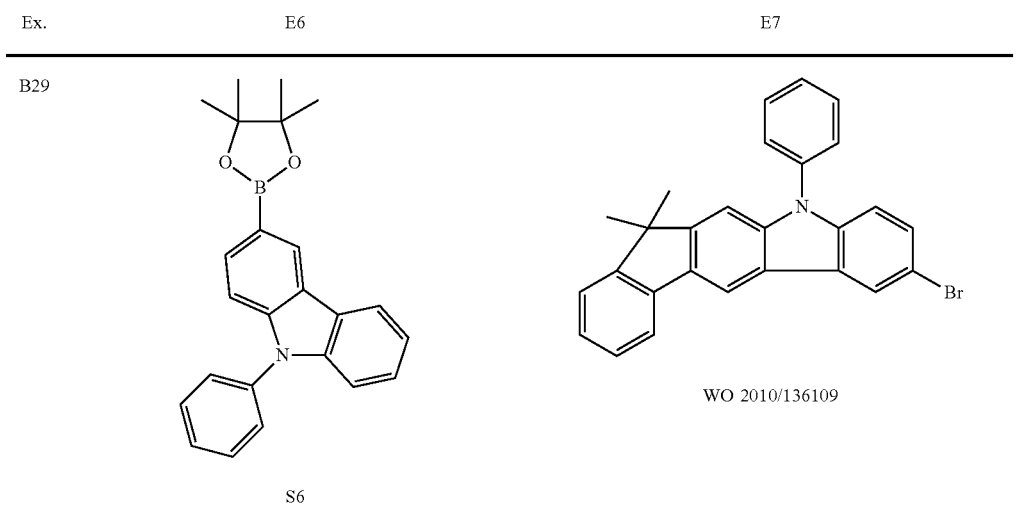

| B30 | 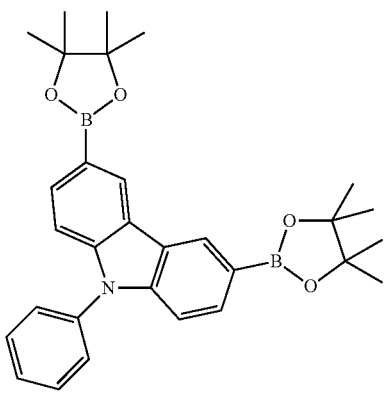 S7 | 2 equivalents 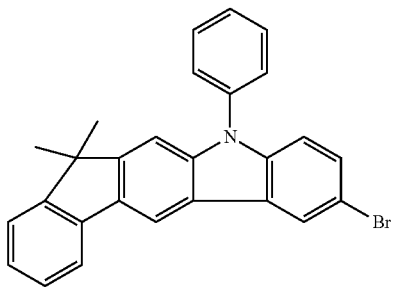 WO 2010/136109 |
| Ex. | Product | Yield [%] |
|---|---|---|
| B29 | | 63 |
| B30 | | 53 |

Scheme 5:

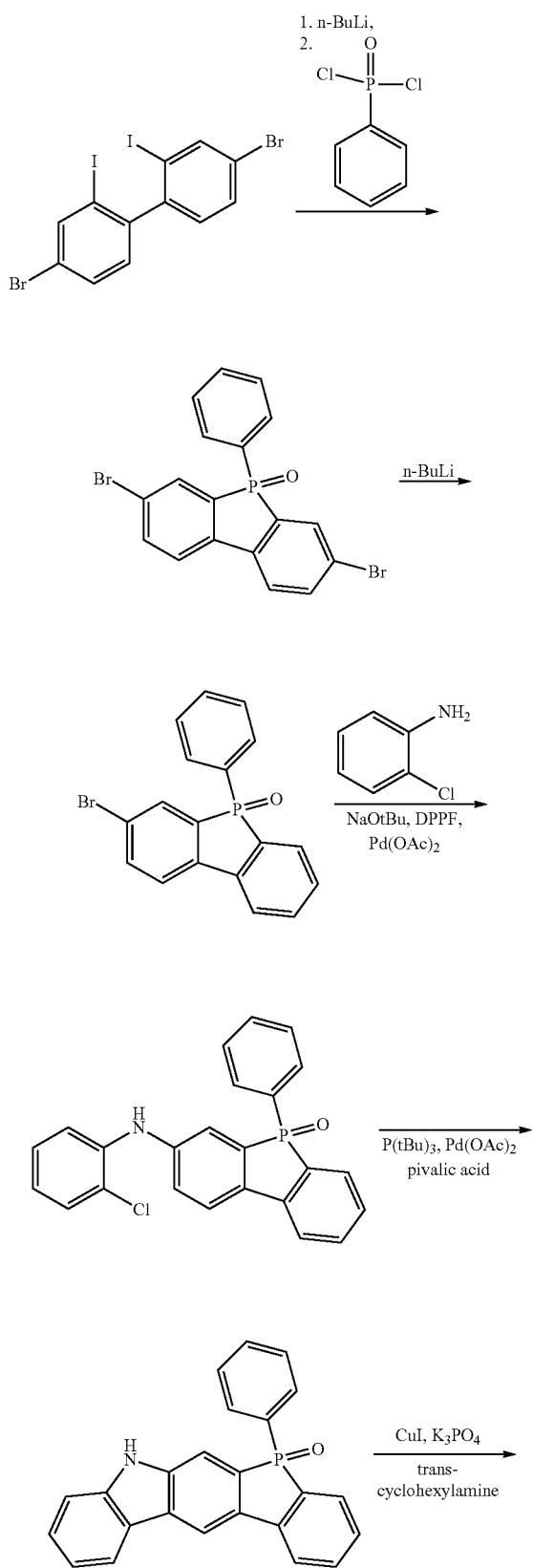

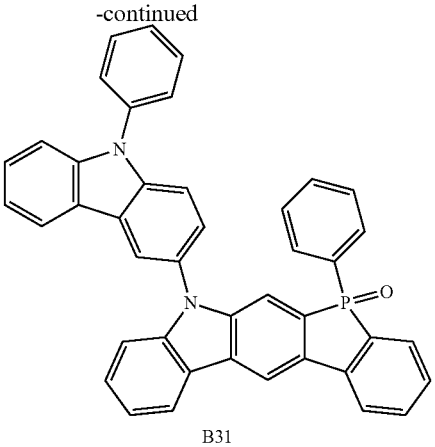

B31

3,7-Dibromo-5-phenyldibenzophosphole 5-oxide 66 ml (106 mmol, 2.0 eq) of n-butyllithium (1.6 M in hexane) are added to a solution of 30 g (53 mmol) of 4,4'-dibromo-2,2'-diiodobiphenyl in 500 ml of dry THF at −78° C., and the mixture is stirred at this temperature for 30 minutes. 11 g (56 mmol, 1.06 eq) of dichlorophenylphosphine oxide are subsequently added dropwise, and, when the reaction is complete, the reaction mixture is warmed to room temperature. After hydrolysis using water, the organic phase is extracted with ether, and the combined organic phases are dried over sodium sulfate. The solvent is removed in a rotary evaporator, and the crude product obtained is purified by column chromatography (heptane/ethyl acetate 6:1), giving 20 g (45 mmol, 85%) of the product.

3-Bromo-5-phenyldibenzophosphole 5-oxide 20 g (45 mmol) of 3,7-dibromo-5-phenyldibenzophosphole 5-oxide in 400 ml of dry THF are cooled to −78° C., and 28 ml (45 mmol, 1.0 eq) of n-butyllithium (1.6 M in hexane) are slowly added at this temperature. After 1 h, the mixture is slowly warmed to room temperature, 50 ml of 1M HCl are added, and the mixture is stirred for a further 2 h. The mixture is subsequently extracted with ethyl acetate, washed with water, and the combined organic phases are dried over sodium sulfate. The solvents are removed in a rotary evaporator, and the product obtained is used without further purification steps, giving 16 g (43 mmol, 96%) of the monobromide.

(2-Chlorophenyl)-(5-oxo-5-phenyl-5H-5lambda*5*-dibenzophosphol-3-yl)amine 16 g (43 mmol) of 3-bromo-5-phenyldibenzophosphole 5-oxide are initially introduced in 400 ml of toluene together with 6.6 ml (52 mmol, 1.2 eq) of 2-chloroaniline and 11 g (112 mmol, 2.6 eq) of sodium tert-butoxide, and 480 mg (0.86 mmol, 0.2 eq) of DPPF and 97 mg (0.43 mmol, 0.01 eq) of palladium acetate are added. The reaction mixture is heated under reflux overnight, and, when the reaction is complete, 200 ml of water are added. The phases are separated, and the aqueous phase is extracted with toluene. The combined organic phases are dried over sodium sulfate and filtered through aluminum oxide. The solvent is removed in vacuo, and the residue obtained is purified by column chromatography (heptane/ethyl acetate 5:1), giving 16 g (39 mmol, 91%) of the product.

12-Phenyl-10H-10-aza-12-phosphaindeno[2,1-b]fluorene 12-oxide 16 g (39 mmol) of (2-chlorophenyl)-(5-oxo-5-phenyl-5H-5lambda*5*-dibenzophosphol-3-yl)amine and 14 g (100 mmol, 2.6 eq) of potassium carbonate are initially introduced in 250 ml of NMP, and 1.4 g (13 mmol, 0.34 eq) of pivalic acid are added. 3.1 ml of a 1M tri-tert-butylphosphine solution in toluene (3.1 mmol, 0.08 eq) and 440 mg (2.0 mmol, 0.05 eq) of palladium acetate are subsequently added, and the reaction mixture is heated overnight at an internal temperature of 130° C. The batch is cooled to room temperature, and 300 ml of toluene and 100 ml of water are added. The aqueous phase is extracted three times with toluene, and the combined organic phases are likewise washed three times with water and finally dried over sodium sulfate. After removal of the solvent, the crude product obtained is purified by column chromatography, giving 13 g (35 mmol, 89%) of the product.

B31: 12-Phenyl-10-(9-phenyl-9H-carbazol-3-yl)-10H-10-aza-12-phosphaindeno[2,1-b]fluorene 12-oxide The experiment is carried out analogously to B1, giving 14 g (23 mmol, 67%) of the target product B31.

Part C: Comparison of the Thermal Stability

If 100 mg of the compound ICvCbz1 are melted in a glass ampoule in vacuo (pressure about $10^{-2}$ mbar) and this is stored at 310° C. for 14 days in an oven, the purity according to HPLC changes from 99.7% to 89.2%. With compound B29, the purity according to HPLC in the same procedure changes from 99.8% to 99.6%, i.e. far fewer decomposition products form under the same thermal load. This is a significant industrial advantage, since the materials in the industrial production of organic electroluminescent devices are subjected to high temperatures for a long time.

Part D: Organic Electroluminescent Devices

OLEDs according to the invention and OLEDs in accordance with the prior art are produced by a general process in accordance with WO 2004/058911, which is adapted to the circumstances described here (layer-thickness variation, materials).

The data of various OLEDs are presented in Examples V1 to E17 below (see Tables 1 and 2). Glass plates coated with structured ITO (indium tin oxide) in a thickness of 50 nm are coated with 20 nm of PEDOT:PSS (poly(3,4-ethylenedioxythiophene)poly(styrenesulfonate), purchased as CLEVIOS™ P VP A14083 from Heraeus Precious Metals GmbH, Germany, applied by spin coating from aqueous solution) for improved processing. These coated glass plates form the substrates to which the OLEDs are applied. The OLEDs have the following layer structure: substrate/hole-transport layer (HTL)/interlayer (IL)/electron-blocking layer (EBL)/emission layer (EML)/hole-blocking layer (HBL)/electron-transport layer (ETL) and finally an aluminium cathode with a thickness of 100 nm. The precise structure of the OLEDs is shown in Table 1. The materials required for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or materials in a certain proportion by volume by coevaporation. An expression such as IC1:IC2:TEG1 (30%:60%:10%) here means that material IC1 is present in the layer in a proportion by volume of 30%, IC2 is present in the layer in a proportion by volume of 60% and TEG1 is present in the layer in a proportion by volume of 10%. An analogous situation applies to the electron-transport layer.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines), assuming Lambert emission characteristics, and the lifetime are determined. The electroluminescence spectra are determined at a luminous density of 1000 cd/m$^2$, and the CIE 1931 x and y colour coordinates are calculated therefrom. The expression U1000 in Table 2 denotes the voltage required for a luminous density of 1000 cd/m$^2$. CE1000 and PE1000 denote the current and power efficiencies achieved at 1000 cd/m$^2$. Finally, EQE1000 denotes the external quantum efficiency at an operating luminous density of 1000 cd/m$^2$. The lifetime LT defines the time after which the luminous density on operation at constant current drops from the initial luminous density L0 to a certain proportion L1. A specification of L0=10000 cd/m$^2$ and L1=70% in Table 2 means that the lifetime indicated in column LT corresponds to the time after which the initial luminous density drops from 10000 cd/m$^2$ to 7000 cd/m$^2$.

The data of the various OLEDs are summarised in Table 2. Example V1-V8 are comparative examples in accordance with the prior art, Examples E1-E17 show data of OLEDs comprising materials according to the invention.

Some of the examples are explained in greater detail below in order to illustrate the advantages of the compounds according to the invention. However, it should be pointed out that this only represents a selection of the data shown in Table 2. As can be seen from the table, significant improvements compared with the prior art are also achieved on use of the compounds according to the invention that are not described in greater detail.

Use of Compounds According to the Invention as Component of a Mixed-Matrix System In the following examples, data of OLEDs in which the mixing ratio is selected in such a way that a maximum lifetime is obtained are shown.

If Examples V2 and E1 are compared, it can be seen that compound B2 according to the invention, which carries a carbazole substituent on the nitrogen, gives significantly better values than compound IC2 in accordance with the prior art having a terphenyl substituent. With B2, the power efficiency is improved by almost 15%, the lifetime by about 20%.

A significant improvement is also obtained on replacement of an indenocarbazole by a carbazole substituent (Examples V1 and E2). In this case, the lifetime increases to virtually double, and the improvement in the power efficiency of 20% is likewise very high. A significantly improved lifetime and power efficiency are also obtained with B29 compared with the biscarbazole BCbz1 (Examples V3 and E2).

On replacement of a bridged carbazole by an unbridged carbazole (Examples V5 and E2), the lifetime increases by 60%. Although a somewhat better quantum efficiency is obtained with compound ICvCbz1 in accordance with the prior art than with compound B29 according to the invention, the same power efficiency arises, however, owing to the better voltage.

If the emitter concentration in OLEDs comprising materials in accordance with the prior art is reduced to significantly below 10%, the efficiency and lifetime are reduced significantly. On use of compound IC2, for example, the external quantum efficiency is reduced by almost 10% when the emitter concentration is reduced from 10% to 4%. Much more significant is the impairment in the lifetime by a factor of more than 1.5 (Examples V7 and V8). With materials according to the invention, by contrast, no reduction in performance (Example E1 compared with E12) or even a slight improvement (Example E2 compared with E13-E15) can be observed.

On use as matrix materials in phosphorescent OLEDs, the materials according to the invention thus give rise to significant improvements compared with the prior art in some or all parameters. Furthermore, OLEDs having low emitter concentrations can be achieved with materials according to the invention without reductions in performance.

TABLE 1

Structure of the OLEDs

| Ex. | HTL thickness | IL thickness | EBL thickness | EML thickness | HBL thickness | ETL thickness |
|---|---|---|---|---|---|---|
| V1 | SpA1 70 nm | HATCN 5 nm | SpMA1 90 nm | IC1:BIC1:TEG1 (60%:30%:10%) 30 nm | IC1 10 nm | ST1:LiQ (50%:50%) 30 nm |
| V2 | SpA1 70 nm | HATCN 5 nm | SpMA1 90 nm | IC1:IC2:TEG1 (30%:60%:10%) 30 nm | IC1 10 nm | ST1:LiQ (50%:50%) 30 nm |
| V3 | SpA1 70 nm | HATCN 5 nm | SpMA1 90 nm | IC1:BCbz1:TEG1 (30%:60%:10%) 30 nm | IC1 10 nm | ST1:LiQ (50%:50%) 30 nm |
| V4 | SpA1 70 nm | HATCN 5 nm | SpMA1 90 nm | IC1:IC3:TEG1 (70%:20%:10%) 30 nm | IC1 10 nm | ST1:LiQ (50%:50%) 30 nm |
| V5 | SpA1 70 nm | HATCN 5 nm | SpMA1 90 nm | IC1:ICvCbz1:TEG1 (60%:30%:10%) 30 nm | IC1 10 nm | ST1:LiQ (50%:50%) 30 nm |
| V6 | SpA1 70 nm | HATCN 5 nm | BPA1 90 nm | ST1:BIC2:TEG1 (30%:60%:10%) 30 nm | ST1 10 nm | ST1:LiQ (50%:50%) 30 nm |
| V7 | SpA1 70 nm | HATCN 5 nm | PA1 90 nm | IC1:IC2:TEG1 (30%:60%:10%) 30 nm | ST1 10 nm | ST1:LiQ (50%:50%) 30 nm |
| V8 | SpA1 70 nm | HATCN 5 nm | PA1 90 nm | IC1:IC2:TEG1 (32%:64%:4%) 30 nm | ST1 10 nm | ST1:LiQ (50%:50%) 30 nm |
| E1 | SpA1 70 nm | HATCN 5 nm | SpMA1 90 nm | IC1:B2:TEG1 (30%:60%:10%) 30 nm | IC1 10 nm | ST1:LiQ (50%:50%) 30 nm |
| E2 | SpA1 70 nm | HATCN 5 nm | SpMA1 90 nm | IC1:B29:TEG1 (55%:35%:10%) 30 nm | IC1 10 nm | ST1:LiQ (50%:50%) 30 nm |
| E3 | SpA1 70 nm | HATCN 5 nm | SpMA1 90 nm | IC1:B30:TEG1 (65%:25%:10%) 30 nm | IC1 10 nm | ST1:LiQ (50%:50%) 30 nm |
| E4 | SpA1 70 nm | HATCN 5 nm | BPA1 90 nm | ST1:B26:TEG1 (30%:60%:10%) 30 nm | ST1 10 nm | ST1:LiQ (50%:50%) 30 nm |
| E5 | SpA1 70 nm | HATCN 5 nm | SpMA1 90 nm | IC1:B27:TEG1 (65%:25%:10%) 30 nm | IC1 10 nm | ST1:LiQ (50%:50%) 30 nm |
| E6 | SpA1 70 nm | HATCN 5 nm | SpMA1 90 nm | IC1:B5:TEG1 (30%:60%:10%) 30 nm | IC1 10 nm | ST1:LiQ (50%:50%) 30 nm |
| E7 | SpA1 70 nm | HATCN 5 nm | SpMA1 90 nm | IC1:B8:TEG1 (30%:60%:10%) 30 nm | IC1 10 nm | ST1:LiQ (50%:50%) 30 nm |
| E8 | SpA1 70 nm | HATCN 5 nm | SpMA1 90 nm | IC1:B14:TEG1 (30%:60%:10%) 30 nm | IC1 10 nm | ST1:LiQ (50%:50%) 30 nm |
| E9 | SpA1 70 nm | HATCN 5 nm | SpMA1 90 nm | ST1:B12:TEG1 (25%:65%:10%) 30 nm | ST1 10 nm | ST1:LiQ (50%:50%) 30 nm |
| E10 | SpA1 70 nm | HATCN 5 nm | SpMA1 90 nm | IC1:B24:TEG1 (50%:50%:10%) 30 nm | IC1 10 nm | ST1:LiQ (50%:50%) 30 nm |
| E11 | SpA1 70 nm | HATCN 5 nm | SpMA1 90 nm | ST1:B18:TEG1 (30%:60%:10%) 30 nm | ST1 10 nm | ST1:LiQ (50%:50%) 30 nm |
| E12 | SpA1 70 nm | HATCN 5 nm | SpMA1 90 nm | IC1:B2:TEG1 (32%:64%:4%) 30 nm | IC1 10 nm | ST1:LiQ (50%:50%) 30 nm |
| E13 | SpA1 70 nm | HATCN 5 nm | SpMA1 90 nm | IC1:B29:TEG1 (60%:39%:1%) 30 nm | IC1 10 nm | ST1:LiQ (50%:50%) 30 nm |
| E14 | SpA1 70 nm | HATCN 5 nm | SpMA1 90 nm | IC1:B29:TEG1 (59%:37%:4%) 30 nm | IC1 10 nm | ST1:LiQ (50%:50%) 30 nm |
| E15 | SpA1 70 nm | HATCN 5 nm | SpMA1 90 nm | IC1:B29:TEG1 (57%:36%:7%) 30 nm | IC1 10 nm | ST1:LiQ (50%:50%) 30 nm |
| E16 | SpA1 70 nm | HATCN 5 nm | SpMA1 90 nm | IC1:B10:TEG1 (45%:45%:10%) 30 nm | IC1 10 nm | ST1:LiQ (50%:50%) 30 nm |
| E17 | SpA1 70 nm | HATCN 5 nm | SpMA1 90 nm | IC1:B23:TEG1 (30%:60%:10%) 30 nm | IC1 10 nm | ST1:LiQ (50%:50%) 30 nm |

TABLE 2

Data of the OLEDs

| Ex. | U1000 (V) | CE1000 (cd/A) | PE1000 (lm/W) | EQE 1000 | CIE x/y at 1000 cd/m² | L0 | L1 % | LT (h) |
|---|---|---|---|---|---|---|---|---|
| V1 | 3.6 | 51 | 44 | 14.1% | 0.34/0.62 | 10000 cd/m² | 70 | 240 |
| V2 | 3.6 | 52 | 46 | 14.5% | 0.33/0.62 | 10000 cd/m² | 70 | 270 |
| V3 | 3.6 | 56 | 49 | 15.6% | 0.34/0.62 | 10000 cd/m² | 70 | 220 |
| V4 | 3.2 | 54 | 54 | 15.1% | 0.33/0.62 | 10000 cd/m² | 80 | 190 |
| V5 | 3.5 | 58 | 52 | 16.1% | 0.32/0.63 | 10000 cd/m² | 70 | 280 |
| V6 | 3.8 | 51 | 43 | 14.3% | 0.33/0.62 | 10000 cd/m² | 70 | 210 |
| V7 | 3.5 | 53 | 48 | 14.7% | 0.33/0.62 | 10000 cd/m² | 70 | 240 |
| V8 | 3.5 | 49 | 44 | 13.6% | 0.33/0.63 | 10000 cd/m² | 70 | 140 |
| E1 | 3.4 | 56 | 52 | 15.6% | 0.33/0.63 | 10000 cd/m² | 70 | 320 |
| E2 | 3.3 | 55 | 52 | 15.5% | 0.34/0.62 | 10000 cd/m² | 70 | 450 |
| E3 | 3.4 | 57 | 54 | 16.0% | 0.33/0.62 | 10000 cd/m² | 70 | 410 |
| E4 | 3.4 | 55 | 51 | 15.2% | 0.33/0.63 | 10000 cd/m² | 70 | 270 |
| E5 | 3.2 | 57 | 56 | 15.9% | 0.33/0.63 | 10000 cd/m² | 80 | 250 |
| E6 | 3.5 | 53 | 48 | 14.8% | 0.33/0.63 | 10000 cd/m² | 70 | 290 |
| E7 | 3.5 | 55 | 49 | 15.2% | 0.33/0.62 | 10000 cd/m² | 70 | 300 |
| E8 | 3.6 | 55 | 49 | 15.4% | 0.33/0.62 | 10000 cd/m² | 70 | 330 |
| E9 | 3.6 | 53 | 46 | 14.6% | 0.33/0.63 | 10000 cd/m² | 70 | 250 |
| E10 | 3.4 | 58 | 54 | 16.2% | 0.33/0.63 | 10000 cd/m² | 70 | 330 |
| E11 | 3.5 | 55 | 49 | 15.3% | 0.32/0.62 | 10000 cd/m² | 70 | 270 |
| E12 | 3.3 | 55 | 52 | 15.3% | 0.33/0.63 | 10000 cd/m² | 70 | 310 |
| E13 | 3.3 | 61 | 58 | 16.9% | 0.33/0.62 | 10000 cd/m² | 70 | 510 |
| E14 | 3.2 | 63 | 62 | 17.7% | 0.33/0.63 | 10000 cd/m² | 70 | 460 |
| E15 | 3.3 | 59 | 57 | 16.6% | 0.33/0.62 | 10000 cd/m² | 70 | 480 |
| E16 | 3.5 | 54 | 49 | 15.1% | 0.33/0.63 | 10000 cd/m² | 70 | 290 |
| E17 | 3.4 | 57 | 52 | 15.8% | 0.33/0.62 | 10000 cd/m² | 70 | 310 |

TABLE 3

Structural formulae of the materials for the OLEDs

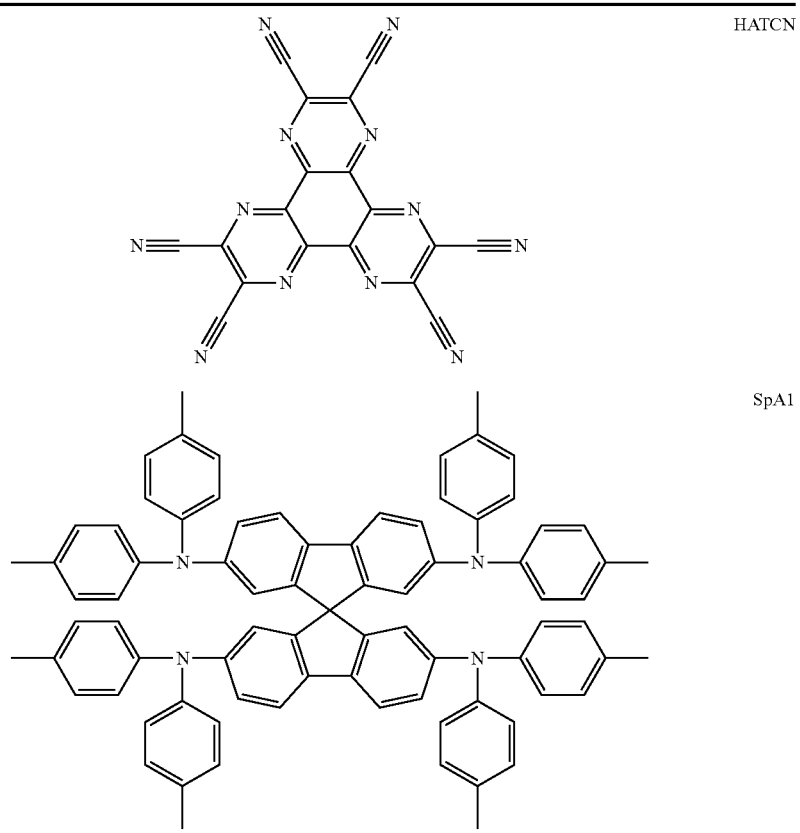

HATCN

SpA1

TABLE 3-continued
Structural formulae of the materials for the OLEDs
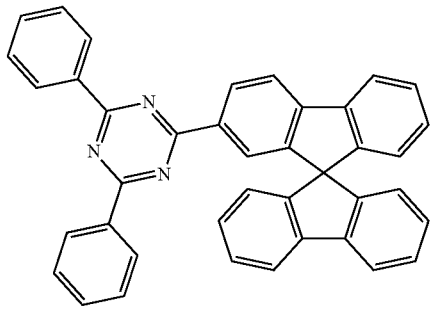 [SMILES: c1ccc(-c2nc(-c3ccccc3)nc(-c3ccc4c(c3)C3(c5ccccc5-c5ccccc53)c3ccccc3-4)n2)cc1]
ST1
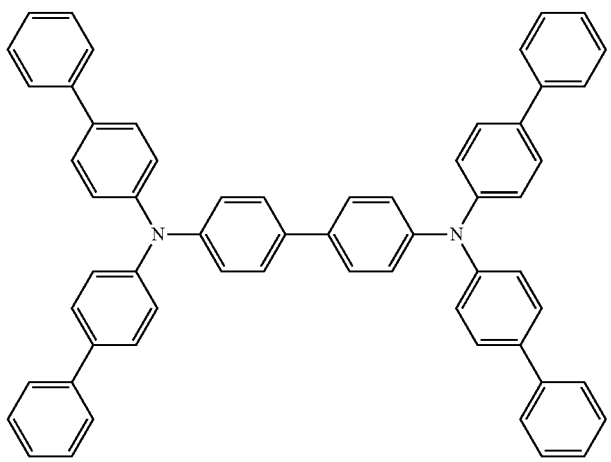 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]
BPA1
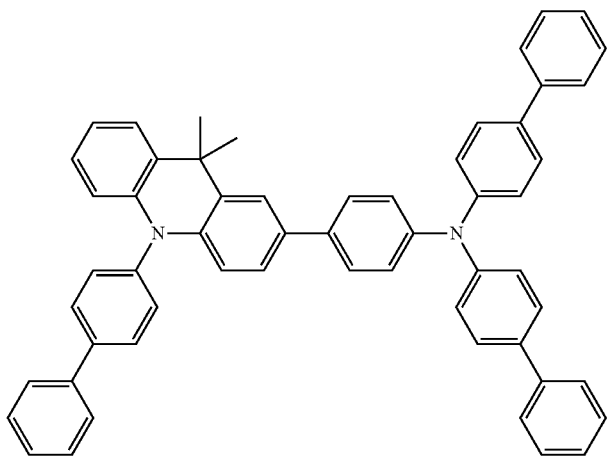 [SMILES: CC1(C)c2ccccc2N(c2ccc(-c3ccccc3)cc2)c2ccc(-c3ccc(N(c4ccc(-c5ccccc5)cc4)c4ccc(-c5ccccc5)cc4)cc3)cc21]
PA1
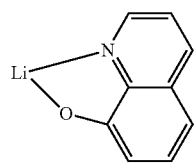
LiQ TABLE 3-continued
Structural formulae of the materials for the OLEDs
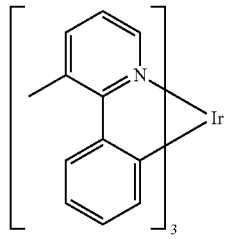 TEG1
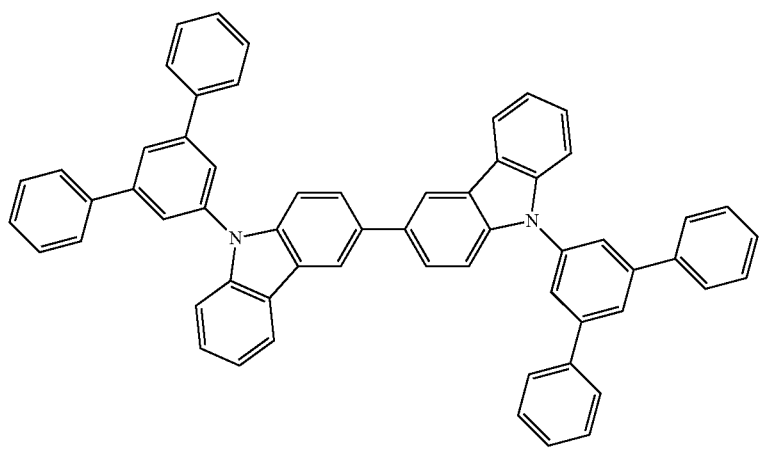 [SMILES: c1ccc(-c2cc(-c3ccccc3)cc(-n3c4ccccc4c4cc(-c5ccc6c(c5)c5ccccc5n6-c5cc(-c6ccccc6)cc(-c6ccccc6)c5)ccc43)c2)cc1] BCbz1
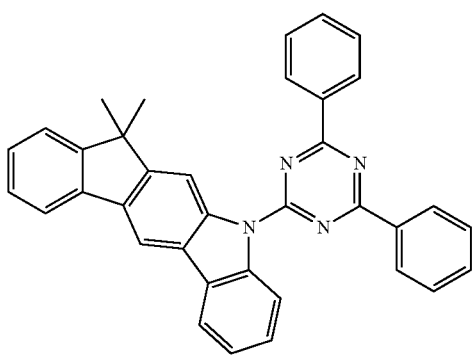 [SMILES: CC1(C)c2ccccc2-c2cc3c4ccccc4n(-c4nc(-c5ccccc5)nc(-c5ccccc5)n4)c3cc21] IC1
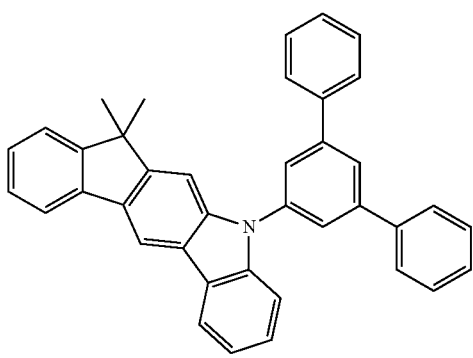 [SMILES: CC1(C)c2ccccc2-c2cc3c4ccccc4n(-c4cc(-c5ccccc5)cc(-c5ccccc5)c4)c3cc21] IC2

TABLE 3-continued
Structural formulae of the materials for the OLEDs
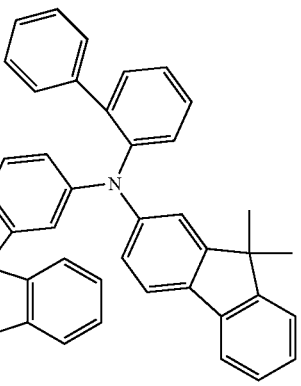
SpMA1
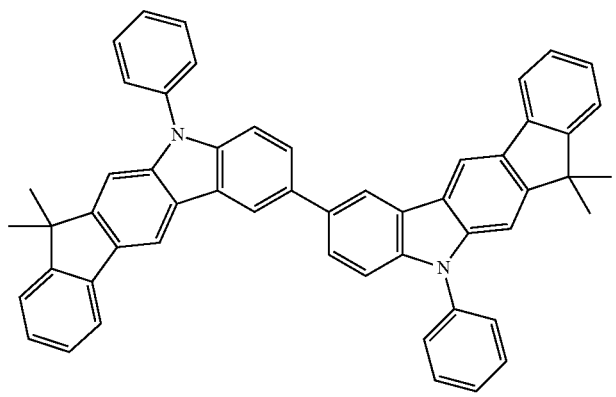
BIC1
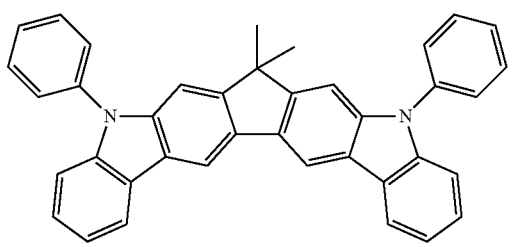 [SMILES: CC1(C)c2cc3c(cc2-c2cc4c5ccccc5n(-c5ccccc5)c4cc21)c1ccccc1n3-c1ccccc1]
IC3
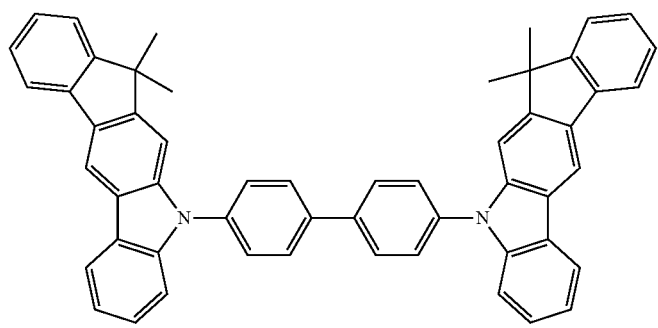 [SMILES: CC1(C)c2ccccc2-c2cc3c4ccccc4n(-c4ccc(-c5ccc(-n6c7ccccc7c7cc8c(cc76)C(C)(C)c6ccccc6-8)cc5)cc4)c3cc21]
BIC2

TABLE 3-continued
Structural formulae of the materials for the OLEDs
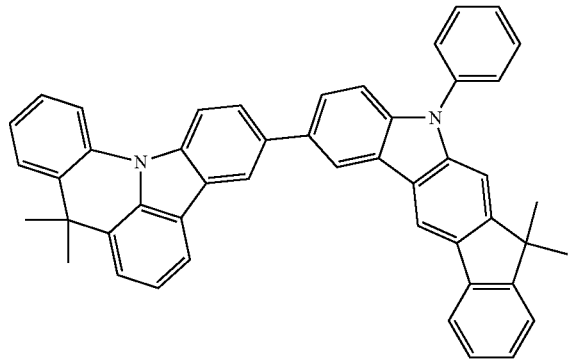 [SMILES: CC1(C)c2ccccc2-c2cc3c4cc(-c5ccc6c(c5)c5cccc7c5n6-c5ccccc5C7(C)C)ccc4n(-c4ccccc4)c3cc21]
ICvCbz1
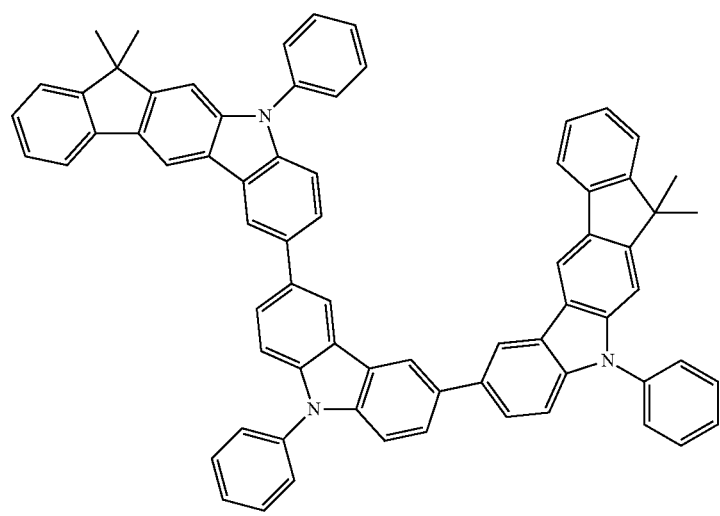 [SMILES: CC1(C)c2ccccc2-c2cc3c4cc(-c5ccc6c(c5)c5cc(-c7ccc8c(c7)c7cc9c(cc7n8-c7ccccc7)C(C)(C)c7ccccc7-9)ccc5n6-c5ccccc5)ccc4n(-c4ccccc4)c3cc21]
B30
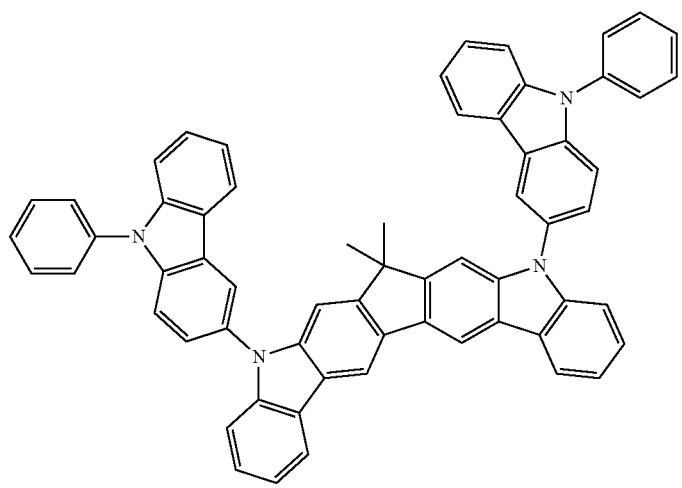 [SMILES: CC1(C)c2cc3c(cc2-c2cc4c5ccccc5n(-c5ccc6c(c5)c5ccccc5n6-c5ccccc5)c4cc21)c1ccccc1n3-c1ccc2c(c1)c1ccccc1n2-c1ccccc1]
B27

TABLE 3-continued
Structural formulae of the materials for the OLEDs
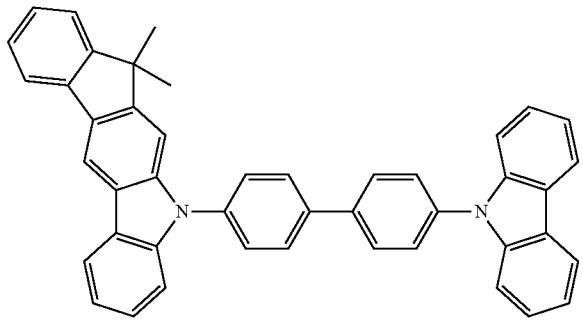 [SMILES: CC1(C)c2ccccc2-c2cc3c4ccccc4n(-c4ccc(-c5ccc(-n6c7ccccc7c7ccccc76)cc5)cc4)c3cc21]
B26
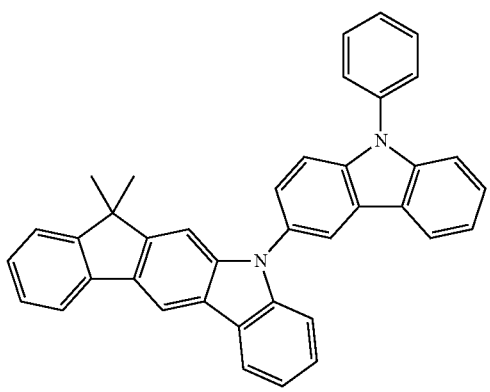 [SMILES: CC1(C)c2ccccc2-c2cc3c4ccccc4n(-c4ccc5c(c4)c4ccccc4n5-c4ccccc4)c3cc21]
B2
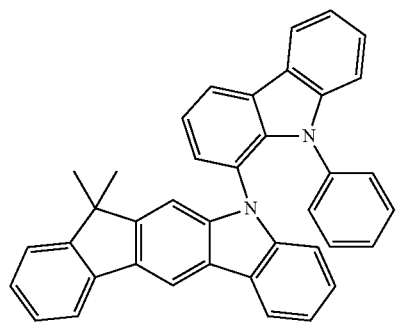 [SMILES: CC1(C)c2ccccc2-c2cc3c4ccccc4n(-c4cccc5c6ccccc6n(-c6ccccc6)c45)c3cc21]
B5
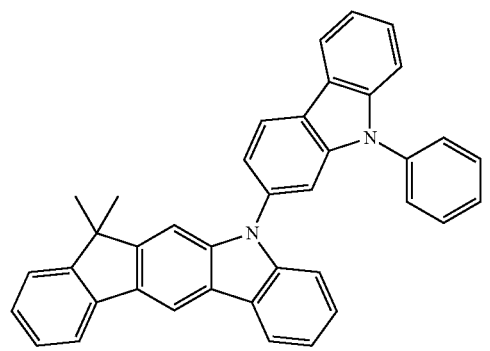 [SMILES: CC1(C)c2ccccc2-c2cc3c4ccccc4n(-c4ccc5c6ccccc6n(-c6ccccc6)c5c4)c3cc21]
B8

TABLE 3-continued
Structural formulae of the materials for the OLEDs
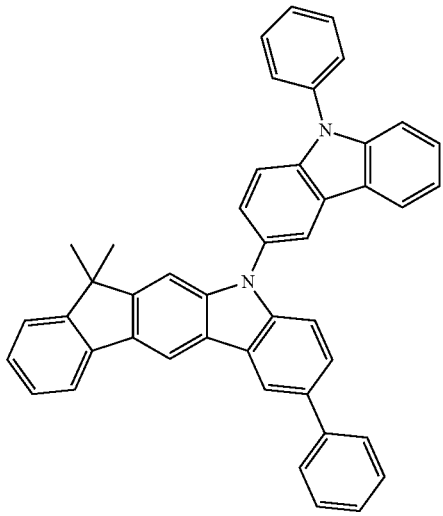 [SMILES: CC1(C)c2ccccc2-c2cc3c4cc(-c5ccccc5)ccc4n(-c4ccc5c(c4)c4ccccc4n5-c4ccccc4)c3cc21]
B14
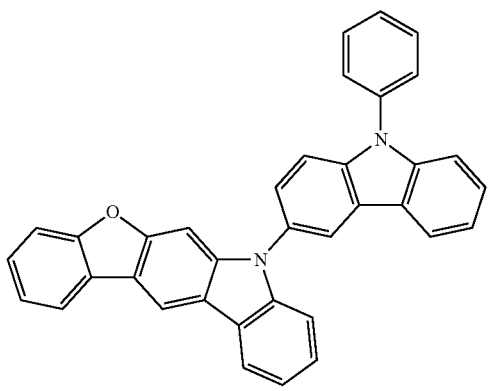 [SMILES: c1ccc(-n2c3ccccc3c3cc(-n4c5ccccc5c5cc6c(cc54)oc4ccccc46)ccc32)cc1]
B12
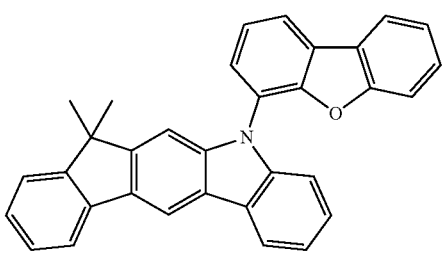 [SMILES: CC1(C)c2ccccc2-c2cc3c4ccccc4n(-c4cccc5c4oc4ccccc45)c3cc21]
B18

TABLE 3-continued
Structural formulae of the materials for the OLEDs
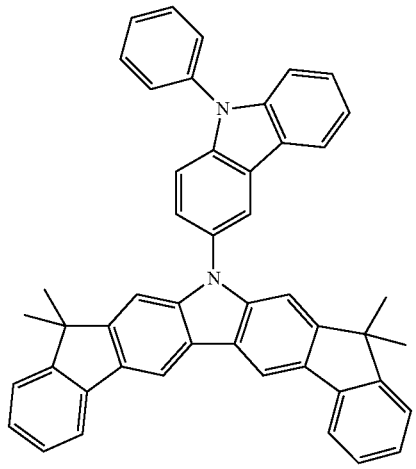 [SMILES: CC1(C)c2ccccc2-c2cc3c4cc5c(cc4n(-c4ccc6c(c4)c4ccccc4n6-c4ccccc4)c3cc21)C(C)(C)c1ccccc1-5]
B24
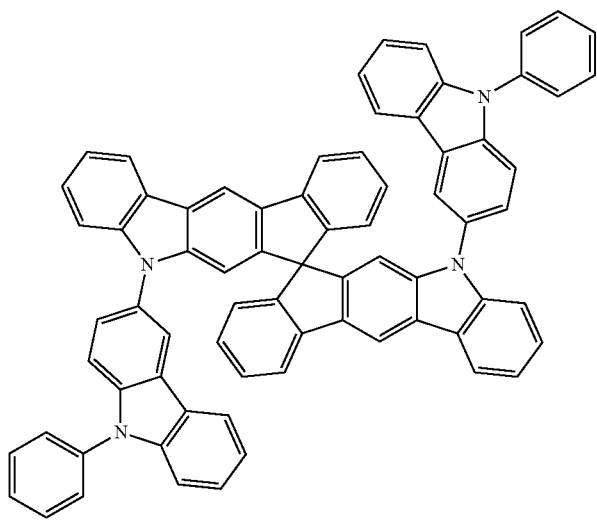 [SMILES: c1ccc(-n2c3ccccc3c3cc(-n4c5ccccc5c5cc6c(cc54)C4(c5ccccc5-6)c5ccccc5-c5cc6c7ccccc7n(-c7ccc8c(c7)c7ccccc7n8-c7ccccc7)c6cc54)ccc32)cc1]
B10
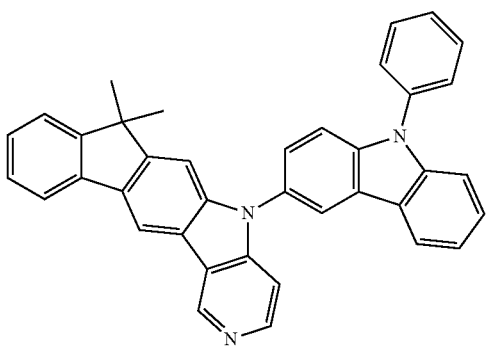 [SMILES: CC1(C)c2ccccc2-c2cc3c4cnccc4n(-c4ccc5c(c4)c4ccccc4n5-c4ccccc4)c3cc21]
B23

TABLE 3-continued

Structural formulae of the materials for the OLEDs

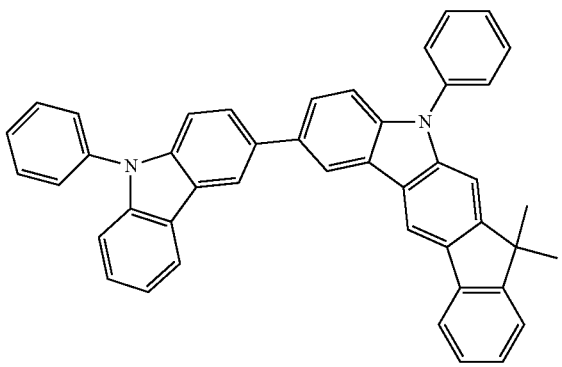 [SMILES: CC1(C)c2ccccc2-c2cc3c4cc(-c5ccc6c(c5)c5ccccc5n6-c5ccccc5)ccc4n(-c4ccccc4)c3cc21]

B29

The invention claimed is:

1. A compound of the formulae (6b), (7b) and (8b),

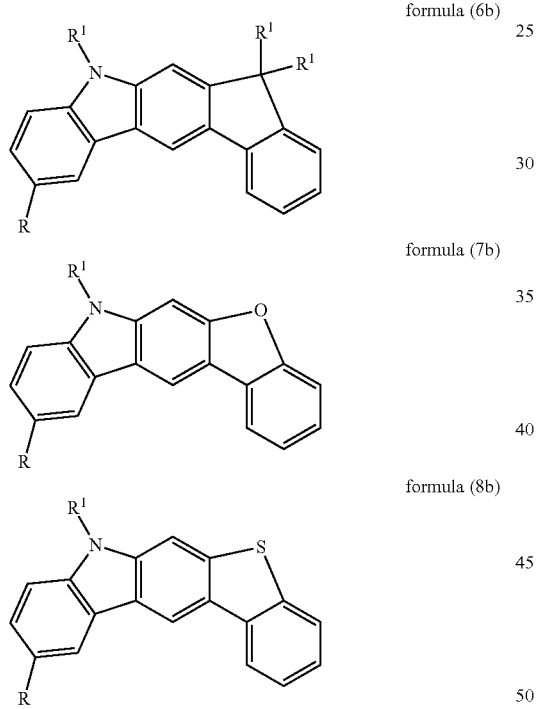

formula (6b)

formula (7b)

formula (8b)

where the following applies to the symbols used:

R and $R^1$ is on each occurrence, identically or differently, H, D, F, Cl, Br, I, $N(R^2)_2$, $N(Ar)_2$, C(=O)Ar, P(=O)Ar$_2$, S(=O)Ar, S(=O)$_2$Ar, $CR^2$=$CR^2$Ar, CN, NO$_2$, $Si(R^2)_3$, $B(OR^2)_2$, $OSO_2R^2$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^2$, where one or more non-adjacent CH$_2$ groups is optionally replaced by $R^2C$=$CR^2$, $Si(R^2)_2$, C=O, C=$NR^2$, P(=O)($R^2$), SO, SO$_2$, $NR^2$, O, S or $CONR_2$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or an aralkyl or heteroaralkyl group having 5 to 40 aromatic ring atoms, which is optionally substituted by one or more radicals $R^2$, or a combination of these systems; two or more substituents R here, together with the atoms to which they are bonded, or two substituents $R^1$, together with the atom to which they are bonded, may also form a mono- or polycyclic, aliphatic or aromatic ring system with one another;

Ar is on each occurrence, identically or differently, an aromatic or heteroaromatic ring system having 5 to 40 aromatic ring atoms, which is optionally substituted by one or more radicals $R^3$;

$R^2$ is on each occurrence, identically or differently, H, D, F, Cl, Br, I, $N(R^3)_2$, $N(Ar)_2$, C(=O)Ar, P(=O)Ar$_2$, S(=O)Ar, S(=O)$_2$Ar, $CR^3$=$CR^3$Ar, CN, NO$_2$, $Si(R^3)_3$, $B(OR^3)_2$, $OSO_2R^3$, a straight-chain alkyl, alkoxy or thioalkoxy group having 1 to 40 C atoms or a branched or cyclic alkyl, alkoxy or thioalkoxy group having 3 to 40 C atoms, each of which is optionally substituted by one or more radicals $R^3$, where one or more non-adjacent CH$_2$ groups is optionally replaced by $R^3C$=$CR^3$, $Si(R^3)_2$, C=O, C=$NR^3$, P(=O)($R^3$), SO, SO$_2$, $NR^3$, O, S or $CONR^3$ and where one or more H atoms is optionally replaced by D, F, Cl, Br, I, CN or NO$_2$, or an aromatic or heteroaromatic ring system having 5 to 60 aromatic ring atoms, which may in each case be substituted by one or more radicals $R^3$, or an aryloxy or heteroaryloxy group having 5 to 40 aromatic ring atoms, which is optionally substituted by one or more radicals $R^3$, or an aralkyl or heteroaralkyl group having 5 to 40 aromatic ring atoms, which is optionally substituted by one or more radicals $R^3$, or a combination of these systems;

$R^3$ is on each occurrence, identically or differently, H, D or an aliphatic hydrocarbon radical having 1 to 20 C atoms or an aryl or heteroaryl group having 5 to 40 ring atoms or a combination of these groups;

with the proviso that, if one or more of the groups R, $R^1$, $R^2$, $R^3$, Ar or $Ar^1$ contain heteroaryl groups which do not conform to the formulae (2), (3) these are not electron-deficient heteroaryl groups;

wherein at least one group R is present which stands, identically or differently on each occurrence, for a group of the following formula (2),

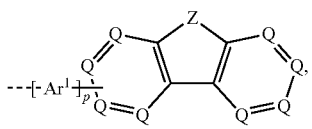

formula (2)

where the dashed bond indicates the linking of the group of the formula (2), R² has the above-mentioned meanings, and furthermore:

Q is C if the group of the formula (2) is linked to Ar¹ or to the remainder of the molecule via this group; or is, identically or differently on each occurrence, CR² or N in the other cases;

Z is NR² or S;

Ar¹ is a divalent aromatic or heteroaromatic ring system having 5 to 40 aromatic ring atoms, which is optionally substituted by one or more radicals R²;

p is 0 or 1;

and/or in that at least one group R¹ is present which stands for a group of the following formula (3)

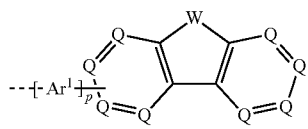

formula (3)

where the dashed bond indicates the linking of the group of the formula (3), R², Ar¹, Q and p have the above-mentioned meanings, and furthermore:

W is NR², O or S, and wherein in the compound of formula (6b) at least one group R is present which stands for a group of the formula (2) or at least one group R¹ is present which stands for a group of the formula (3); and wherein in the compounds of formula (7b) or (8b) at least one group R is present which stands for a group of the formula (2).

2. The compound according to claim 1, wherein the radical R¹ which is bonded to the nitrogen atom stands for an aromatic or heteroaromatic ring system having 5 to 60 aromatic ring atoms, which may also be substituted by one or more radicals R², or for a group of the formula (3).

3. The compound according to claim 1 where R¹ stands, identically or differently on each occurrence, for a straight-chain alkyl group having 1 to 10 C atoms or a branched or cyclic alkyl group having 3 to 10 C atoms, each of which is optionally substituted by one or more radicals R², where one or more non-adjacent CH₂ groups is optionally replaced by R²C=CR², C≡C, Si(R²)₂, C=O, O, S or CONR² and where one or more H atoms is optionally replaced by D, F or CN, or for an aromatic or heteroaromatic ring system having 5 to 60 aromatic ring atoms, which may also be substituted by one or more radicals R²; the radicals R¹ here may also form an aromatic or aliphatic ring system with one another.

4. The compound according to claim 1, wherein the groups of the formulae (2) to (3) are selected from the groups of the formulae (2a) to (3a),

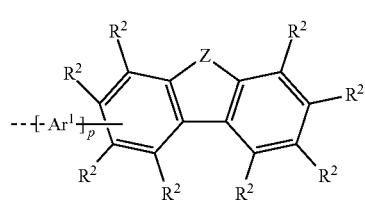

formula (2a)

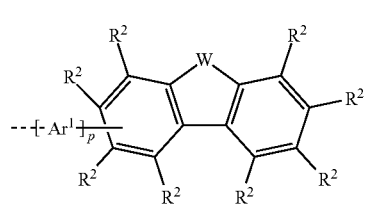

formula (3a)

where the symbols and indices used have the meanings given in claim 1, and, in formula (2a) and (3a), no group R² is bonded at the position at which the group is linked to Ar¹ or the remainder of the molecule.

5. The compound according to claim 1, wherein the groups of the formulae (2) to (3) are selected from the structures of the formulae (2b), (2c), (2d), (3b), (3c), and (3d),

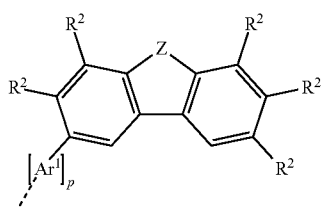

formula (2b)

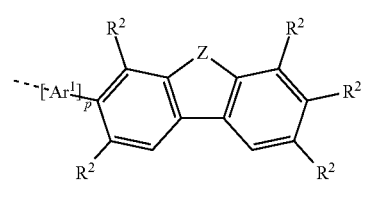

formula (2c)

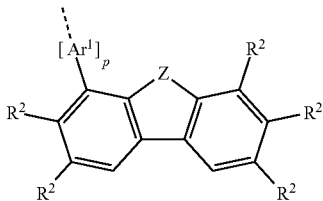

formula (2d)

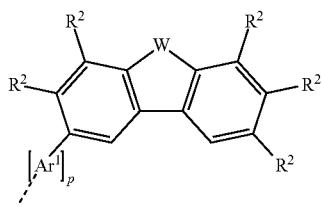

formula (3b)

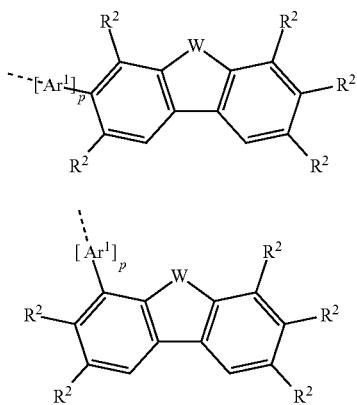

formula (3c)

formula (3d)

where the dashed bond indicates the linking of the group to the remainder of the molecule, and the other symbols and indices used have the meanings given in claim 1.

6. Compound according to claim 4, wherein the radicals $R^2$ which are bonded to a carbon atom in formula (2a) to (3a) stand for H.

7. Compound according to claim 5, wherein the radicals $R^2$ which are bonded to a carbon atom in formula (2b), (2c), (2d), (3b), (3c), and (3d), stand for H.

8. The compound according to claim 1, wherein Z or W stands for $NR^2$, where $R^2$ stands for an aromatic or heteroaromatic ring system.

9. A process for the preparation of a the compound according to claim 1, which comprises introducing the group of the formula (2) or (3) by a Suzuki coupling, an Ullmann coupling or by a Hartwig-Buchwald coupling.

10. A mixture comprising at least one compound according to claim 1 and at least one fluorescent or phosphorescent dopant.

11. A formulation comprising at least one compound according to claim 1 and one or more solvents.

12. The formulation according to claim 11, wherein the formulation is a solution, a suspension or a miniemulsion.

13. An electronic device comprising the compound according to claim 1.

14. The electronic device according to claim 13, wherein the device is selected from the group consisting of organic electroluminescent devices, organic integrated circuits, organic field-effect transistors, organic thin-film transistors, organic light-emitting transistors, organic solar cells, organic dye-sensitised solar cells, organic optical detectors, organic photoreceptors, organic field-quench devices, light-emitting electrochemical cells, organic laser diodes and organic plasmon emitting devices.

15. An organic electroluminescent device which comprises the compound according to claim 1 is employed as matrix material for a phosphorescent compound in an emitting layer.

* * * * *